United States Patent
Bruchman et al.

(10) Patent No.: US 10,022,219 B2
(45) Date of Patent: *Jul. 17, 2018

(54) DURABLE MULTI-LAYER HIGH STRENGTH POLYMER COMPOSITE SUITABLE FOR IMPLANT AND ARTICLES PRODUCED THEREFROM

(71) Applicant: W. L. Gore & Associates, Inc., Newark, DE (US)

(72) Inventors: William C. Bruchman, Camp Verde, AZ (US); Paul D. Gassler, Lincoln University, PA (US); Cody L. Hartman, Flagstaff, AZ (US); Peter J. Walsh, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/724,672

(22) Filed: May 28, 2015

(65) Prior Publication Data

US 2015/0257876 A1 Sep. 17, 2015

Related U.S. Application Data

(60) Continuation of application No. 14/598,979, filed on Jan. 16, 2015, which is a division of application No.
(Continued)

(51) Int. Cl.
*A61F 2/24* (2006.01)
*A61L 27/48* (2006.01)
(Continued)

(52) U.S. Cl.
CPC ............. *A61F 2/2403* (2013.01); *A61F 2/24* (2013.01); *A61F 2/2415* (2013.01); *A61L 27/34* (2013.01);
(Continued)

(58) Field of Classification Search
CPC ........ A61F 2/24–2/2424; A61F 2/2475; A61F 2210/0076
See application file for complete search history.

(56) References Cited

U.S. PATENT DOCUMENTS 3,953,566 A 4/1976 Gore
4,339,831 A 7/1982 Johnson
(Continued)

FOREIGN PATENT DOCUMENTS

EP 150608 8/1985
EP 293090 11/1988
(Continued)

OTHER PUBLICATIONS

International Search Report and Written Opinion for PCT/US2012/031417 dated Oct. 18, 2012, corresponding to U.S. Appl. No. 13/078,774.
(Continued)

*Primary Examiner* — Yashita Sharma
*Assistant Examiner* — Rebecca Preston
(74) *Attorney, Agent, or Firm* — Paul J. Fordenbacher, Esq.

(57) ABSTRACT

A thin, biocompatible, high-strength, composite material is disclosed that is suitable for use in various implanted configurations. The composite material maintains flexibility in high-cycle flexural applications, making it particularly applicable to high-flex implants such as a prosthetic heart valve leaflet. The composite material includes at least one porous expanded fluoropolymer layer and an elastomer present in the pores of the porous expanded fluoropolymer.

68 Claims, 43 Drawing Sheets

Related U.S. Application Data

13/485,823, filed on May 31, 2012, now Pat. No. 8,945,212, and a continuation-in-part of application No. 13/078,774, filed on Apr. 1, 2011, now Pat. No. 8,961,599.

(60) Provisional application No. 61/492,324, filed on Jun. 1, 2011.

(51) Int. Cl.
    *A61L 27/56*    (2006.01)
    *A61L 27/34*    (2006.01)
    *A61L 27/50*    (2006.01)

(52) U.S. Cl.
CPC ............ *A61L 27/48* (2013.01); *A61L 27/507* (2013.01); *A61L 27/56* (2013.01); *A61F 2210/0076* (2013.01); *A61F 2230/00* (2013.01); *A61F 2240/001* (2013.01); *A61F 2240/005* (2013.01); *A61L 2420/04* (2013.01); *A61L 2420/08* (2013.01); *A61L 2430/20* (2013.01); *Y10T 29/49412* (2015.01)

(56) References Cited

U.S. PATENT DOCUMENTS

| | | |
|---|---|---|
| 4,340,091 A | 7/1982 | Skelton et al. |
| 4,629,459 A | 12/1986 | Ionescu et al. |
| 4,955,899 A | 9/1990 | Della |
| 5,071,609 A | 12/1991 | Tb et al. |
| 5,708,044 A | 1/1998 | Branca |
| 6,451,396 B1 | 9/2002 | Zumbrum |
| 6,541,589 B1 | 4/2003 | Baillie |
| 6,673,455 B2 | 1/2004 | Zumbrum |
| 6,770,579 B1 | 8/2004 | Dawson |
| 6,776,604 B1 | 8/2004 | Chobotov et al. |
| 7,306,729 B2 | 12/2007 | Bacino |
| 7,448,122 B1 | 11/2008 | Kokish et al. |
| 7,462,675 B2 | 12/2008 | Chang et al. |
| 7,531,611 B2 | 5/2009 | Sabol et al. |
| 7,628,803 B2 | 12/2009 | Pavcnik et al. |
| 7,789,908 B2 | 9/2010 | Sowinski et al. |
| 8,637,144 B2 | 1/2014 | Ford |
| 8,945,212 B2 * | 2/2015 | Bruchman ............ A61F 2/2415 623/2.12 |
| 2001/0051824 A1 | 12/2001 | Hopkins |
| 2003/0004559 A1 | 1/2003 | Lentz et al. |
| 2003/0004560 A1 | 1/2003 | Chobotov et al. |
| 2003/0055492 A1 | 3/2003 | Shaolian et al. |
| 2003/0055495 A1 | 3/2003 | Pease et al. |
| 2003/0211264 A1 | 11/2003 | Farnsworth et al. |
| 2004/0019374 A1 | 1/2004 | Hojeibane et al. |
| 2004/0024448 A1 | 2/2004 | Chang et al. |
| 2004/0093070 A1 | 5/2004 | Hojeibane et al. |
| 2005/0137682 A1 | 6/2005 | Justino |
| 2006/0058889 A1 | 3/2006 | Case et al. |
| 2006/0259133 A1 | 11/2006 | Sowinski et al. |
| 2007/0027535 A1 | 2/2007 | Purdy |
| 2007/0118210 A1 | 5/2007 | Pinchuk |
| 2007/0288087 A1 | 12/2007 | Fearnot et al. |
| 2008/0091261 A1 | 4/2008 | Long et al. |
| 2008/0125711 A1 | 5/2008 | Alpini et al. |
| 2009/0004239 A1 | 1/2009 | Ladet |
| 2009/0187197 A1 | 7/2009 | Roeber |
| 2010/0190254 A1 | 7/2010 | Chian |
| 2010/0248324 A1 | 9/2010 | Xu et al. |
| 2010/0249922 A1 | 9/2010 | Li |
| 2011/0039690 A1 | 2/2011 | Niu |
| 2011/0142804 A1 | 6/2011 | Gaudette |
| 2011/0250689 A1 | 10/2011 | Baaijens |
| 2011/0311746 A1 | 12/2011 | Ma |
| 2012/0058100 A1 | 3/2012 | Shastri |
| 2012/0061314 A1 | 3/2012 | Choi |
| 2012/0129150 A1 | 5/2012 | Carbonell |
| 2012/0253453 A1 | 10/2012 | Bruchman et al. |
| 2012/0290082 A1 | 11/2012 | Quint et al. |
| 2012/0296418 A1 | 11/2012 | Bonyuet |
| 2012/0323315 A1 | 12/2012 | Bruchman et al. |
| 2013/0150947 A1 | 6/2013 | Kaufmann |
| 2013/0166021 A1 * | 6/2013 | Bruchman ............ A61F 2/2415 623/2.12 |
| 2013/0310924 A1 | 11/2013 | Groothuis |
| 2014/0180400 A1 | 6/2014 | Bruchman et al. |
| 2014/0288642 A1 | 9/2014 | Yoshida |
| 2015/0224231 A1 | 8/2015 | Bruchman |
| 2015/0257876 A1 | 9/2015 | Bruchman |
| 2015/0265744 A1 | 9/2015 | Baaijens |
| 2015/0283297 A1 | 10/2015 | Baaijens |
| 2015/0305862 A1 | 10/2015 | Bruchman |
| 2015/0306277 A1 | 10/2015 | Pathak |
| 2015/0366663 A1 | 12/2015 | Bruchman |
| 2016/0008133 A9 | 1/2016 | Day |
| 2016/0067374 A1 | 3/2016 | Puckett |

FOREIGN PATENT DOCUMENTS

| | | |
|---|---|---|
| EP | 773971 | 5/1997 |
| EP | 1 977 719 | 10/2008 |
| WO | 95/28899 | 11/1995 |
| WO | 98/26731 | 6/1998 |
| WO | 02/100454 | 12/2002 |
| WO | 2004/000375 | 12/2003 |
| WO | 2006/000763 | 1/2006 |
| WO | 2007/002320 | 1/2007 |
| WO | 2007/016251 | 2/2007 |
| WO | 2009/038761 | 3/2009 |
| WO | 2009/149462 | 12/2009 |
| WO | 2011/065809 | 6/2011 |

OTHER PUBLICATIONS

International Search Report and Written Opinion for PCT/US2012/040529 dated Nov. 14, 2012 corresponding to U.S. Appl. No. 13/485,823.
Annex to Form PCT/ISA/206 Communication Relating to the Results of the Partial International Search PCT/US2014/016550 dated Apr. 8, 2014, corresponding to U.S. Appl. No. 13/798,595; 3 pages.
International Search Report and Written Opinion for PCT/US2014/016581 dated Apr. 8, 2014, corresponding to U.S. Appl. No. 13/801,701; 4 pages.
International Search Report and Written Opinion for PCT/US2014/016550 dated Jul. 2, 2014, corresponding to U.S. Appl. No. 13/798,595; 9 pages.
International Search Report and Written dated May 30, 2014, corresponding Opinion for PCT/US2014/016807 to U.S. Appl. No. 14/181,965, 4 pages.
International Search Report and Written Opinion for PCT/US2015/042530 dated Oct. 6, 2015, corresponding to U.S. Appl. No. 14/622,599, 3 pages.

* cited by examiner

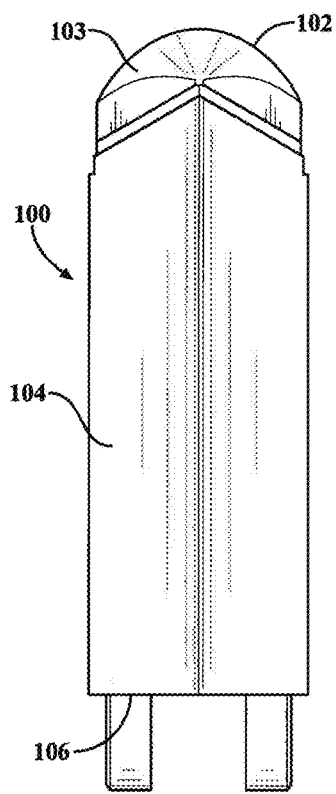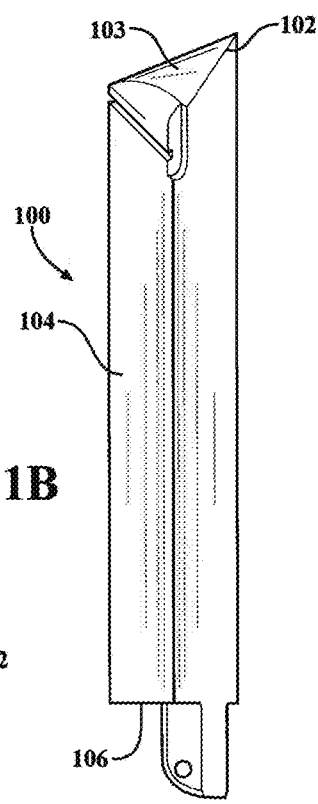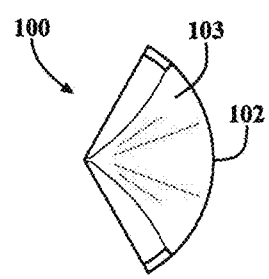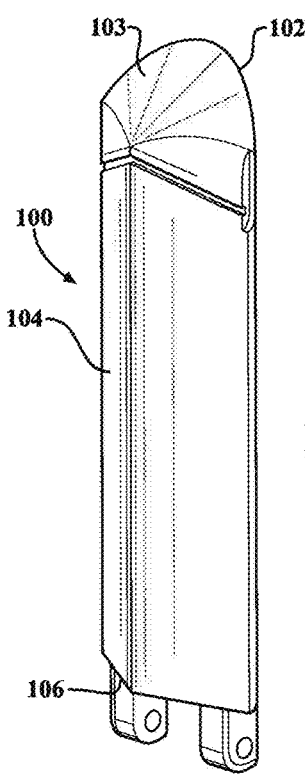
FIG. 1A
FIG. 1B
FIG. 1C
FIG. 1D

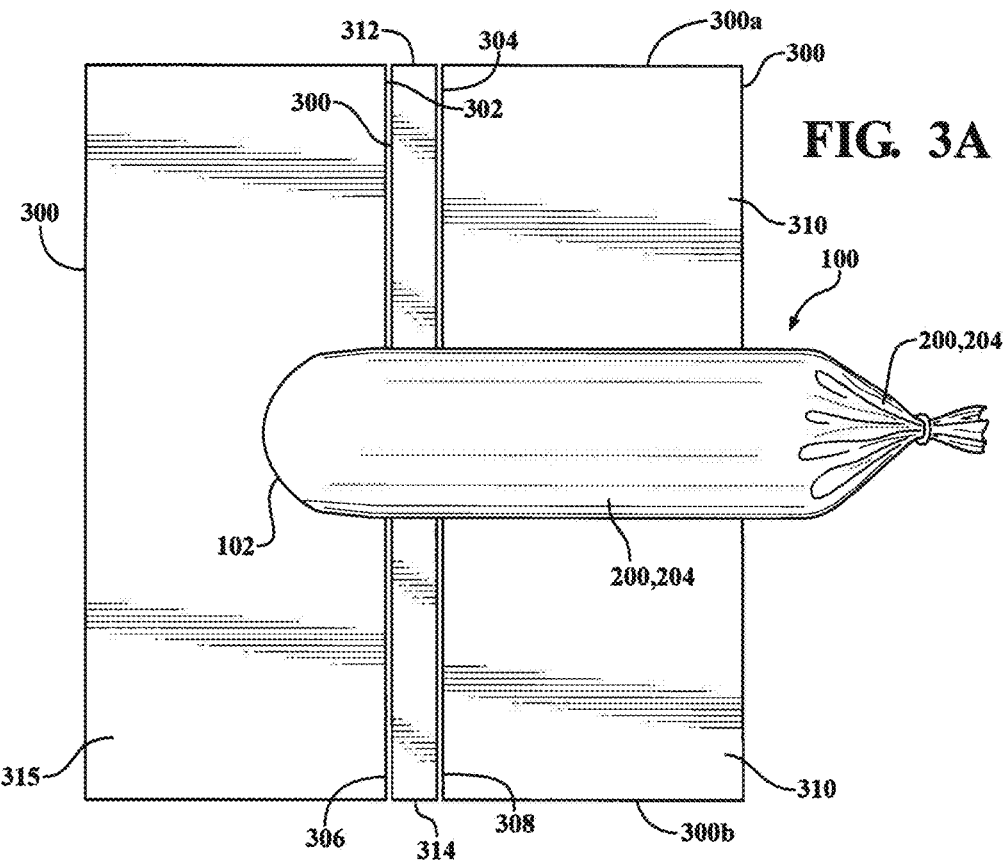
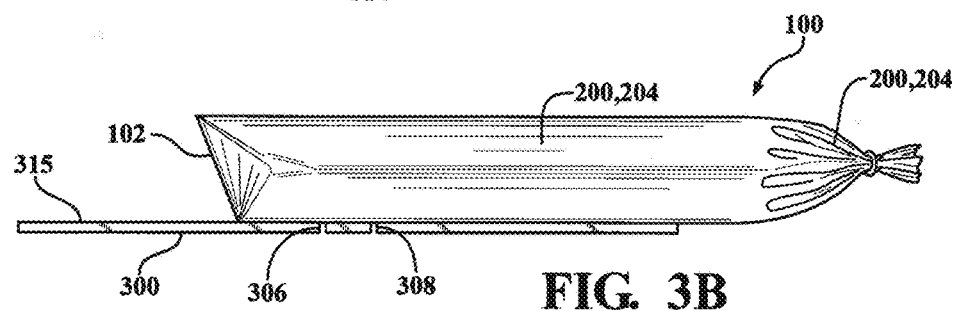
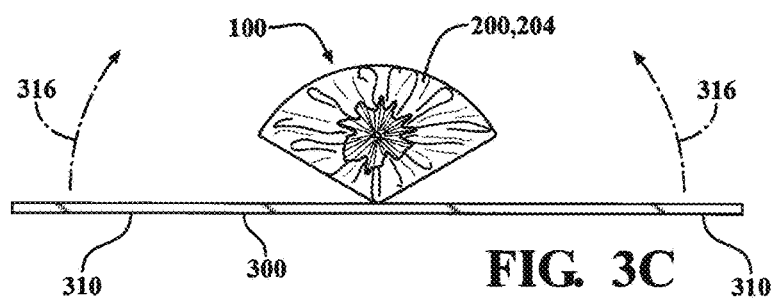

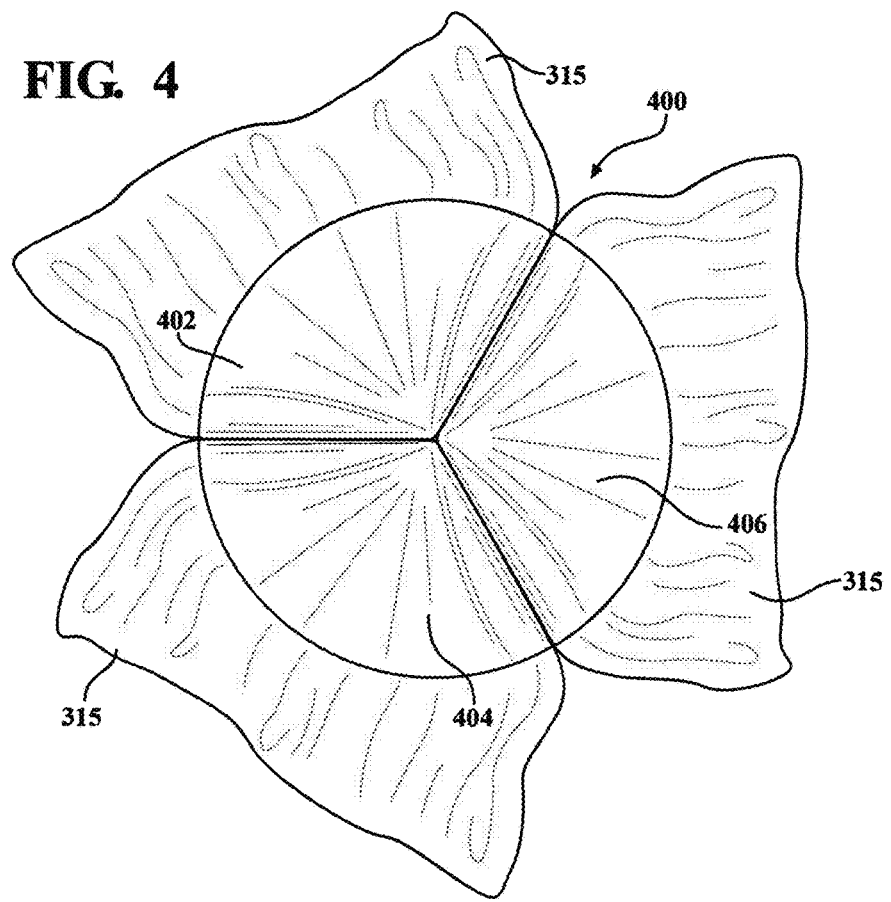

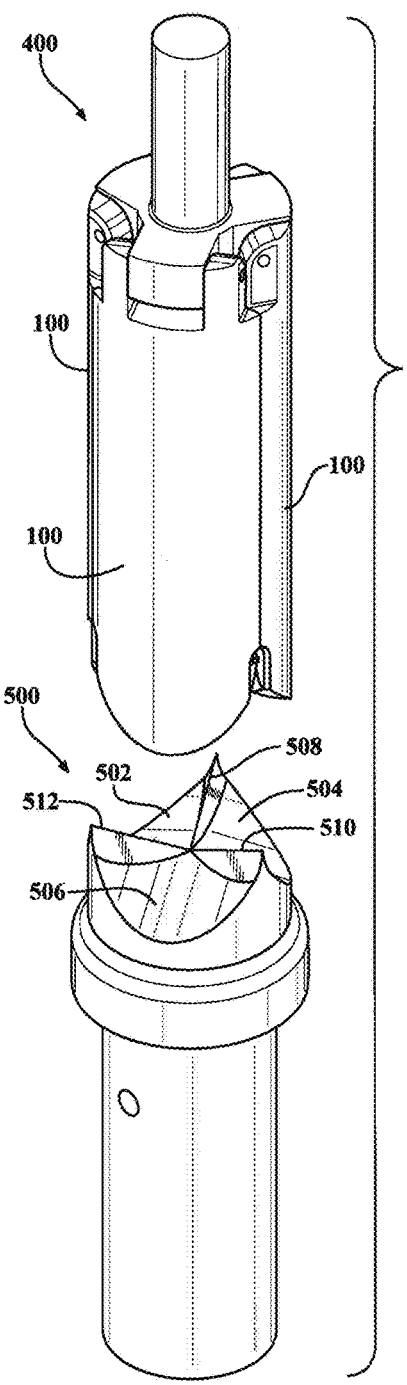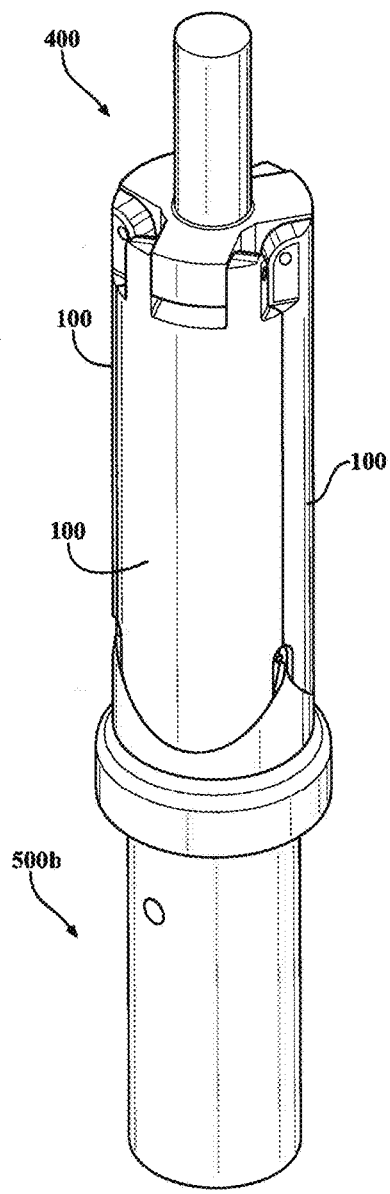
FIG. 5A
FIG. 5B

FIG. 11B

Statistics on Pressure Peaks

Pressure Peaks

| 133.61 | 103.76 | 158.54 | 107.03 | 139.99 | 121.69 | 139.99 |
|---|---|---|---|---|---|---|

| | | | |
|---|---|---|---|
| Time Stamp | 5/11/2009@10:31 AM | Run# | 586 |
| ID | 87905 PPT PATT (stn E pp91) | Speed (cpm) | 779 |
| Target Pressure (mmHg) | 95.00 | Cycles | 2.47.808E+6 |
| Datapoints/Cycle | 77.02 | | |
| # of Peaks | 51 | | |
| Max of Peaks | 158.54 | | |
| Min of Peaks | 101.85 | | |
| Mean | 126.87 | | |
| Standard Deviation | 14.77 | | |
| # Below Target | 0 | | |
| % Below Target | 0.00 | | |
| Target Distance from Mean (Std.) | -2.16 | | |
| Theoretical % Below Target | 1.55 | (5% when -1.645 Std. Dev. Away) | |

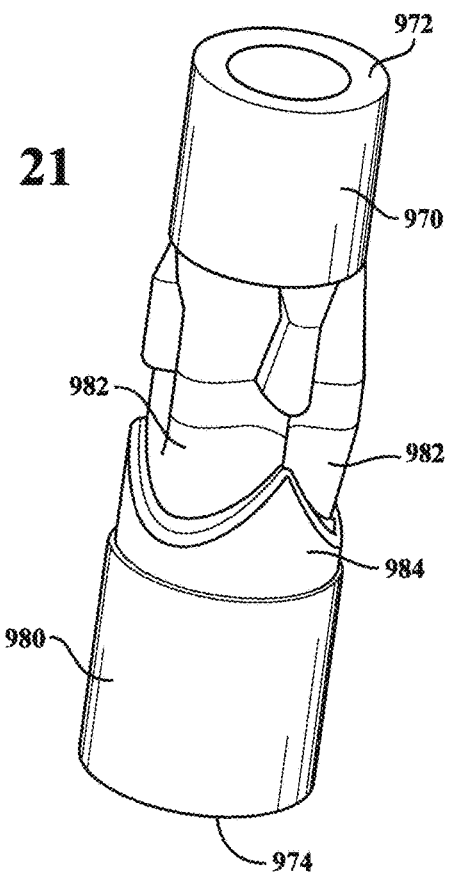
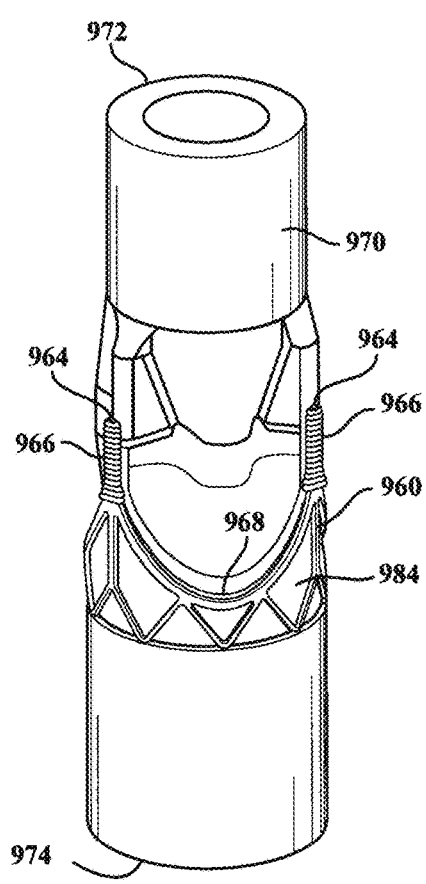
FIG. 21
FIG. 22

Table 4

| Example Number | Example 4a | Example 4b | Example 4c | Example 5 | Example 6 | Example 7 | Example 8 |
|---|---|---|---|---|---|---|---|
| Frame Type | non-collapsible | non-collapsible | Non-collapsible | non-collapsible | non-collapsible | collapsible | non-collapsible |
| Cushion Layer | No | No | Yes | No | Yes | Yes | Yes |
| Leaflet Thickness (μm) | 50.3 | 52.0 | 52.3 | 98.3 | 49.7 | 25.0 | 48.0 |
| Volume Fraction (% ePTFE) | 28.22 | 9.74 | 8.91 | 9.74 | 29.9 | 25.0 | 24.00 |
| Elastomeric Material | PMVE | PMVE | PMVE | PMVE | PMVE | PMVE | Silicone |
| Number of Layers | 26 | 9 | 4 | 18 | 95 | 57 | 45 |
| (Thickness) / (# of Layers) | 1.93 | 5.78 | 13.08 | 5.46 | 0.52 | 0.44 | 1.07 |
| Membrane Properties: | | | | | | | |
| Mass / Area (g/m²) | 1.15 | 1.15 | 2.27 | 1.15 | 0.31 | 0.29 | 0.57 |
| Thickness (nm) | 1016 | 1016 | 3556 | 1016 | 127 | 158 | 2500 |
| MTS in MD (MPa) | 410.9 | 410.9 | 319.4 | 410.9 | 442.0 | 434.0 | 339 |
| MTS in TD (MPa) | 315.4 | 315.4 | 407.3 | 315.4 | 560.0 | 646.0 | 257 |
| Bubble Point (MPa) | 79.7 | 79.7 | 101.5 | 79.7 | 0.11 | 0.11 | 0.46 |
| Density (g/cm³) | 1.059 | 1.059 | 0.637 | 1.059 | 0.400 | 0.400 | 0.221 |
| Composite Properties: | | | | | | | |
| Thickness (μm) | 1.93 | 5.78 | 13.08 | 5.46 | 0.52 | 0.44 | 1.07 |
| Mass / Area (g/m²) | 4.08 | 11.8 | 25.48 | 11.80 | 1.04 | 0.94 | N/A |
| Volume Fraction (% ePTFE) | 28.22 | 9.74 | 8.91 | 9.74 | 29.9 | 30.3 | 24.00 |
| Dome Burst (KPa) | 15.9 | 17.3 | 31.7 | 17.3 | 4.8 | 4.14 | N/A |

FIG. 43

Table 6

| Example Number | | Example 4a | Example 4b | Example 4c | Example 5 | Example 6 | Example 7 | Example 8 |
|---|---|---|---|---|---|---|---|---|
| Collapsible Frame | | No | No | No | No | No | Yes | No |
| Effective Orifice Area (EOA, cm²) | | | | | | | | |
| Compaction & Expansion | Pre | 1.88 | 2.05 | N/A | 1.73 | 2.19 | 2.10 | 2.4 |
| | Post | N/A | N/A | N/A | N/A | N/A | 2.20 | N/A |
| At removal | | 2.17 @100million | Failed @ 6 million | Failed @ 12.4 million | 2.109 @100million | 2.04, @100million | 2+ million cycles in animal | 2.4 @150million |
| Regurgitant Fraction (RF, %) | | | | | | | | |
| Compaction & Expansion | Pre | 10.86 | 11.71 | N/A | 11.71 | 9.70 | 25.9 | 12.5 |
| | Post | N/A | N/A | N/A | N/A | N/A | 22.0 | N/A |
| At removal | | 15.66 @100million | Failed @ 6 million | Failed @ 12.4 million | 9.50 @100million | 13.7, @100million | 2+ million cycles in animal | 28.0 @150million |
| Construction & Leaflet Failures Observed | | | | | | | | |
| Frame Detachment | | | X | | X | | | |
| Leaflet | Hole | | | X | | | | |
| | Tear | | | | | | | |
| | Delaminate | | | | X | | | |

FIG. 44

DURABLE MULTI-LAYER HIGH STRENGTH POLYMER COMPOSITE SUITABLE FOR IMPLANT AND ARTICLES PRODUCED THEREFROM

BACKGROUND

Field

This disclosure relates to materials used in medical implants. More particularly, the disclosure relates to a biocompatible material suitable for use in high-cycle flexural applications including artificial heart valves.

Background

Artificial heart valves preferably should last at least ten years in vivo. To last that long, artificial heart valves should exhibit sufficient durability for at least four hundred million cycles or more. The valves, and more specifically heart valve leaflets, must resist structural degradation including the formation of holes, tears, and the like, as well as adverse biological consequences including calcification and thrombosis.

Fluoropolymers, such as expanded and non-expanded forms of polytetrafluoroethylene (PTFE), modified PTFE, and copolymers of PTFE, offer a number of desirable properties, including excellent inertness and superior biocompatibility, and, therefore make ideal candidate materials. PTFE and expanded PTFE (ePTFE) have been used to create heart valve leaflets. It has been shown, however, that PTFE stiffens with repeated flexure, which can lead to unacceptable flow performance. Failure due to formation of holes and tears in the material has also been observed. A variety of polymeric materials have previously been employed as prosthetic heart valve leaflets. Failure of these leaflets due to stiffening and hole formation occurred within two years of implant. Efforts to improve leaflet durability by thickening the leaflets resulted in unacceptable hemodynamic performance of the valves, that is, the pressure drop across the open valve was too high.

As such, it remains desirable to provide a biocompatible artificial heart valve design that lasts at least ten years in vivo by exhibiting sufficient durability for at least about four hundred million cycles of flexure or more.

SUMMARY

According to embodiments, an implantable article is provided for regulating blood flow direction in a human patient. Such an article may include, but is not limited to, a cardiac valve or a venous valve In one embodiment, the implantable article includes a leaflet comprising a composite material with at least one fluoropolymer layer having a plurality of pores and an elastomer present in substantially all of the pores of the at least one fluoropolymer layer, wherein the composite material comprises less than about 80% fluoropolymer by weight.

In other exemplary embodiments, the implantable article includes a leaflet having a thickness and formed from a composite material having more than one fluoropolymer layer having a plurality of pores and an elastomer present in substantially all of the pores of the more than one fluoropolymer layer, wherein the leaflet has a ratio of leaflet thickness ($\mu m$) to number of layers of fluoropolymer of less than about 5.

In other exemplary embodiments, the implantable article includes a support structure; a leaflet supported on the support structure, the leaflet having a thickness and formed from a composite material having more than one fluoropolymer layer having a plurality of pores and an elastomer present in substantially all of the pores of the more than one fluoropolymer layer, wherein the leaflet has a ratio of leaflet thickness ($\mu m$) to number of layers of fluoropolymer of less than about 5.

In other exemplary embodiments, the implantable article includes a leaflet cyclable between a closed configuration for substantially preventing blood flow through the implantable article and an open configuration allowing blood flow through the implantable article. The leaflet is formed from a plurality of fluoropolymer layers and having a ratio of leaflet thickness ($\mu m$) to number of layers of fluoropolymer of less than about 5. The leaflet maintains substantially unchanged performance after actuation of the leaflet at least 40 million cycles.

In other exemplary embodiments, the implantable article includes a leaflet cyclable between a closed configuration for substantially preventing blood flow through the implantable article and an open configuration allowing blood flow through the implantable article. The implantable article also includes a cushion member located between at least a portion of the support structure and at least a portion of the leaflet, wherein the cushion member is formed from a plurality of fluoropolymer layers and having a ratio of leaflet thickness ($\mu m$) to number of layers of fluoropolymer of less than about 5. The leaflet maintains substantially unchanged performance after actuation of the leaflet at least 40 million cycles.

In exemplary embodiments, a method is provided for forming a leaflet of an implantable article for regulating blood flow direction in a human patient, which includes the steps of: providing a composite material having more than one fluoropolymer layer having a plurality of pores and an elastomer present in substantially all of the pores of the more than one fluoropolymer layer; and bringing more than one layer of the composite material into contact with additional layers of the composite material by wrapping a sheet of the composite material with a starting and ending point defined as an axial seam adhered to itself.

In exemplary embodiments, an implantable article is provided for regulating blood flow direction in a human patient, which includes a polymeric leaflet having a thickness of less than about 100 $\mu m$.

In another embodiment, the implantable article includes a generally annular shaped support structure having a first end and an opposite second end. The first end of the support structure has a longitudinally extending post. A sheet of leaflet material extends along an outer periphery of the support structure and forms first and second leaflets extending along on opposite sides of the post. A cushion member is coupled to the post and provides a cushion between the post and the leaflets to minimize stress and wear on the leaflets as the leaflets cycle between open and closed positions.

BRIEF DESCRIPTION OF THE DRAWINGS

The accompanying drawings are included to provide a further understanding of the invention and are incorporated in and constitute a part of this specification, illustrate exemplary embodiments of the invention, and together with the description serve to explain the principles of the invention.

FIGS. 1A, 1B, 1C, and 1D are front, side and top elevational views, and a perspective view, respectively, of a tool for forming a heart valve leaflet, in accordance with an embodiment;

FIGS. 3A, 3B and 3C are top, side and front elevational views illustrating a step in the formation of a valve leaflet, in which the leaflet tool covered by the cushion pad and release layer (shown in FIGS. 2A and 2B, respectively) is positioned over a composite material for cutting and further assembly, in accordance with an embodiment;

FIG. 4 is a top elevational view of a tri-leaflet assembly prior to cutting excess leaflet material, in accordance with an embodiment;

FIG. 5A is a perspective view of the tri-leaflet assembly and a base tool, in accordance with an embodiment;

FIG. 5B is a perspective view of the tri-leaflet assembly and base tool aligned and assembled to form a base tool assembly, in accordance with an embodiment;

FIGS. 11A and 11B are a graph and data chart of measured outputs from a high rate fatigue tester used for measuring performance of the valve assemblies;

FIG. 21 is a perspective view of a stereolithography-formed mandrel, in accordance with an embodiment;

FIG. 22 is a perspective view of the cushion-wrapped valve frame of FIG. 20 mounted onto the mandrel of FIG. 21, in accordance with an embodiment;

FIG. 43 is Table 4, which is a table of performance data for example valves, in accordance with embodiments; and FIG. 44 is Table 6, which is a table of performance data for example valves, in accordance with embodiments.

DETAILED DESCRIPTION OF THE ILLUSTRATED EMBODIMENTS

Definitions for some terms used herein are provided below in the Appendix.

The embodiments presented herein address a long-felt need for a material that meets the durability and biocompatibility requirements of high-cycle flexural implant applications, such as heart valve leaflets. It has been observed that heart valve leaflets formed from porous fluoropolymer materials or, more particularly, from ePTFE containing no elastomer suffer from stiffening in high-cycle flex testing and animal implantation.

In one embodiment, described in greater detail below, the flexural durability of porous fluoropolymer heart valve leaflets was significantly increased by adding a relatively high-percentage of relatively lower strength elastomer to the pores. Optionally, additional layers of the elastomer may be added between the composite layers. Surprisingly, in embodiments wherein porous fluoropolymer membranes are imbibed with elastomer the presence of the elastomer increased overall thickness of the leaflet, the resulting increased thickness of the fluoropolymer members due to the addition of the elastomer did not hinder or diminish flexural durability. Further, after reaching a minimum percent by weight of elastomer, it was found that fluoropolymer members in general performed better with increasing percentages of elastomer resulting in significantly increased cycle lives exceeding 40 million cycles in vitro, as well as by showing no signs of calcification under certain controlled laboratory conditions.

A material according to one embodiment includes a composite material comprising an expanded fluoropolymer membrane and an elastomeric material. It should be readily appreciated that multiple types of fluoropolymer membranes and multiple types of elastomeric materials can be combined while within the spirit of the present embodiments. It should also be readily appreciated that the elastomeric material can include multiple elastomers, multiple types of non-elastomeric components, such as inorganic fillers, therapeutic agents, radiopaque markers, and the like while within the spirit of the present embodiments.

In one embodiment, the composite material includes an expanded fluoropolymer material made from porous ePTFE membrane, for instance as generally described in U.S. Pat. No. 7,306,729.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

Figure 7A:
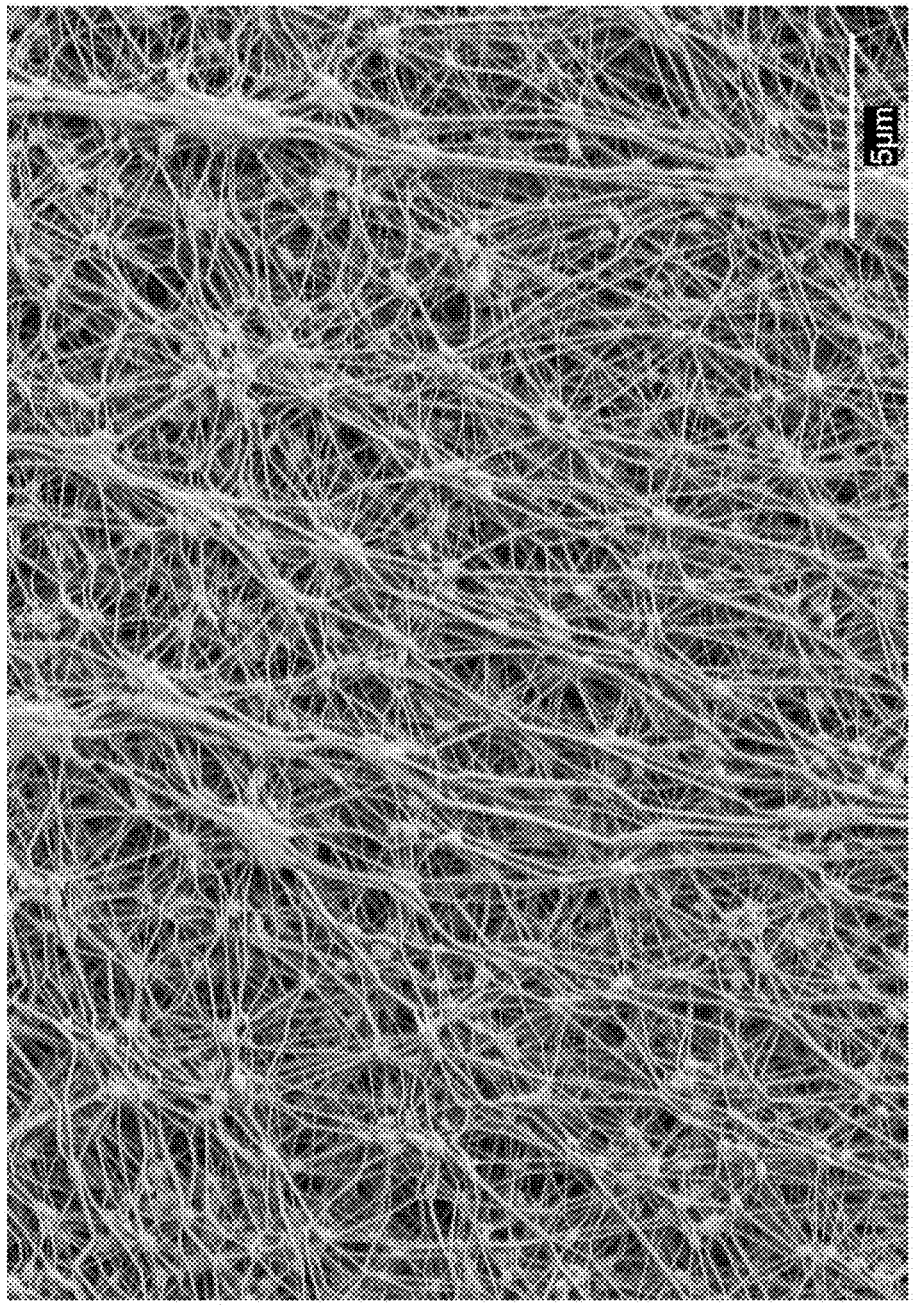
FIGS. 7A, 7B and 7C are scanning electron micrograph images of expanded fluoropolymer membranes used to form the valve leaflets, in accordance with an embodiment.

The expanded fluoropolymer of the present embodiments may comprise any suitable microstructure for achieving the desired leaflet performance. In one embodiment, the expanded fluoropolymer may comprise a microstructure of nodes interconnected by fibrils, such as described in U.S. Pat. No. 3,953,566 to Gore. In one embodiment, the microstructure of an expanded fluoropolymer membrane comprises nodes interconnected by fibrils as shown in the scanning electron micrograph image in FIG. 7A. The fibrils extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

Figure 7B:
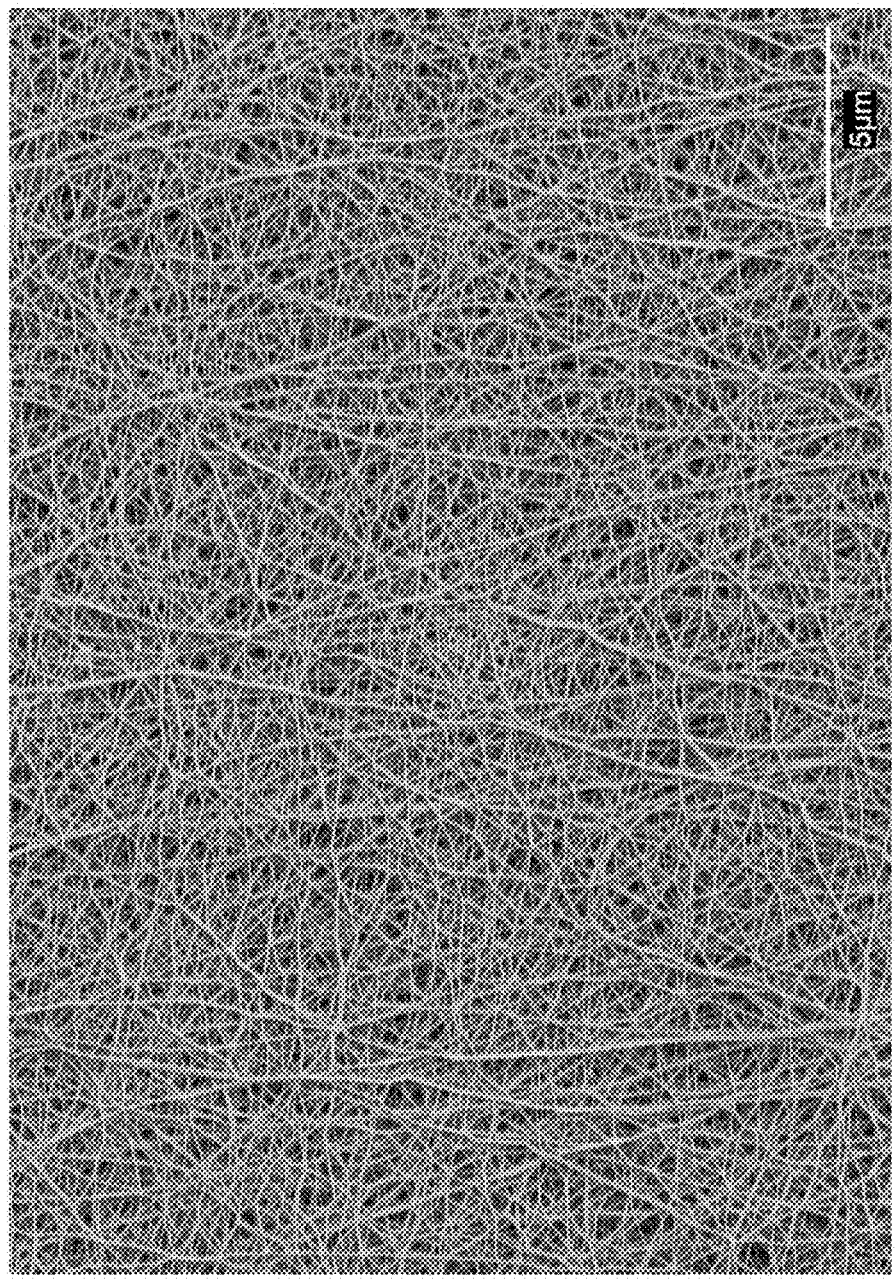
Figure 7C:
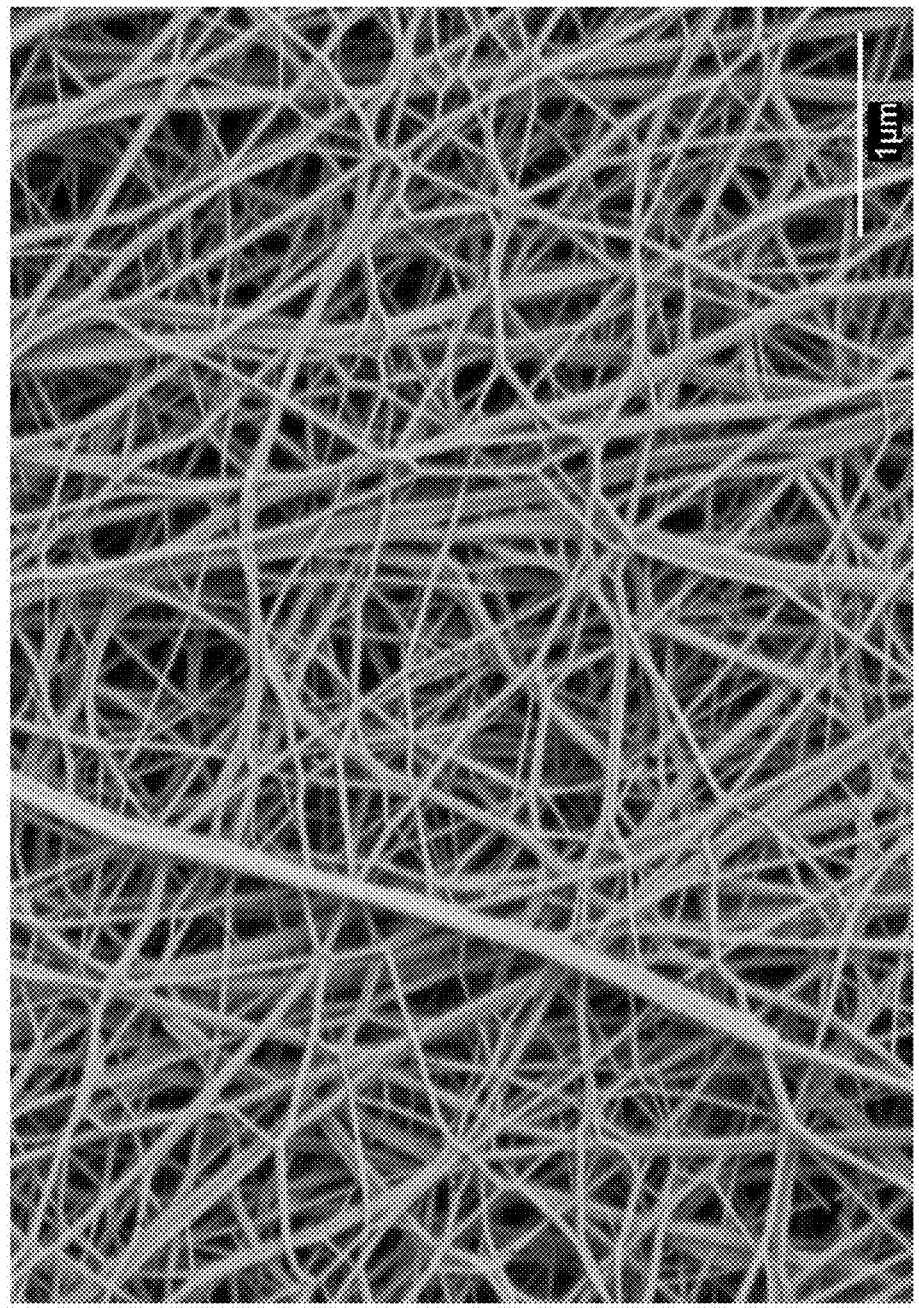

In another embodiment, the expanded fluoropolymer may have a microstructure of substantially only fibrils, such as, for example, depicted in FIGS. 7B and 7C, as is generally taught by U.S. Pat. No. 7,306,729, to Bacino. FIG. 7C is a higher magnification of the expanded fluoropolymer membrane shown in FIG. 7B, and more clearly shows the homogeneous microstructure having substantially only fibrils. The expanded fluoropolymer membrane having substantially only fibrils as depicted in FIGS. 7B and 7C, may possess a high surface area, such as greater than 20 m$^2$/g, or greater than 25 m$^2$/g, and in some embodiments may provide a highly balanced strength material having a product of matrix tensile strengths in two orthogonal directions of at least 1.5×10$^5$ MPa$^2$, and/or a ratio of matrix tensile strengths in two orthogonal directions of less than 2, and possibly less than 1.5.

The expanded fluoropolymer of the present embodiments may be tailored to have any suitable thickness and mass to achieve the desired leaflet performance. In some cases, it may be desirable to use a very thin expanded fluoropolymer membrane having a thickness less than 1.0 μm. In other embodiments, it may be desirable to use an expanded fluoropolymer membrane having a thickness greater than 0.1 μm and less than 20 μm. The expanded fluoropolymer membranes can possess a specific mass less than about 1 g/m$^2$ to greater than about 50 g/m$^2$.

Membranes according to embodiments can have matrix tensile strengths ranging from about 50 MPa to about 400 MPa or greater, based on a density of about 2.2 g/cm$^3$ for PTFE.

Additional materials may be incorporated into the pores or within the material of the membranes or in between the layers of the membranes to enhance desired properties of the leaflet. Composites according to one embodiment can include fluoropolymer membranes having thicknesses ranging from about 500 μm to less than 0.3 μm.

The expanded fluoropolymer membrane combined with elastomer provides the elements of the present embodiments with the performance attributes required for use in high-cycle flexural implant applications, such as heart valve leaflets, in at least several significant ways. For example, the addition of the elastomer improves the fatigue performance of the leaflet by eliminating or reducing the stiffening observed with ePTFE-only materials. In addition, it reduces the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer substantially filling the pore volume or present in substantially all of the pores reduces the space in which foreign materials can be undesirably incorporated into the composite. An example of such foreign material is calcium. If calcium becomes incorporated into the composite material, as used in a heart valve leaflet, for example, mechanical damage can occur during cycling, thus leading to the formation of holes in the leaflet and degradation in hemodynamics.

In one embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675. As discussed above, the elastomer is combined with the expanded fluoropolymer membrane such that the elastomer occupies substantially all of the void space or pores within the expanded fluoropolymer membrane. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In another embodiment, a method of filling the pores of the expanded fluoropolymer membrane includes the steps of delivering the filler via a dispersion to partially or fully fill the pores of the expanded fluoropolymer membrane;

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675, and other references that would be known to those of skill in the art. For instance, in another embodiment shown in Example 1, a leaflet was formed from a composite of 53% by weight of elastomer to ePTFE and was subjected to cycle testing. Some stiffening was observed by around 200 million test cycles, though with only modest effect on hydrodynamics. When the weight percent of elastomer was raised to about 83% by weight, as in the embodiment of Example 2, no stiffening or negative changes in hydrodynamics were observed at about 200 million cycles. In contrast, with non-composite leaflets, i.e. all ePTFE with no elastomer, as in the Comparative Example B, severe stiffening was apparent by 40 million test cycles. As demonstrated by these examples, the durability of porous fluoropolymer members can be significantly increased by adding a relatively high-percentage of relatively lower strength elastomer to the pores of the fluoropolymer members. The high material strength of the fluoropolymer membranes also permits specific configurations to be very thin.

Other biocompatible polymers which may be suitable for use in embodiments may include but not be limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Leaflets constructed from a composite material comprising less than about 55% fluoropolymer by weight can be assembled in a variety of configurations based on desired laminate or leaflet thickness and number of layers of composite. The thickness of the composite is directly related to the percentage of fluoropolymer by weight and membrane thickness. Using a range of membrane thickness from about 300 nm to more than 3,556 nm and a range of percentage of fluoropolymer by weight from 10 to 55, for example, allowed the formation of composite thicknesses ranging from 0.32 µm to more than 13 µm.

Figure 37:
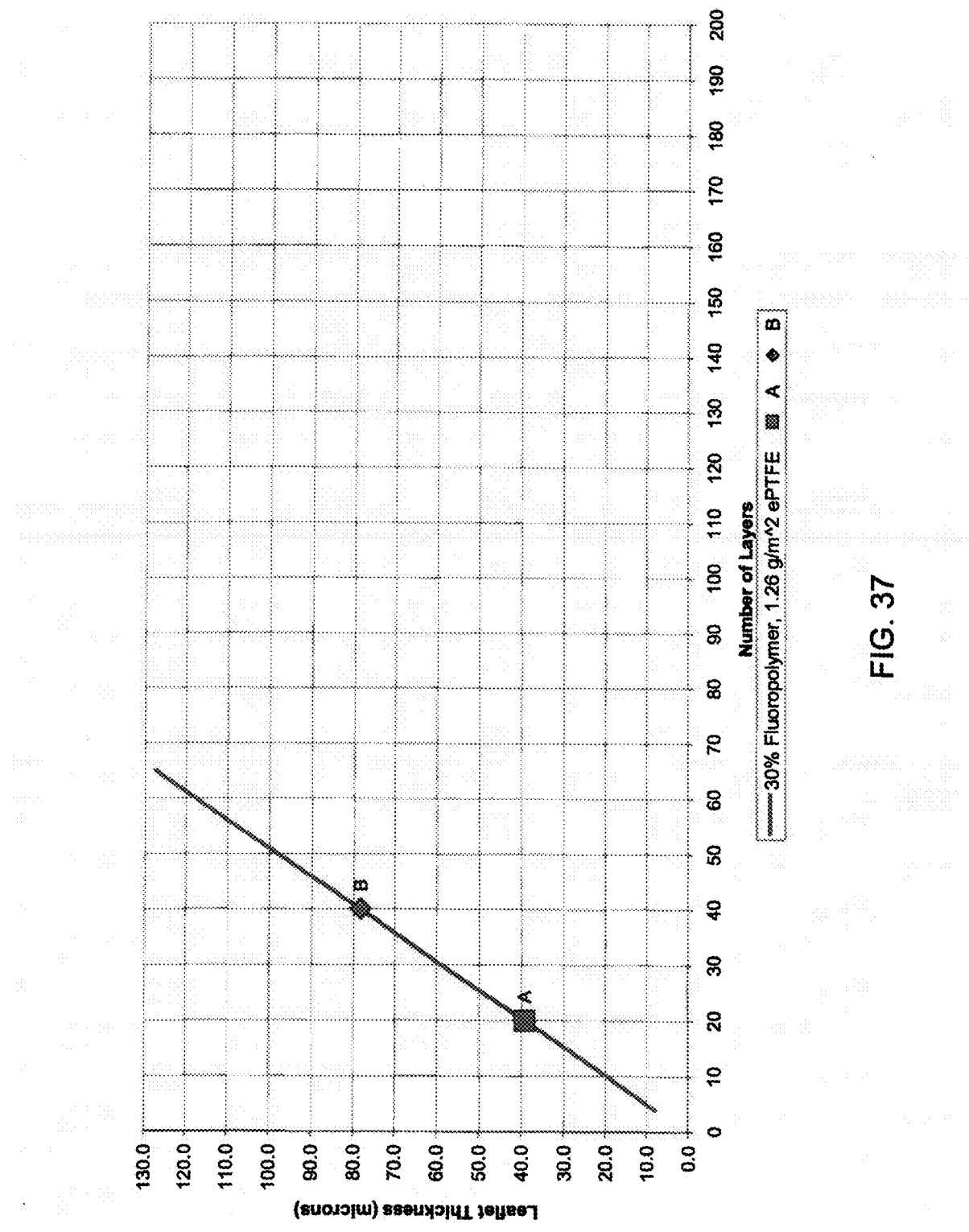
FIG. 37 is a graph of leaflet thickness and numbers of layers for a single composite material, in accordance with embodiments.

The relationship between the leaflet thickness and number of composite layers is shown illustratively in a graph in FIG. 37, wherein two leaflet configurations, indicated as A and B, are shown. In one embodiment, these configurations A and B may be constructed from a single composite. In another embodiment, there may be a generally linear relationship between leaflet thickness and number of layers, wherein $Y=mX$; in which Y=leaflet thickness, m=slope, and X=number of layers. The slope (m) or ratio of leaflet thickness to number of layers is equal to the composite thickness. Therefore, doubling the number of layers from 20 to 40 for configurations A and B, for example, has the result of doubling the thickness from 40 µm to 80 µm. It should be appreciated that the slope of the line or even the shape of the graph of leaflet thickness versus number of composite layers can vary depending on the amount of elastomer between the layers and the uniformity of the layers.

Figure 38:
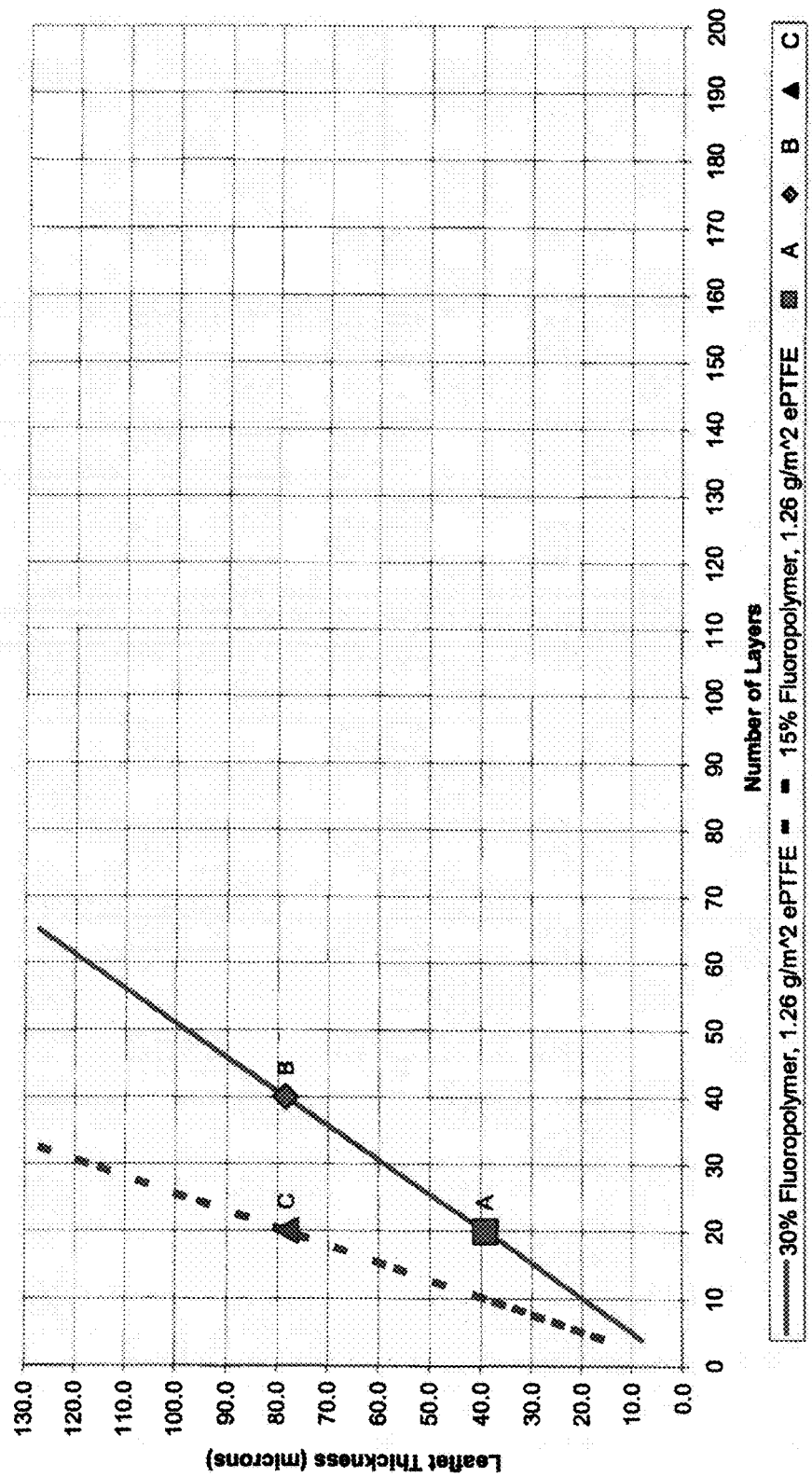
FIG. 38 is a graph comparing the leaflet thickness and numbers of layers for two different composite materials, in accordance with embodiments.

When the percentage of fluoropolymer by weight for the same membrane is reduced, the thickness of the composite is increased. As shown in FIG. 38, this increase in composite thickness is indicated by the increased slope of the dotted line relative to the solid line from the previous embodiment. In the embodiment illustrated by the dotted line, a reduction of the percentage of fluoropolymer by weight for the same membrane by about half results in about an increase in thickness of the composite by about two, which is reflected in the increased slope of the dotted line. Therefore, a leaflet as depicted by configuration C in FIG. 38 can either have the same number of layers as configuration A or the same leaflet thickness as configuration B by varying the percentage of fluoropolymer by weight.

Figure 39:
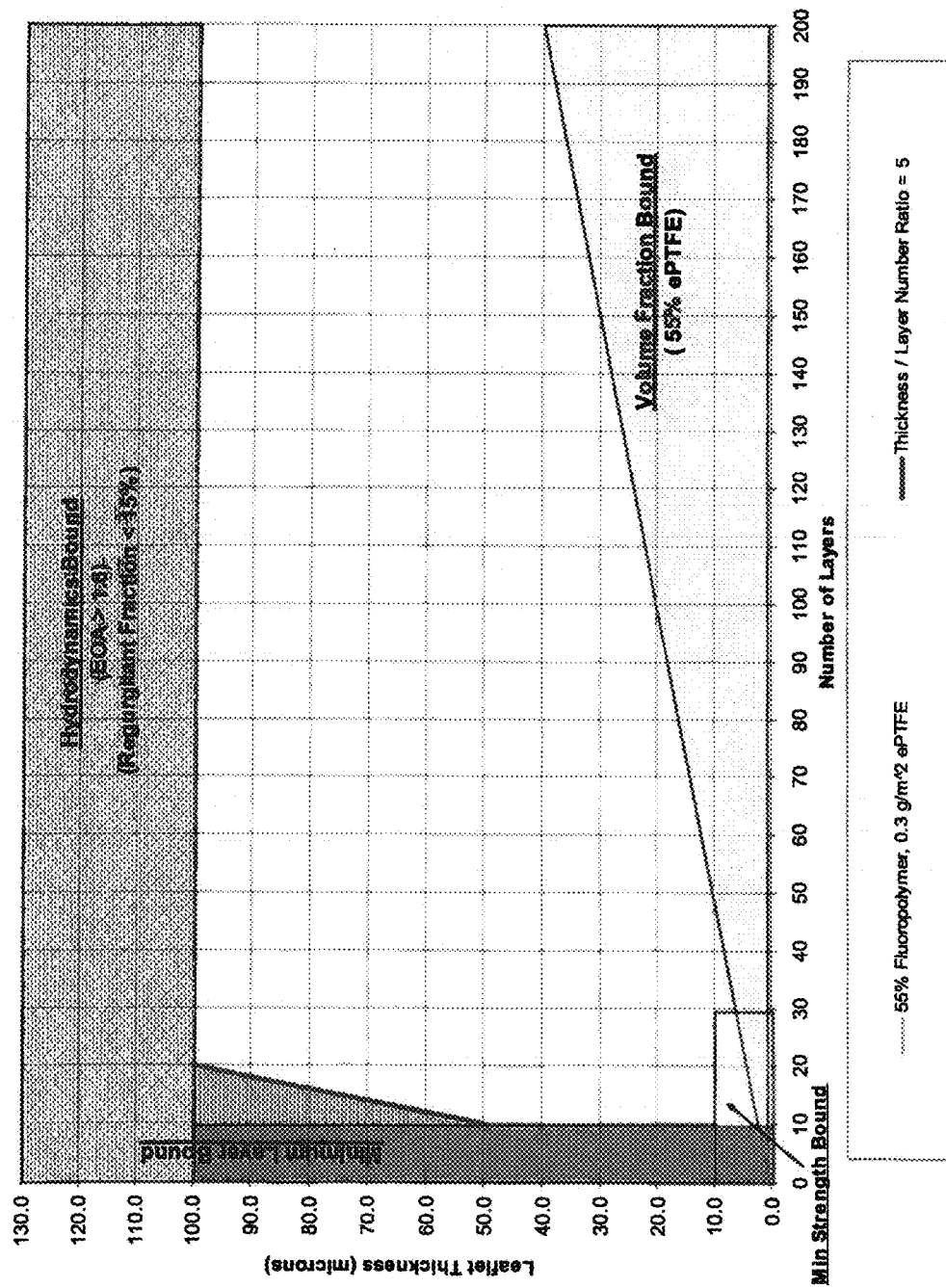
FIG. 39 is a sample graph of leaflet thickness and number of layers with boundaries defined for hydrodynamic performance, minimum number of layers, minimum strength, maximum composite thickness, and maximum percentage of fluoropolymer, in accordance with embodiments.
Figure 40:
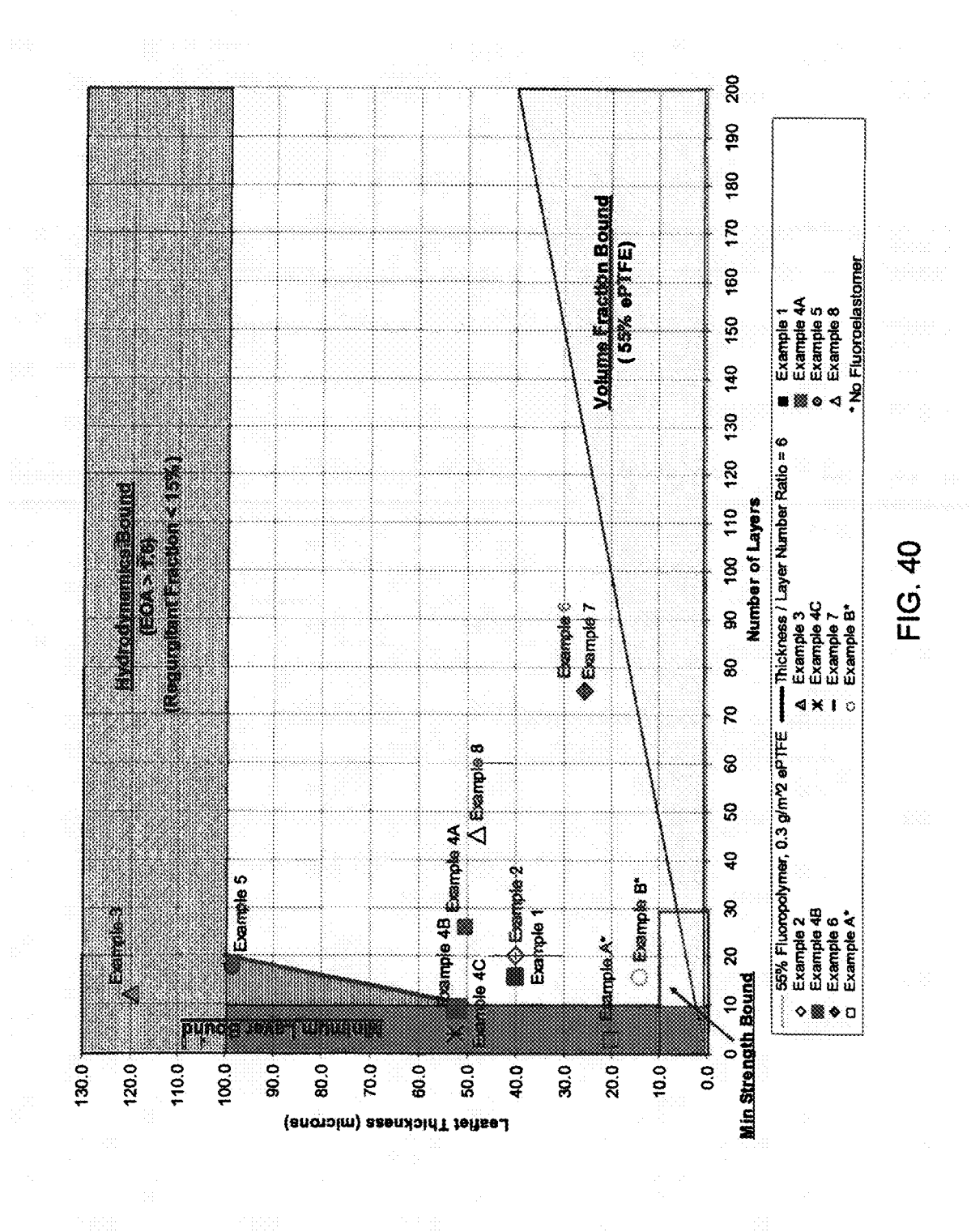
FIG. 40 is a graph of leaflet thickness and number of layers with boundaries defined for hydrodynamic performance, minimum number of layers, minimum strength, maximum composite thickness, and maximum percentage of fluoropolymer for the leaflet configurations of Examples 1, 2, 3, A, B, 4A, 4B, 4C, 5, 6, 7, & 8, in accordance with embodiments.

In determining what configurations of percent fluoropolymer by weight, composite thickness, and number of layers influenced both hydrodynamic as well as durability performance, boundaries were observed, as best shown by the graph in FIG. 39. There are five boundaries that generally define suitable leaflet configurations that have been observed thus far. The first boundary is defined by acceptable hydrodynamic performance set forth by ISO guidance document for cardiovascular implants (5840:2005) defining limits of EOA and regurgitant fraction for a given valve size. Typically, leaflets with a thickness greater than 100 μm formed from these composites perform near these limits of acceptability. The second boundary is a minimum number of layers (10) as observed by durability failures further illustrated by the examples provided. Similarly, the third boundary is a maximum ratio of leaflet thickness to number of layers or composite thickness of 5 μm. Generally, low layer numbers built from thick composites performed poorly when compared to high layer numbers of either the same percent fluoropolymer by weight and leaflet thickness. The fourth boundary is defined by the minimum number of layers of a given composite which is determined by the strength required to resist fluoropolymer creep during hydrodynamic loading of the leaflet when the valve is closed during the cardiac cycle. The strength of the laminate is measured by a dome burst test, where typically a burst pressure of least 207 KPa is required to ensure the leaflets maintain their shape and function. The fifth boundary is defined by the maximum percent fluoropolymer by weight (55%) required to significantly increase cyclic durability. In FIG. 40, a graph illustrating these boundaries is shown with the leaflet configurations of all the examples provided to further illustrate these discoveries.

Figure 42:
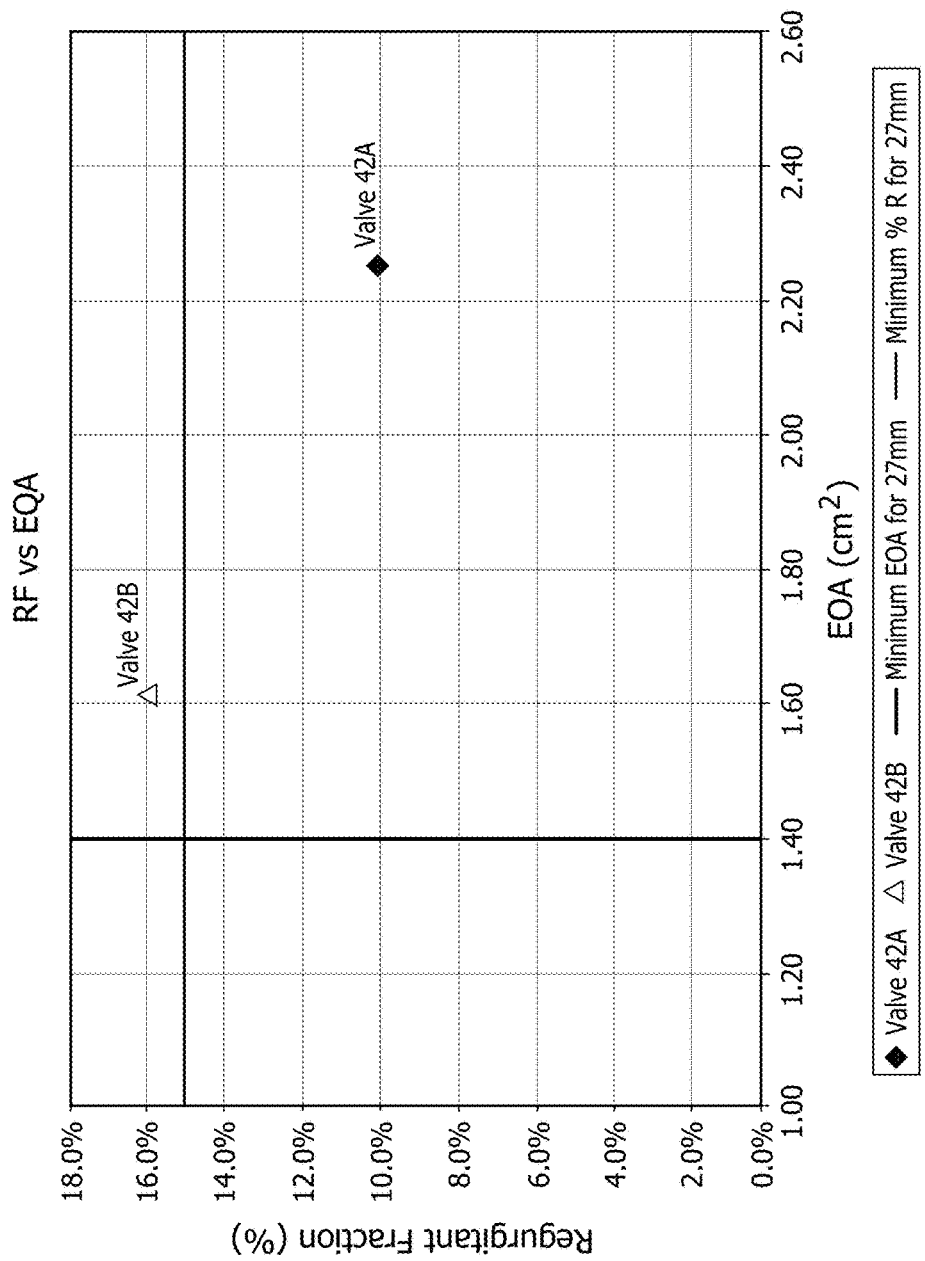
FIG. 42 is a graph of hydrodynamic performance data (EOA and regurgitant fraction) comparing two valves, in accordance with embodiments.

The maximum number of layers of a given composite may be determined by the desired leaflet thickness. It has been observed that as leaflet thickness increases, the hydrodynamic performance behavior for a given valve geometry decreases while the bending character improves. "Hydrodynamic performance" generally refers to the combination of EOA and regurgitant fraction plotted on a Cartesian coordinate system in two dimensions for a given valve size as depicted in FIG. 42. "Bending character" generally refers to the qualitative amount of wrinkles and/or creases developed with in the leaflet structure during deformations induced by cyclic opening and closing. Conversely, as leaflet thickness is decreased, the hydrodynamic performance behavior for a given geometry increases while the bending character is reduced. This observation of differences in bending character as a function of leaflet thickness is further illustrated with examples of two valves with 13 μm and 130 μm leaflet thicknesses, referred to as valve 42A and valve 42B, respectively. A graph of hydrodynamic performance data (EOA and regurgitant fraction) comparing these two valves is shown in FIG. 42 where minimizing the regurgitant fraction and maximizing the EOA is desirable.

It has been observed that thin film materials exposed to large cyclic deformations over long durations are generally susceptible to wrinkles and creases. It is also generally known by those skilled in the art that durability of thin materials exposed to large cyclic deformations over long durations is reduced as a result of such wrinkles and creases that can be formed during the duty cycle.

Therefore, it was surprising when leaflets of similar thickness (about 16 μm) which were constructed from ultra thin composites (0.32 μm) and had five times the number of layers (about 50) versus conventional leaflets had the desirable bending behavior only previously achieved by leaflets having thicknesses of 75 μm or greater. Additionally, when comparing durability of low number of layers of composites to high number of layers, the high number of layers typically out-perform the low number of layers constructs by orders of magnitude using number of duty cycles as a comparison.

A valve with fifty layers and 16 μm thick leaflets was shown to have significantly fewer wrinkles and creases than a six layer construction of the approximately the same thickness.

Comparing leaflets of about the same thickness in cross section with 4, 9, 26, 50, & 21 layers respectively, it was appreciated that the increase in the number of layers facilitates both the ability of the laminate to take a smaller bend radius as well as accommodate a tight curvature by storing length of individual layers through localized buckling.

Figure 41A:
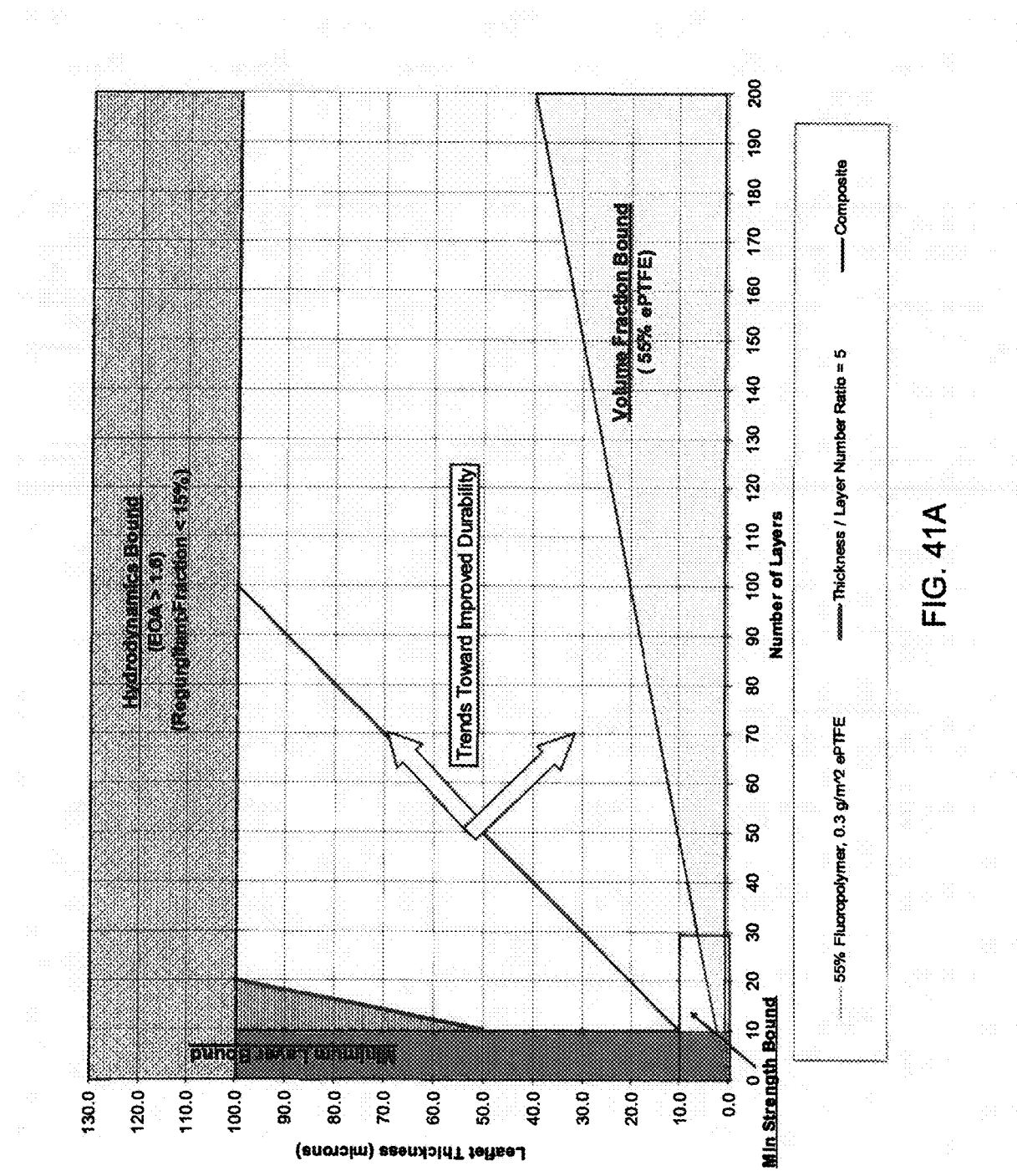
FIG. 41A is a graph of leaflet thickness and number of layers depicting general trends of improved durability observed during accelerated wear testing.
Figure 41B:
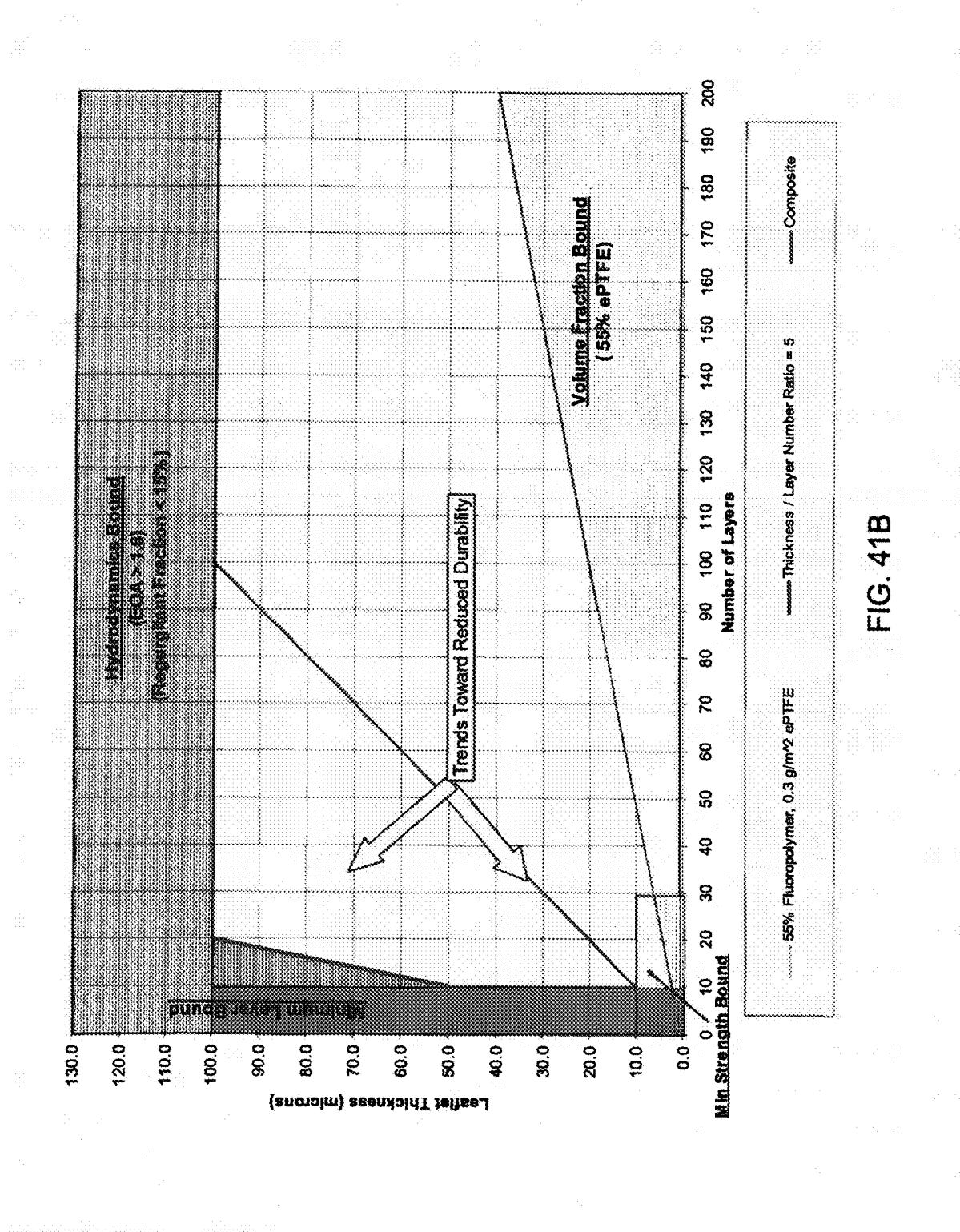
FIG. 41B is a graph of leaflet thickness and number of layers depicting general trends of reduced durability observed during accelerated wear testing.

General trends that have been observed by varying the thickness and number of layers are illustrated in the graphs in FIGS. 41A and 41B and are further supported by the examples provided.

The following non-limiting examples are provided to further illustrate embodiments. It should also be readily appreciated that other valve frame designs may be used other than those illustrated in the examples below and accompanying figures.

Example 1

Figure 2A:
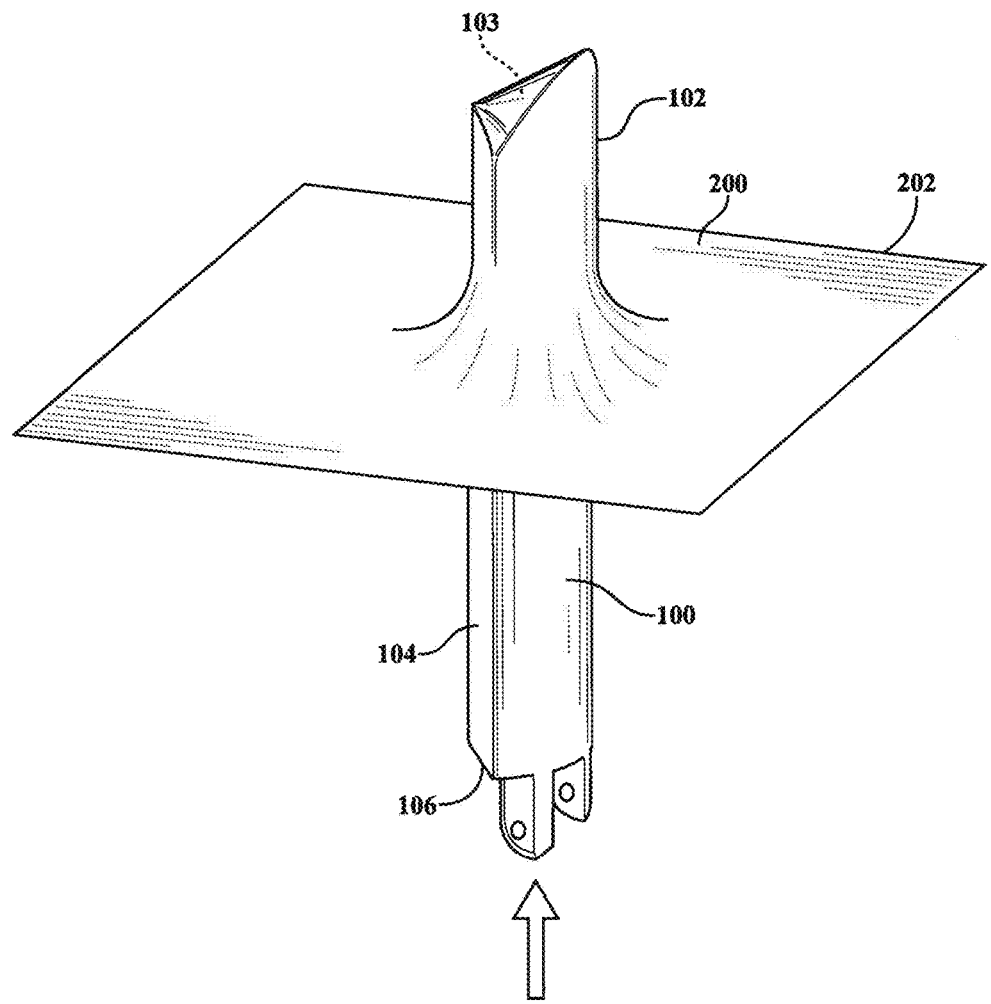
FIG. 2A is a perspective view of a cushion pad being stretched over a leaflet tool, in accordance with an embodiment.

Heart valve leaflets according to one embodiment were formed from a composite material having an expanded fluoropolymer membrane and an elastomeric material and joined to a metallic balloon expandable stent using an intermediate layer of FEP, as described by the following process:

1) A thick, sacrificial tooling cushion pad or layer was formed by folding a ePTFE layer over upon itself to create a total of four layers. The ePTFE layer was about 5 cm (2") wide, about 0.5 mm (0.02") thick and had a high degree of compressibility, forming a cushion pad. Referring to FIGS. 1 and 2, the cushion pad 200 was then stretched (FIG. 2) onto a leaflet tool, generally indicated at 100. The leaflet tool 100 has a leaflet portion 102, a body portion 104 and a bottom end 106. The leaflet portion 102 of the leaflet tool 100 has a generally arcuate, convex end surface 103. The cushion pad 200 was stretched and smoothed over the end surface 103 of the leaflet portion 102 of the leaflet tool 100 by forcing the leaflet tool 100 in the direction depicted by the arrow (FIG. 2A). A peripheral edge 202 of the cushion pad 200 was stretched over the bottom end 106 of the leaflet tool 100 and twisted to hold the cushion pad 200 in place (FIG. 2B).

Figure 2B:
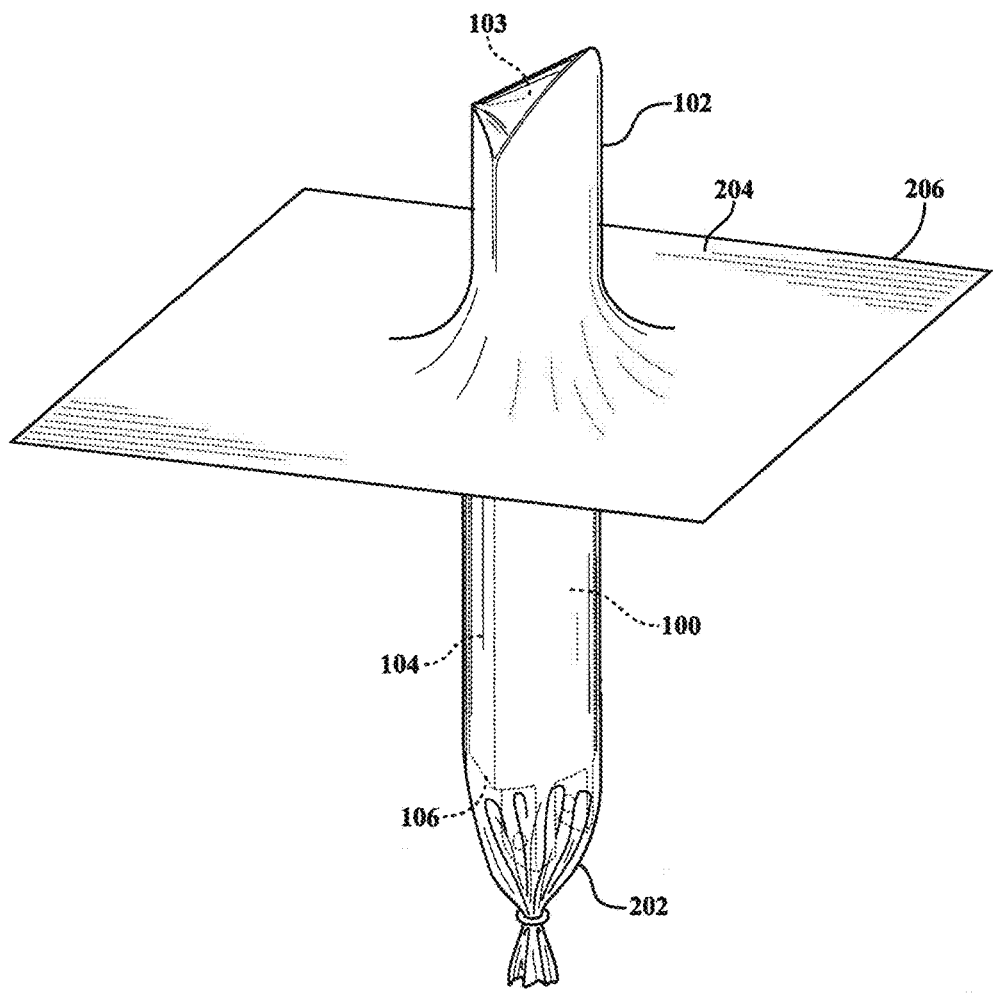
FIG. 2B is a perspective view of a release layer being stretched over the cushion pad covered leaflet tool in FIG. 2A, in accordance with an embodiment.

2) Referring to FIG. 2B, a release layer 204 was then stretched over the leaflet portion 102 of the leaflet tool 100 which in the previous step was covered with the cushion pad 200. In one embodiment, the release layer 204 was made from a substantially nonporous ePTFE having a layer of fluorinated ethylene propylene (FEP) disposed along an outer surface or side thereof. The release layer 204 was stretched over the leaflet tool 100 such that the FEP layer faced toward the cushion pad 200 and the substantially nonporous ePTFE faced outwardly or away from the cushion pad 200. The release layer was about 25 μm thick and of sufficient length and width to allow the release layer 204 to be pulled over the bottom end 106 of the leaflet tool 100. As with the cushion pad 200 in the previous step, a peripheral edge 206 of the release layer 204 was pulled toward the bottom end 106 of the leaflet tool 100 and then twisted onto the bottom end 106 of the leaflet tool 100 to retain or hold the release layer 204 in place. The FEP layer of the release layer 204 was then spot-melted and thereby fixedly secured to the cushion pad 200, as required, by the use of a hot soldering iron.

3) The processes of Steps 1) and 2) were repeated to prepare three separate leaflet tools, each having a cushion pad covered by a release layer.

4) A leaflet material according to one embodiment was formed from a composite material comprising a membrane of ePTFE imbibed with a fluoroelastomer. A piece of the composite material approximately 10 cm wide was wrapped onto a circular mandrel to form a tube. The composite material was comprised of three layers: two outer layers of ePTFE and an inner layer of a fluoroelastomer disposed therebetween. The ePTFE membrane was manufactured according to the general teachings described in U.S. Pat. No. 7,306,729. The fluoroelastomer was formulated according to the general teachings described in U.S. Pat. No. 7,462,675. Additional fluoroelastomers may be suitable and are described in U.S. Publication No. 2004/0024448.

The ePTFE membrane had the following properties: thickness=about 15 μm; MTS in the highest strength direction=about 400 MPa; MTS strength in the orthogonal direction=about 250 MPa; Density=about 0.34 g/cm$^3$; IBP=about 660 KPa.

The copolymer consists essentially of between about 65 and 70 weight percent perfluoromethyl vinyl ether and complementally about 35 and 30 weight percent tetrafluoroethylene.

The percent weight of the fluoroelastomer relative to the ePTFE was about 53%.

The multi-layered composite had the following properties: thickness of about 40 μm; density of about 1.2 g/cm$^3$; force to break/width in the highest strength direction=about 0.953 kg/cm; tensile strength in the highest strength direction=about 23.5 MPa (3,400 psi); force to break/width in the orthogonal direction=about 0.87 kg/cm; tensile strength in the orthogonal direction=about 21.4 MPa (3100 psi), IPA bubble point greater than about 12.3 MPa, Gurley Number greater than about 1,800 seconds, and mass/area=about 14 g/m$^2$.

The following test methods were used to characterize the ePTFE layers and the multi-layered composite.

The thickness was measured with a Mutitoyo Snap Gage Absolute, 12.7 mm (0.50") diameter foot, Model ID-C112E, Serial #10299, made in Japan. The density was determined by a weight/volume calculation using an Analytical Balance Mettler PM400 New Jersey, USA. The force to break and tensile strengths were measured using an Instron Model #5500R Norwood, Mass., load cell 50 kg, gage length=25.4 cm, crosshead speed=25 mm/minute (strain rate=100% per minute) with flat faced jaws. The IPA Bubble Point was measured by an IPA bubble point tester, Pressure Regulator Industrial Data Systems Model LG-APOK, Salt Lake City, Utah, USA, with a Ramp Rate of 1.38 KPa/s (0.2 psi/s), 3.14 cm$^2$ test area. The Gurley Number was determined as the time in seconds for 100 cm$^3$ of air to flow through a 6.45 cm$^2$ sample at 124 mm of water pressure using a Gurley Tester, Model #4110, Troy, N.Y., USA.

Unless otherwise noted, these test methods were used to generate the data in subsequent examples.

Layers of the composite material, each having two outer layers of ePTFE and an inner layer of a fluoroelastomer disposed therebetween, was wrapped onto a mandrel having a diameter of about 28 mm (1.1") such that the higher strength direction of the membrane was oriented in the axial direction of the mandrel. In one embodiment, four layers of the composite material were wrapped in a non-helical, generally circumferential fashion onto the mandrel. The composite material had a slight degree of tackiness that allowed the material to adhere to itself. While still on the mandrel, the composite material was slit longitudinally generally along the mandrel long axis to form a sheet about 10 cm (4") by about 90 mm (3.5").

5) The resulting sheet of leaflet material (or composite material from Step 4) was then cut and wrapped onto the leaflet tool 100 having a cushion pad 200 covered by a release layer 204. More specifically, as shown in FIGS. 3A-3C, the leaflet material 300 was placed onto a flat cutting surface. The leaflet tool 100 with the cushion pad 200 and release layer 204 was then aligned onto the leaflet material 300 approximately as shown. Four slits 302, 304, 306, 308 were then formed in the leaflet material 300 with a razor blade. One pair of slits 302, 304 extends from one side of the leaflet tool 100 and terminates at one edge 300a of the leaflet material 300, and the other pair of slits 306, 308 extends from an opposite side of the leaflet tool 100 and terminates at an opposite edge 300b of the leaflet material 300. The slits 302, 304, 306, 308 were spaced apart from the leaflet portion 102 of the leaflet tool 100. The slits 302, 304, 306, 308 did not protrude under the leaflet tool 100. It should be appreciated that the widths of the individual slits are shown not to scale. The slits 302, 304, 306, 308 in the leaflet material 300 resulted in the formation of a folding portion 310, a pair of straps 312, 314 and excess material of leaflet material 315. The folding portions 310 were then folded in the general direction indicated by the arrows 316 in FIG. 3 and smoothed over the leaflet tool 100, which was covered by the cushion pad 200 and the release layer 204 in the previous steps.

6) The leaflet material 315 was then stretched and smoothed over the leaflet portion 102, particularly the end surface 103 of the leaflet tool 100. The Steps 4) and 5) were repeated to form three separate leaflet assemblies. The three leaflet assemblies 402, 404, 406 were then clamped together to form a tri-leaflet assembly 400, as shown in FIG. 4. Shown are the three separate leaflet assemblies 402, 404, 406, each having an excess material of leaflet material 315 extending generally radially beyond the periphery of the tri-leaflet assembly 400.

7) A base tool was then provided having cavities for engaging the end surfaces of the leaflet tools of the tri-leaflet assembly and trimming the excess leaflet area to form three leaflets. Referring to FIG. 5A, the base tool is generally indicated at 500 and extends longitudinally between an end 501 and an opposite bottom end 503. Three concave cavities 502, 504, 506 are formed in the end 501 of the base tool 500. Each concave cavity 502, 504, 506 is formed to match fit or nestingly seat the end surface 103 of one of the three leaflet assemblies 402, 404, 406. Three radially extending elements 508, 510, 512 extend outwardly from the end of the base tool 500. Each element 508, 510, 512 is disposed between an adjacent pair of concave cavities 502, 504, 506.

The base tool 500 was then prepared having a compression pad and a release layer (not shown) similar to how the leaflet tool was prepared in Steps 1 and 2. As described for each leaflet tool in Steps 1 and 2, the compression pad and the release layer were similarly stretched and affixed to the base tool 500 to form a base tool assembly.

8) Referring to FIG. 5B, the base tool assembly (illustrated for convenience as the base tool 500 without showing the cushion pad and the release layer) and the tri-leaflet assembly, generally indicated at 400, were then generally axially aligned together so that the end surface (not shown) of each leaflet tool 100 was seated into one of the concave cavities (not shown) in the end 501 of the base tool, generally indicated at 500, to form a combined tool assembly.

9) A metallic balloon expandable stent was then fabricated. A tube of 316 stainless steel having a wall thickness of about 0.5 mm (0.020") and a diameter of about 2.5 cm (1.0") was laser cut. A pattern was cut into the tube to form an annular-shaped cut stent frame or support structure, which is generally indicated at 600 and shown illustratively in a flat, plane view in FIG. 6a. The support structure 600, includes a plurality of small closed cells 602, a plurality of large closed cells 604, and a plurality of leaflet closed cells 606. Note that one of the plurality of leaflet closed cells 606 appears as an open cell in FIG. 6A due to the flat plane view. The cells 602, 604, 606 are generally arranged along rows forming the annular shape of the support structure 600.

10) Polymeric materials were then adhered to the laser cut stent frame. First, a sacrificial compression layer of ePTFE membrane was wrapped without overlap onto a mandrel (not shown) having a diameter of about 2.5 cm (1.0"). The sacrificial compression layer of ePTFE membrane had a thickness of about 0.5 mm (0.02") and a width of about 10 cm (4"), and was compliant and compressible to provide a soft, sacrificial compression layer.

11) Four layers of a substantially nonporous, ePTFE film were then wrapped onto the mandrel on top of the compression layer membrane. The substantially nonporous, ePTFE film had a thickness of about 25 μm (0.001"), was about 10 cm (4") wide and had a layer of FEP on one side. The substantially nonporous, ePTFE film was wrapped with the FEP facing away from the mandrel. The substantially nonporous, ePTFE film had the properties of the release layer previously described in Step 2).

12) A thin film of type 1 (ASTM D3368) FEP was constructed using melt extrusion and stretching. An additional 10 layers of this type 1 (ASTM D3368) FEP film was added to the mandrel, which was previously wrapped in the compression layer membrane in Step 10 and the four layers of substantially nonporous, ePTFE film in Step 11. The type 1 (ASTM D3368) FEP film was about 40 μm (0.0016") thick and was about 7.7 cm (3") wide.

13) The wrapped mandrel was then heat treated in an air convection oven at about 320° C. for about 5 minutes and allowed to cool.

14) The support structure (indicated at 600 in FIG. 6A) was then placed onto the heat treated and wrapped mandrel. Two additional layers of type 1 (ASTM D3368) FEP film (provided in Step 12) were then wrapped onto the support structure, which was previously placed on the wrapped mandrel.

15) The wrapped mandrel and the support structure supported thereon were then heat treated in an air convection oven at about 320° C. for about 10 minutes and allowed to cool, forming a polymeric-coated support structure.

Figure 6A:
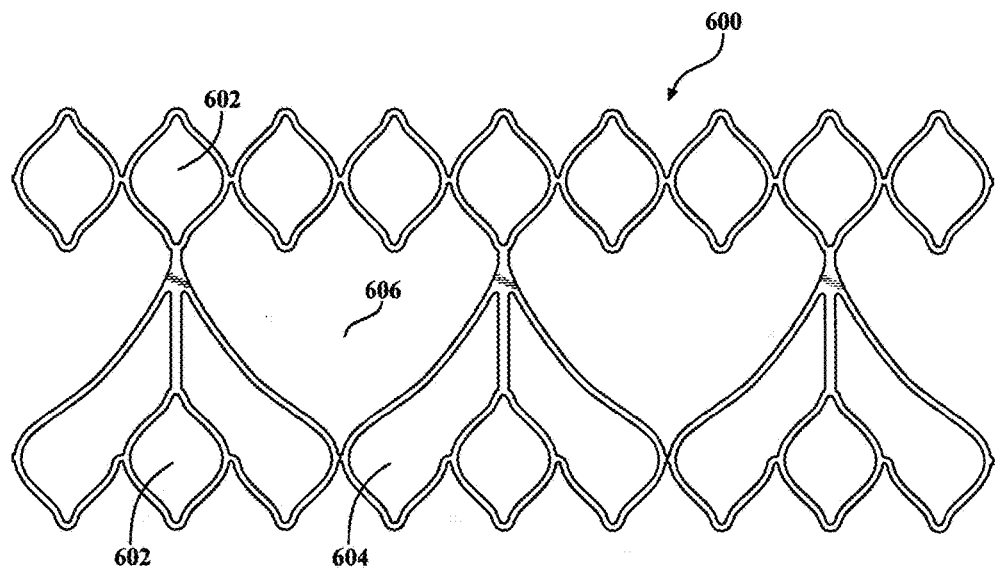
FIG. 6A is a flattened plane view of a stent frame or support structure, in accordance with an embodiment.
Figure 6B:
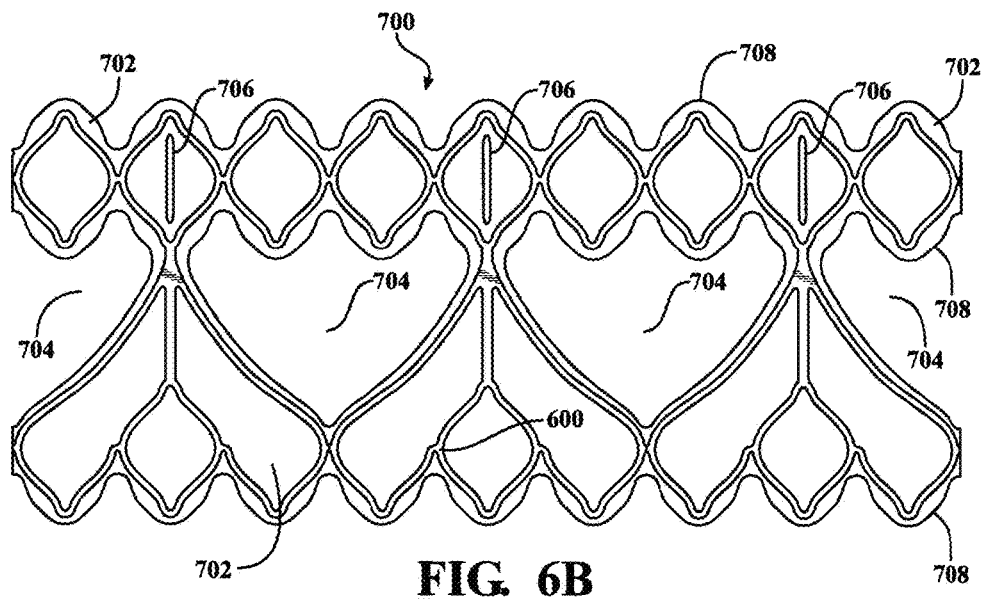
FIG. 6B is a flattened plane view of the support structure covered in a polymer coating, in accordance with an embodiment.

16) The polymeric-coated support structure was then trimmed with a scalpel to form a trimmed stent frame, which is generally indicated at 700 and shown illustratively in a flat, plane view in FIG. 6B. More specifically, in one manner, the polymeric coating was trimmed about 2 mm (0.08") past the edges of the support structure (600, FIG. 6A) to form a variety of edge profiles 708. In another manner, the polymeric coating was allowed to span entire cells to form a web in each cell. In either case, the support structure 600 was fully encapsulated within a polymeric coating 702 to form the trimmed stent frame 700. The trimmed stent frame 700 includes a plurality of leaflet openings 704 corresponding in number and generally in shape to the plurality of leaflet closed cells 606 (FIG. 6A). Further, a slit 706 is formed in the polymeric coating 702 of each of the small closed cells as shown in FIG. 6B. Specifically, each slit 706 is linear and generally parallel to a longitudinal center axis (not shown) of the annular-shaped support structure 600.

17) The trimmed stent frame was then placed onto the combined tool assembly from Step 8. The leaflet portions (102) of the leaflet tools were aligned to the leaflet openings (704 in FIG. 6B) in the trimmed stent frame. The three excess leaflet material areas (315 in FIG. 4) were pulled through the leaflet openings of the stent frame. Each of the three pairs of straps (312, 314 in FIG. 3A) was pulled through one of the slits (706 in FIG. 6B) and wrapped around the trimmed stent frame. Each pair of straps were wrapped in opposing directions relative to each other. The six straps were then heat tacked to the trimmed stent frame using a hot soldering iron.

18) The combined tool assembly (Step 8) and the trimmed stent frame having the wrapped and heat tacked straps were then mounted into a rotary chuck mechanism. The rotary chuck mechanism was then adjusted to apply a light, longitudinal compressive load. The excess leaflet material areas (315 in FIG. 4) were then heat tacked to the base tool (500 in FIG. 5) using a hot soldering iron.

19) The combined tools of Step 18 were then wrapped with an additional 2 layers of type 1 (ASTM D3368) FEP film (from Step 12). Three additional layers of the composite (Step 4) were then overwrapped and tacked down to the trimmed stent frame.

20) In preparation for a final heat treat, release and sacrificial layers of a compression tape and compression fiber were applied both circumferentially and longitudinally to the assembly from Step 19. The compression tape/fiber contact and compress the assembly both circumferentially and longitudinally during the subsequent heat treat. A sacrificial layer of compression tape was circumferentially wrapped in a helical fashion onto the assembly from Step 19. This compression tape had the properties of the sacrificial compression layer of ePTFE previously described in Step 10. An ePTFE compression fiber was then tightly wrapped onto the compression tape. Approximately 100 turns of the compression fiber were circumferentially applied in a closely spaced helical pattern. The ePTFE compression fiber was about 1 mm (0.04") in diameter and was structured to shrink longitudinally when sufficiently heated. The clamped assembly was then removed from the rotary chuck mechanism. Three layers of sacrificial compression tape were then wrapped in a longitudinal fashion around the assembly. Approximately 20 wraps of the compression fiber was then longitudinally wrapped over the longitudinal compression tape.

21) The assembly from Step 20 was then heat treated in an air convection oven at about 280° C. for about 90 minutes and then room temperature water quenched. This heat treatment step facilitates the flow of the thermoplastic fluoroelastomer into the pores of the ePTFE membrane used to create the leaflet material described in step 4.

Figure 8:
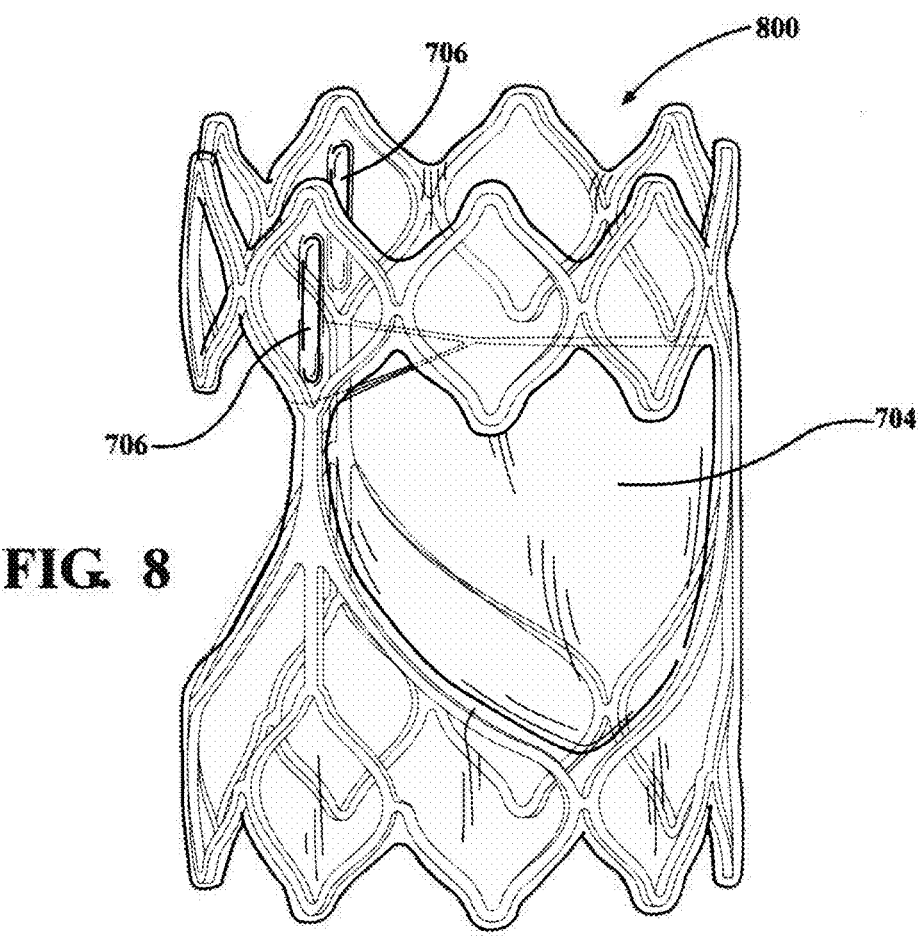
FIG. 8 is a perspective view of a valve assembly, in accordance with an embodiment.

22) The sacrificial compression tapes/fibers were then removed. The polymeric materials were trimmed to allow the leaflet and base tools to be separated. The stent polymeric layers were then trimmed to allow removal of the stent frame with the attached leaflets. The leaflets were then trimmed, resulting in a valve assembly as shown in FIG. 8 and generally indicated at 800.

Figure 9A:
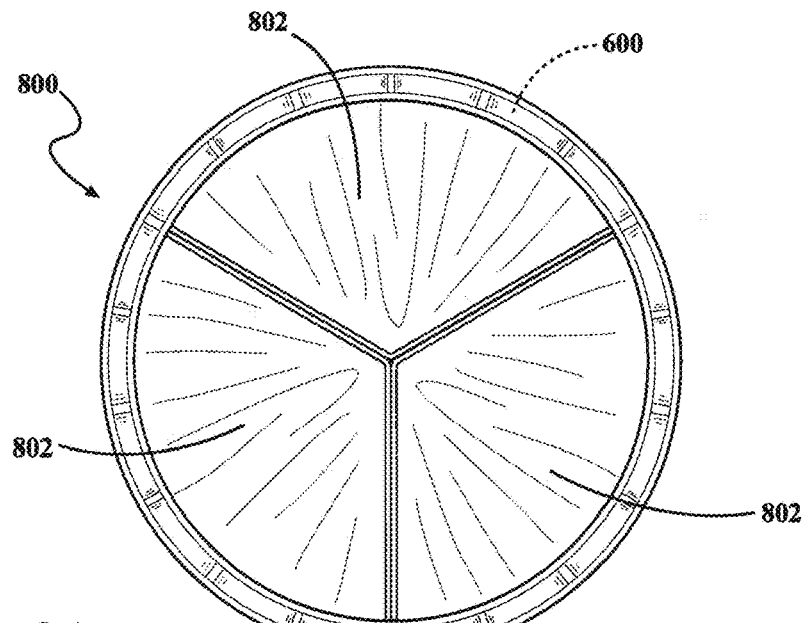
FIGS. 9A and 9B are top elevational views of the heart valve assembly of FIG. 8 shown illustratively in closed and open positions, respectively, in accordance with an embodiment.
Figure 9B:
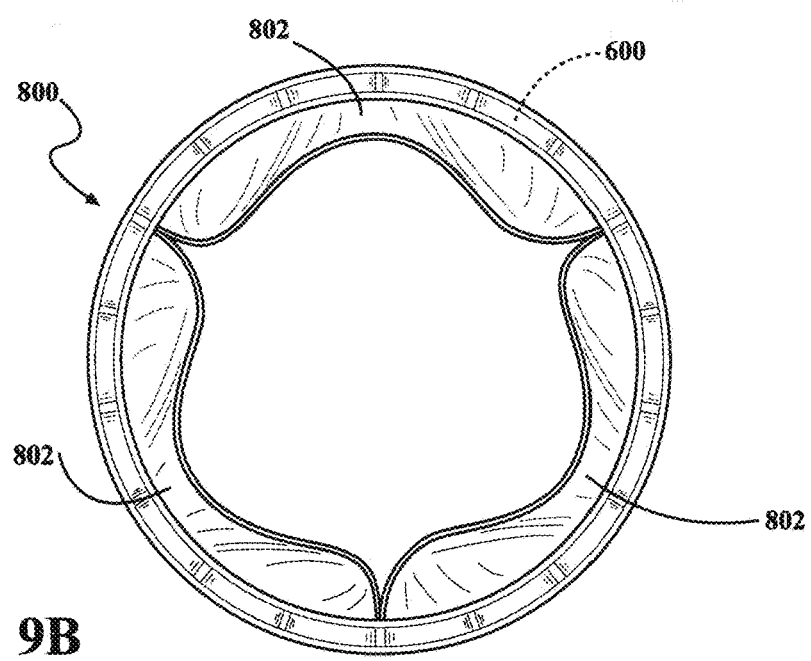

The resulting valve assembly 800, according to one embodiment, includes leaflets 802 formed from a composite material with at least one fluoropolymer layer having a plurality of pores and an elastomer present in substantially all of the pores of the at least one fluoropolymer layer. Each leaflet 802 is movable between a closed position, shown illustratively in FIG. 9A, in which blood is prevented from flowing through the valve assembly, and an open position, shown illustratively in FIG. 9B, in which blood is allowed to flow through the valve assembly. Thus, the leaflets 802 of the valve assembly 800 cycle between the closed and open positions generally to regulate blood flow direction in a human patient.

The performance of the valve leaflets in each valve assembly was characterized on a real-time pulse duplicator that measured typical anatomical pressures and flows across the valve, generating an initial or "zero fatigue" set of data for that particular valve assembly. The valve assembly was then transferred to a high-rate fatigue tester and was subjected to approximately 207 million cycles. After each block of about 100 million cycles, the valve was then returned to the real-time pulse duplicator and the performance parameters re-measured.

The flow performance was characterized by the following process:

1) The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada).

2) The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 $cm^2$ cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the valve under test.

3) The heart flow pulse duplicator system was adjusted to produce the desired flow, mean pressure, and simulated pulse rate. The valve under test was then cycled for about 5 to 20 minutes.

Figure 10:
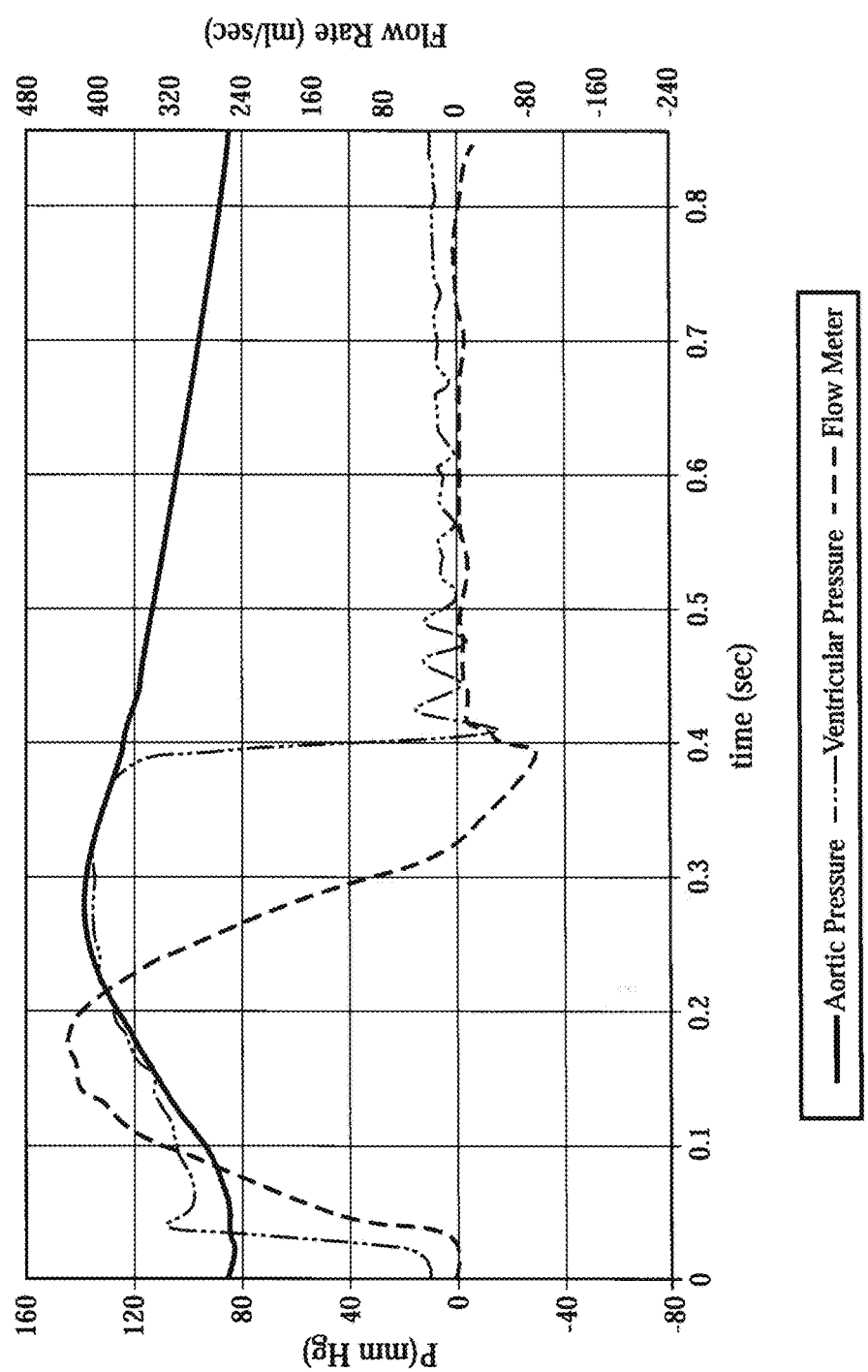
FIG. 10 is a graph of measured outputs from a heart flow pulse duplicator system used for measuring performance of the valve assemblies.

4) Pressure and flow data were measured and collected during the test period, including ventricular pressures, aortic pressures, flow rates, and pump piston position. Shown illustratively in FIG. 10 is a graph of typical data outputs from the heart flow pulse duplicator system.

5) Parameters used to characterize the valve and to compare to post-fatigue values are pressure drop across the open valve during the positive pressure portion of forward flow, effective orifice area, and regurgitant fraction.

Figure 11A:
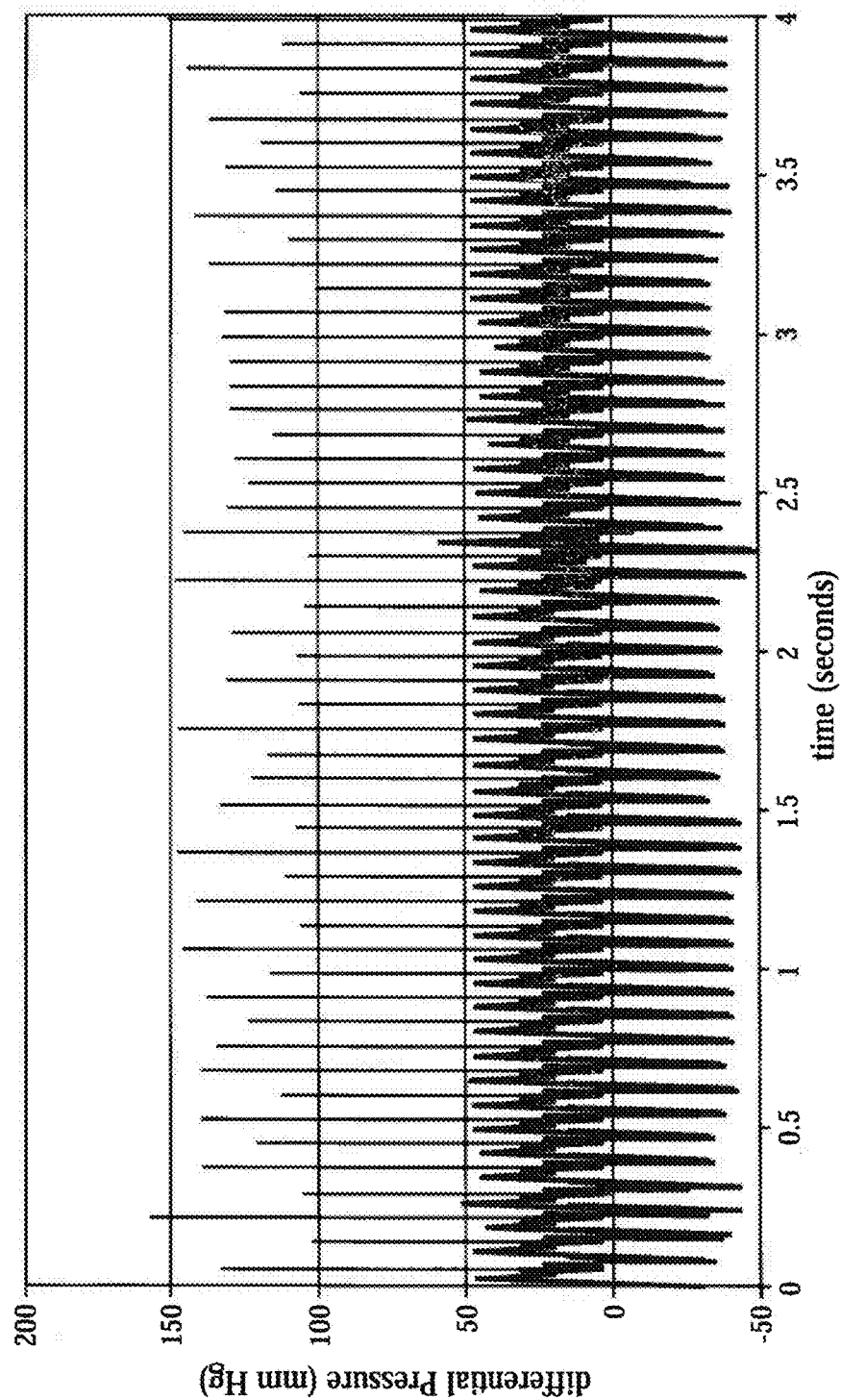

Following characterization, the valve assembly was then removed from the flow pulse duplicator system and placed into a high-rate fatigue tester. A Six Position Heart Valve Durability Tester, Part Number M6 was supplied by Dynatek, Galena, Mo., USA and was driven by a Dynatek Dalta DC 7000 Controller. This high rate fatigue tester displaces fluid through a valve assembly with a typical cycle rate of about 780 cycles per minute. During the test, the valve assembly can be visually examined using a tuned strobe light. The pressure drop across the closed valve can also be monitored as displayed in FIGS. 11A and 11B. Shown in FIGS. 11A and 11B is a typical data set verifying that the high-rate fatigue tester was producing consistent pressure wave forms.

The valve assembly was continuously cycled and periodically monitored for visual and pressure drop changes. After approximately 200 million cycles, the valve assembly was removed from the high-rate tester and returned to the real-time pulse duplicator. The pressure and flow data were collected and compared to the original data collected.

Figure 12A:
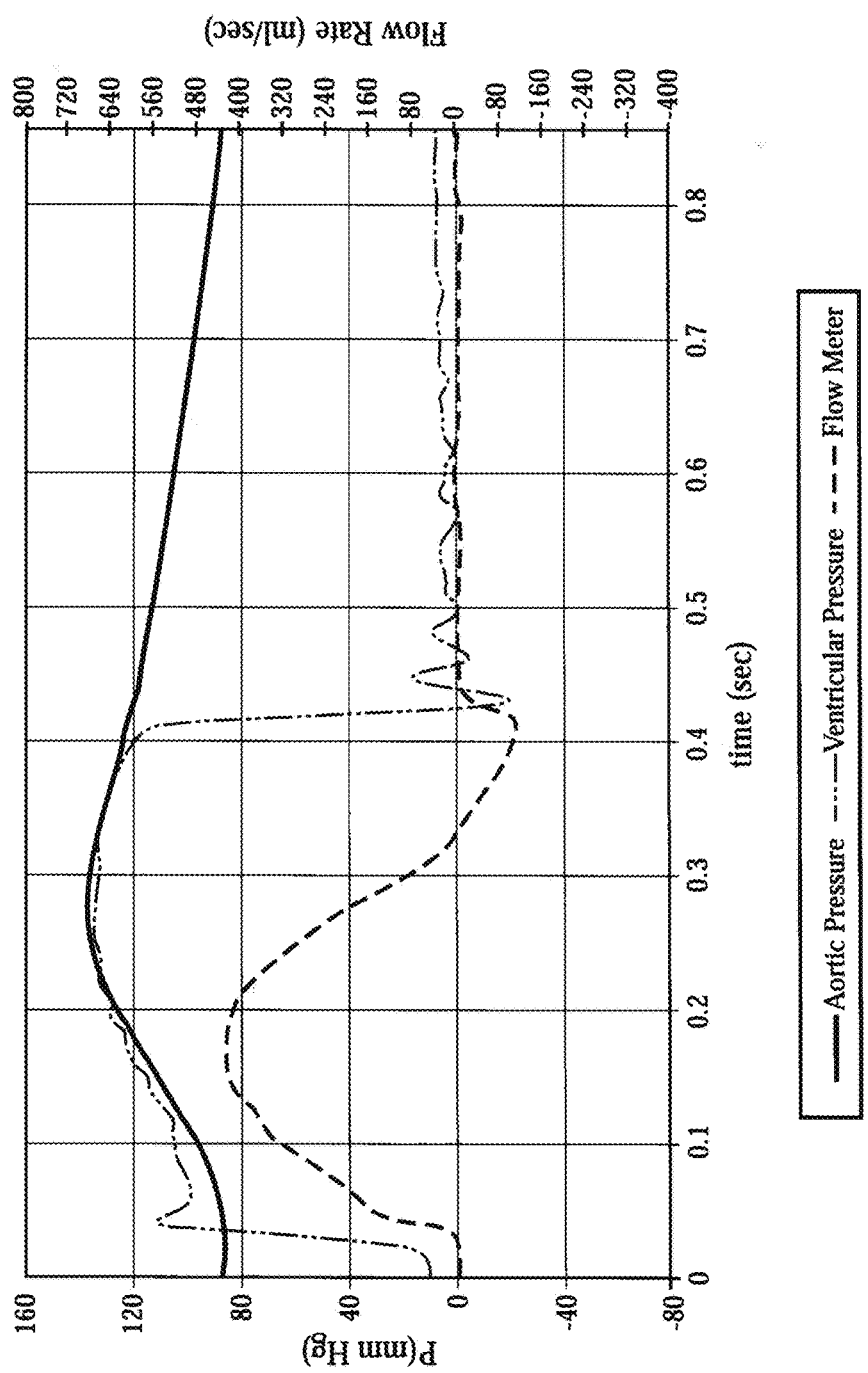
FIGS. 12A and 12B are graphs of measured outputs from the heart flow pulse duplicator system taken while testing valve assemblies according to and embodiment at zero cycles and after about 207 million cycles, respectively.
Figure 12B:
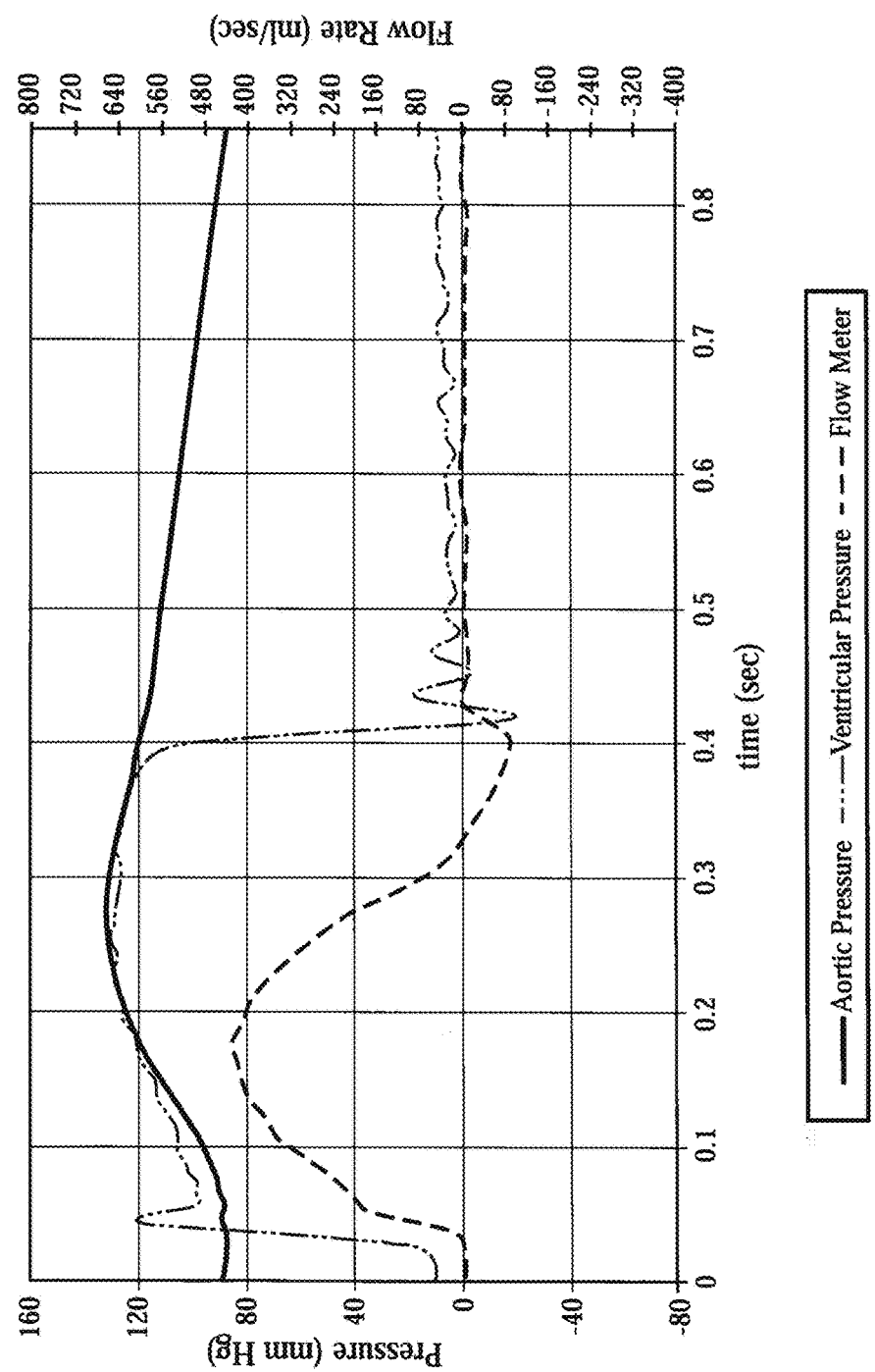

Shown in FIG. 12A is a screen shot displaying typical measured data outputs from the real-time heart flow pulse duplicator system. Shown are Ventricular Pressures, Aortic Pressures and Flow Rate. The initial or zero fatigue data for a particular valve is shown illustratively in FIG. 12A. The same measurements were taken and data were collected for the same particular valve after 207 million cycles. The 207 million cycle data for the particular valve is shown illustratively in FIG. 12B. Both sets of measurements were taken at 5 liters per minute flow rate and 70 cycles per minute rate. Comparing FIGS. 12A and 12B, it should be readily appreciated that the waveforms are substantially similar, indicating no substantial change in the valve leaflet performance after about 207 million cycles. Pressure drop, effective orifice area (EOA), and regurgitant fraction measured at zero and 207 million cycles are summarized in Table 1 below.

TABLE 1

| Number of cycles (Million) | Pressure Drop (mm Hg) | EOA ($cm^2$) | Regurgitant Fraction (%) |
|---|---|---|---|
| 0 | 5.7 | 2.78 | 12.7 |
| 207 | 7.7 | 2.38 | 9.6 |

Generally, it was observed that the valve leaflets constructed according to the embodiments described herein exhibited no physical or mechanical degradation, such as tears, holes, permanent set and the like, after 207 million cycles. As a result, there was also no observable change or degradation in the closed and open configurations of the valve leaflets even after 207 million cycles.

Example 2

Figure 14:
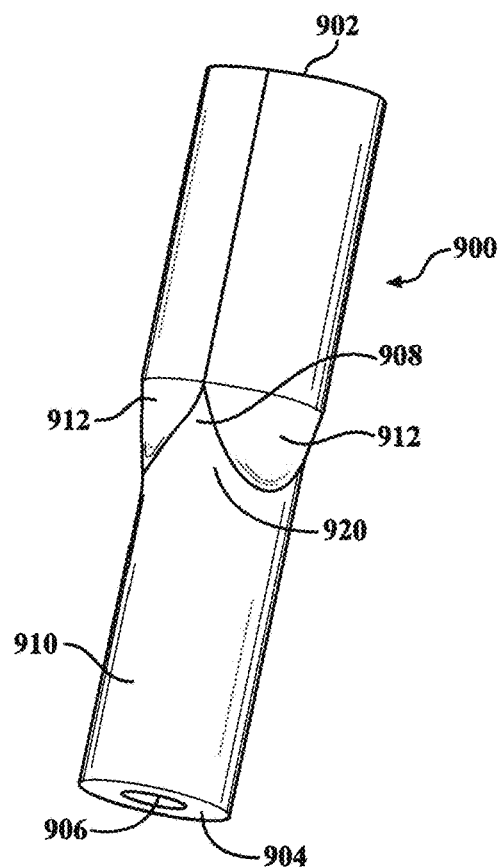
FIG. 14 is a perspective view of a mandrel for manufacturing a heart valve assembly, in accordance with an embodiment.

A heart valve having polymeric leaflets joined to a rigid metallic frame was constructed according to the following process:

A mandrel 900 was machined from PTFE having a shape shown in FIG. 14. The mandrel 900 has a first end 902 and an opposite second end 904, and extends longitudinally therebetween. The mandrel 900 has an outer surface 910 having three (two shown) generally arcuate, convex lobes 912, each generally for forming leaflets (not shown) of a finished valve assembly (not shown). The outer surface 910 also includes a frame seating area 920 for positioning a valve frame (930 in FIG. 15) relative to the convex lobes 912 prior to formation of leaflets onto the valve frame.

Figure 15:
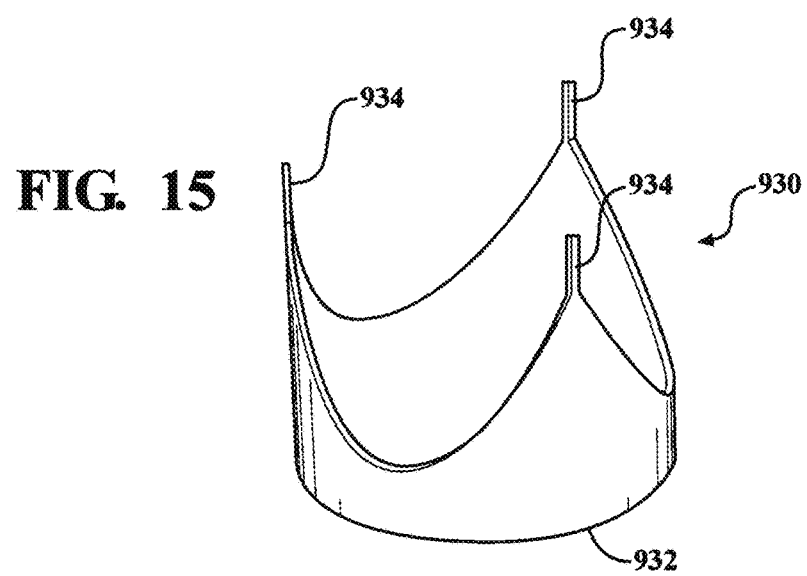
FIG. 15 is a perspective view of a valve frame for a heart valve, in accordance with an embodiment.

As shown in FIG. 15, a valve frame 930 was laser cut from a length of 316 stainless steel tube with an outside diameter of about 25.4 mm and a wall thickness of about 0.5 mm in the shape shown in FIG. 15. In the embodiment shown, the valve frame 930 extends axially between a bottom end 932 and an opposite top end defined generally by a plurality of axially extending, generally spire shaped posts 934 corresponding to the number of leaflets in the intended finished valve assembly (not shown). In the specific embodiment shown, three posts 934 are formed in the valve frame 930.

Figure 16:
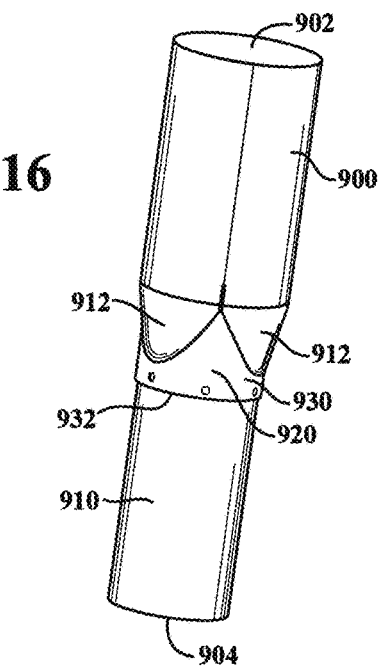
FIG. 16 is a perspective view of the valve frame of FIG. 15 nested together with the mandrel FIG. 14, in accordance with an embodiment.

Two layers of an about 4 μm thick film of FEP (not shown) was wrapped around the valve frame 930 and baked in an oven for about 30 minutes at about 270° C. and allowed to cool. The resulting covered valve frame (for clarity, shown uncovered and indicated at 930) was then slid onto the mandrel 900 so that the complementary features between the valve frame 930 and mandrel 900 are nested together, as shown in FIG. 16.

A leaflet material was then prepared having a membrane layer of ePTFE imbibed with a fluoroelastomer. More specifically, the membrane layer of ePTFE was manufactured according to the general teachings described in U.S. Pat. No. 7,306,729. The ePTFE membrane was tested in accordance with the methods described in the Appendix. The ePTFE membrane had a mass per area of about 0.57 g/m$^2$, a porosity of about 90.4%, a thickness of about 2.5 µm, a bubble point of about 458 KPa, a matrix tensile strength of about 339 MPa in the longitudinal direction and about 257 MPa in the transverse direction. This membrane was imbibed with the same fluoroelastomer as described in Example 1. The fluoroelastomer was dissolved in Novec HFE7500, 3M, St Paul, Minn., USA in an about 2.5% concentration. The solution was coated using a mayer bar onto the ePTFE membrane (while being supported by a polypropylene release film) and dried in a convection oven set to about 145° C. for about 30 seconds. After two coating steps, the resulting composite material of ePTFE/fluoroelastomer had a mass per area of about 3.6 g/m$^2$.

The composite material (not shown) was then wound around the assembled mandrel 900 and valve frame 930. In one embodiment, a total of 20 layers of the ePTFE/fluoroelastomer composite was used. Any excess composite material that extended beyond the ends of mandrel 900 were twisted and pressed lightly against the ends 902, 904 of the mandrel 900.

The composite material wrapped mandrel was then mounted in a pressure vessel so that a vent port 906 (FIG. 14) in the base or second end 904 of the mandrel 900 was plumbed to atmosphere. The vent port 906 extends from the second end 904 axially through the mandrel 900 and communicates to a generally orthogonally extending vent port 908 that extends through the outer surface 910 of the mandrel 900. The vent ports 906, 908, in addition to other vent ports which may be provided in the mandrel as needed (not shown), allow trapped air between the composite material and the mandrel to escape during the molding process.

About 690 KPa (100 psi) of nitrogen pressure was applied to the pressure vessel, forcing the ePTFE/fluoroelastomer composite against the mandrel 900 and the valve frame 930. Heat was applied to the pressure vessel until the temperature inside the vessel reached about 300° C., about 3 hours later. The heater was turned off and the pressure vessel was allowed to cool to room temperature overnight. This process thermally bonded the layers of ePTFE/fluoroelastomer composite to each other and to the FEP coating on the valve frame 930. The pressure was released and the mandrel was removed from the pressure vessel.

Figure 17:
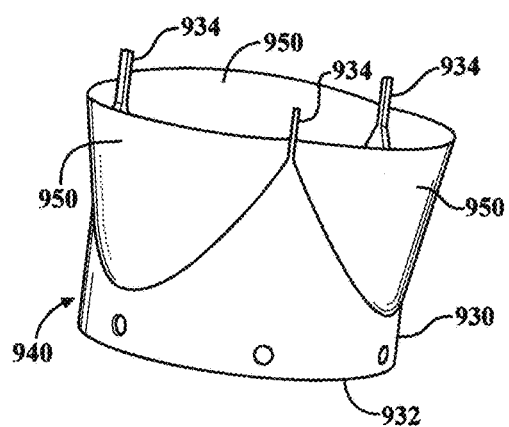
FIG. 17 is a perspective view of a molded valve, in accordance with an embodiment.

The ePTFE/fluoroelastomer composite was trimmed circumferentially in two places: first, at the bottom end 932 of the valve frame 930, and second, near the top end of the valve frame 930 along a circle generally intersecting near the mid-point of each post 934. The resulting valve assembly 940 consisting of the valve frame 930 and the trimmed composite material was separated from and slid off the mandrel The molded valve assembly 940, as shown in FIG. 17, includes the valve frame 930 and a plurality of leaflets 950 formed from the trimmed composite material. In one embodiment, the valve assembly 940 included three leaflets.

In another embodiment, each leaflet 950 in the valve assembly 940 was approximately 40 µm thick.

Figure 18:
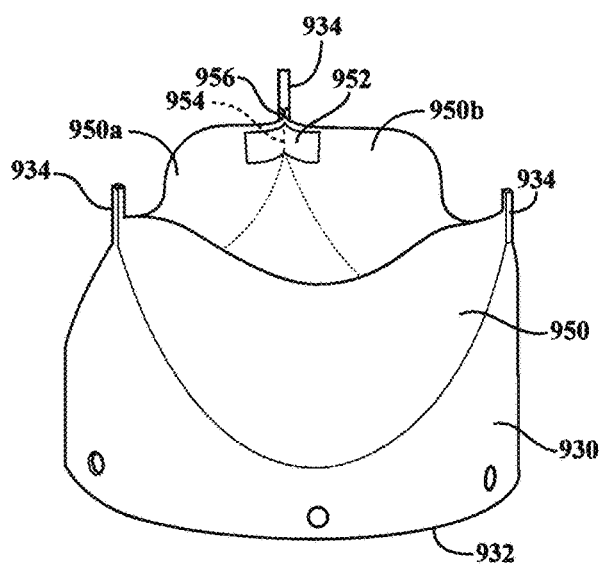
FIG. 18 is a perspective view of a molded valve, showing an attachment member for reinforcing a bond between adjacent valve leaflets and a post of a valve frame, in accordance with an embodiment.

To help control the degree of opening of the valve, adjacent leaflets about each post were bonded together. As shown in FIG. 18, the adjacent leaflets 950a, 950b were wrapped around the post 934 and bonded together to form a seam 954. The seam 954 had a depth 956 extending to at least about 2 mm from the post 934. To support the bond between the adjacent leaflets 950a, 950b, an attachment member 952 was fixedly secured to inner surfaces of the adjacent leaflets 950a, 950b thereby bridging the seam 954 between the adjacent leaflets 950a, 950b. As shown in FIG. 18, the attachment member 952 was generally rectangular. It should be appreciated, however, that other shapes for the attachment member may be utilized. The attachment member 952 was formed from the same type of composite material used to form the leaflets 950. The attachment member 952 was fixedly secured to the inner surfaces of the adjacent leaflets 950a, 950b using the fluoroelastomer solution previously described. These steps were repeated for the other pairs of adjacent leaflets of the valve assembly.

The performance and durability of the valve leaflets in this example were analyzed in the same manner as described in Example 1. The valve assembly was initially characterized on the same real-time pulse duplicator as described in Example 1 that measured typical anatomical pressures and flows across the valve, generating an initial or "zero fatigue" set of data for that particular valve assembly. The valve was then subjected to accelerated testing as in Example 1. After about 79 million cycles, the valve was removed from the high rate fatigue tester and the hydrodynamic performance again characterized as in Example 1. The valve was removed finally at about 198 million cycles. Pressure drop, EOA and regurgitant fraction measured at about 79 million cycles and about 198 cycles are summarized in Table 2 below.

Figure 13A:
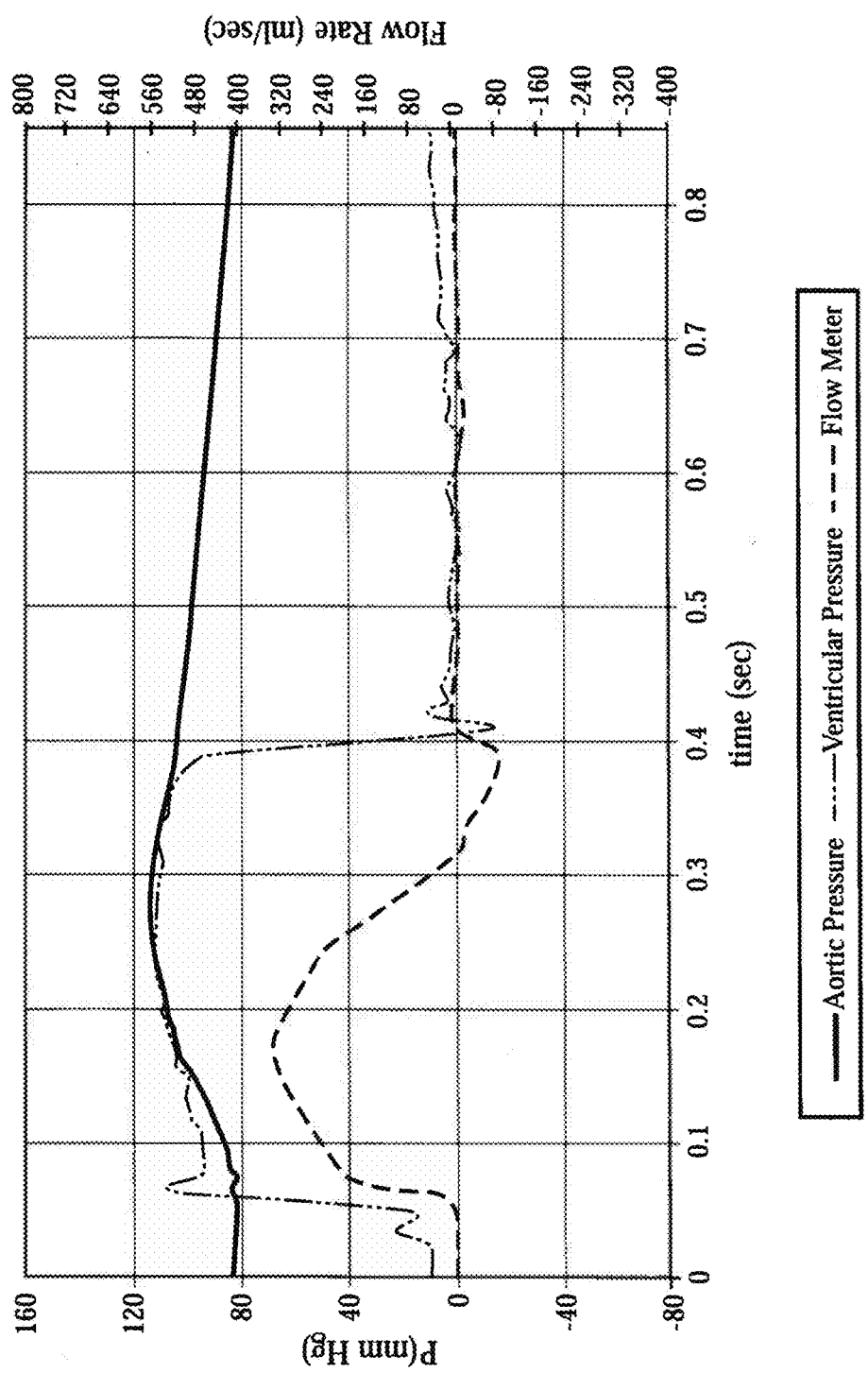
FIGS. 13A and 13B are graphs of measured outputs from the heart flow pulse duplicator system taken while testing valve assemblies in accordance with embodiments at about 79 million cycles and after about 198 million cycles, respectively.
Figure 13B:
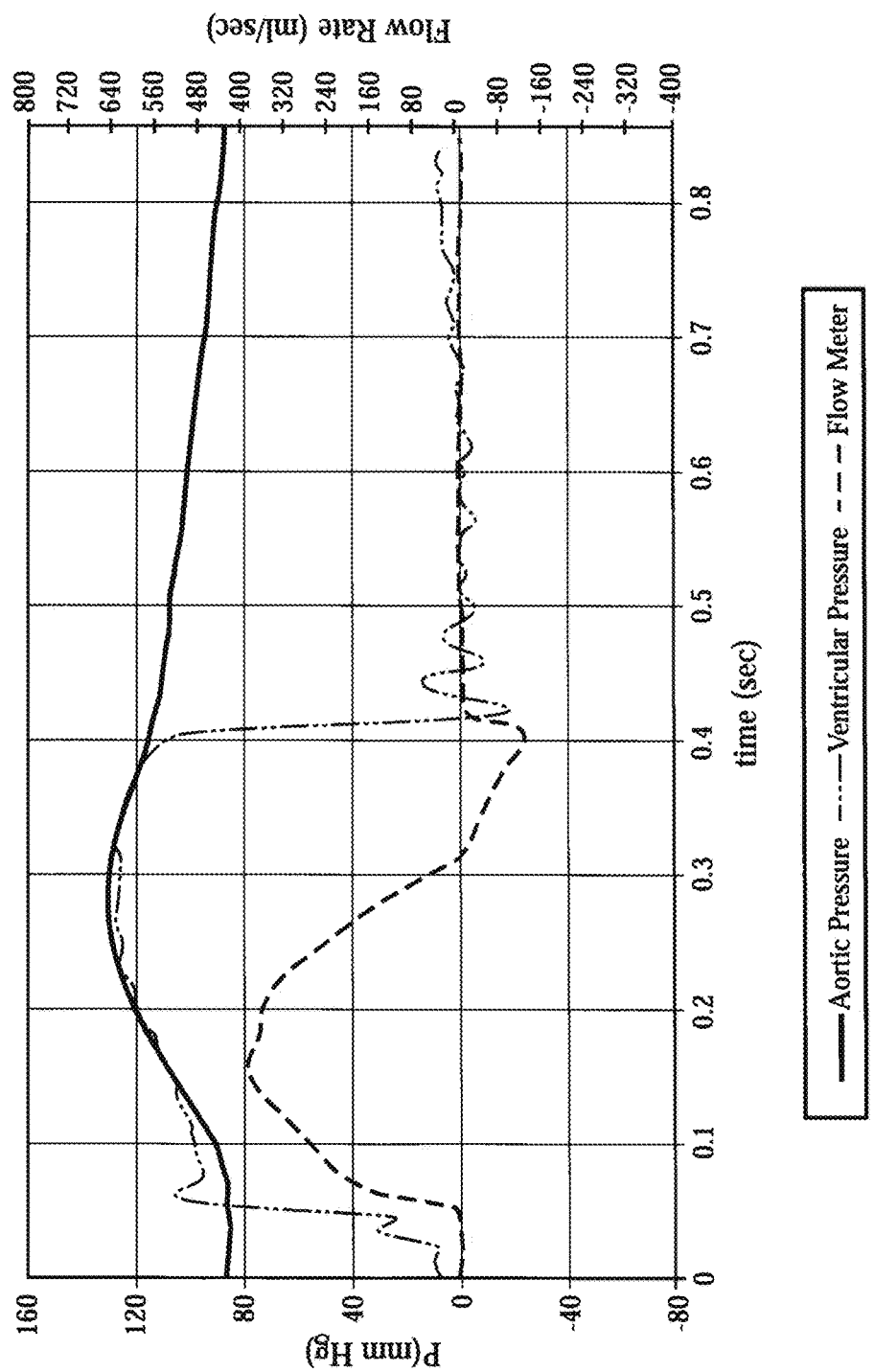

FIGS. 13A and 13B display similar results for a similar valve. FIG. 13A is a graph of measured data output from the heart flow pulse duplicator system taken after about 79 million cycles. The same measurements were taken for the similar valve after about 198 million cycles, a graph of which is shown illustratively in FIG. 13B. Both sets of measurements were taken at about 4 liters per minute flow rate and about 70 cycles per minute rate. Comparing FIGS. 13A and 13B, it should be again appreciated that the waveforms are significantly similar, indicating no substantial change in the valve leaflet performance after about 198 million cycles. Pressure drop, effective orifice area (EOA), and regurgitant fraction measured at 0, about 79, and about 198 million cycles are summarized in Table 2 below. These data indicate no substantial change in the valve leaflet performance after about 198 million cycles.

TABLE 2

| Number of Cycles (Million) | Pressure Drop (mm Hg) | EOA (cm$^2$) | Regurgitant Fraction (%) |
| --- | --- | --- | --- |
| 0 | 6.8 | 2.56 | 7.8 |
| 79 | 5.4 | 2.58 | 10.25 |
| 198 | 4.4 | 2.60 | 10.1 |

Example 3

Figure 19:
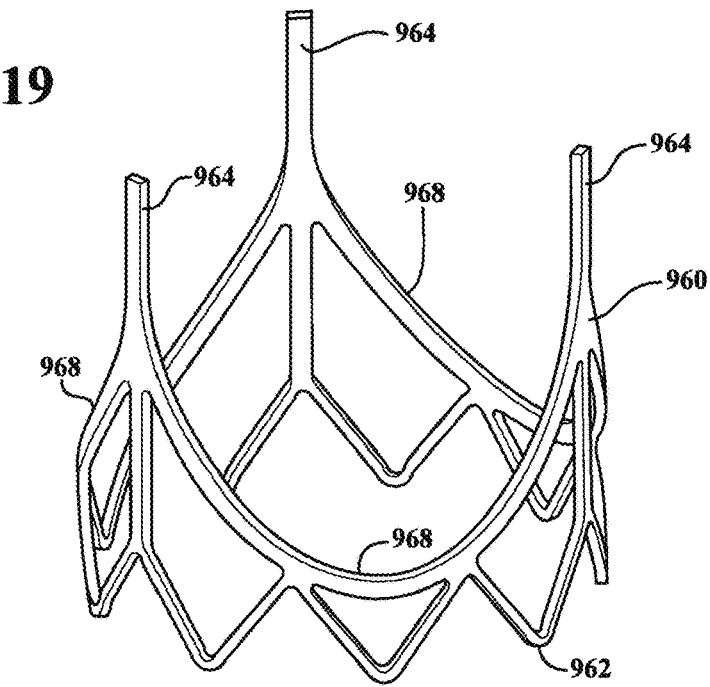
FIG. 19 is a perspective view of a valve frame, in accordance with an embodiment.

A heart valve having polymeric leaflets joined to a rigid metallic frame was constructed according to the following process:

A valve support structure or frame 960 was laser cut from a length of 316 stainless steel tube with an outside diameter of about 25.4 mm and a wall thickness of about 0.5 mm in the shape shown in FIG. 19. In the embodiment shown, the frame 960 extends axially between a bottom end 962 and an opposite top end defined generally by a plurality of axially extending, generally spire shaped posts 964 corresponding to the number of leaflets in the intended finished valve assembly (not shown). A parabolically shaped top edge 968 extends between adjacent posts 964. In the specific embodiment shown, three posts 964 and three top edges 968 form the top end of the frame 960. The corners of the frame that would be in contact with the leaflet material were rounded using a rotary sander and hand polished. The frame was rinsed with water and then plasma cleaned using a PT2000P plasma treatment system, Tri-Star Technologies, El Segundo, Calif., USA.

Figure 20:
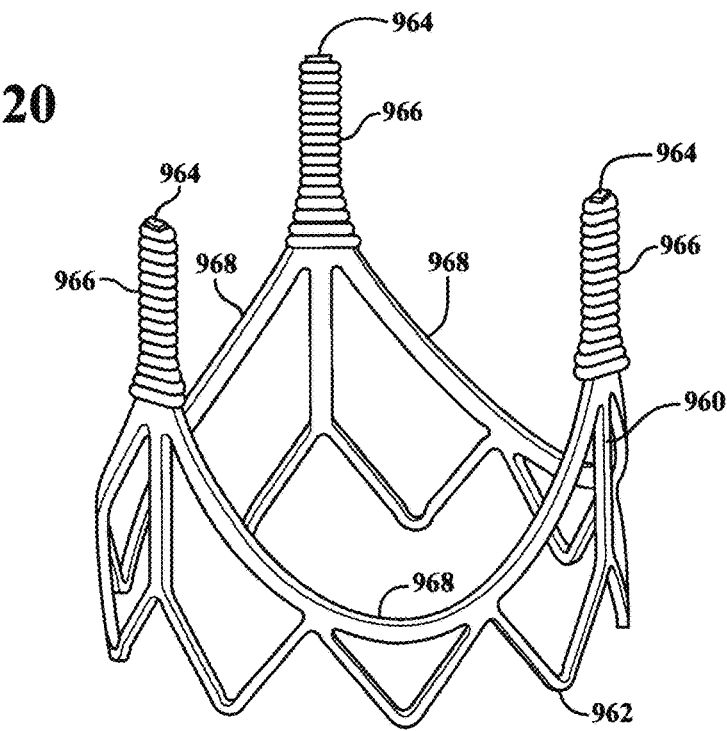
FIG. 20 is a perspective view of the valve frame of FIG. 19 with posts that are cushion-wrapped, in accordance with an embodiment.

In one embodiment, a cushion member is provided between at least a portion of the frame and at least a portion of the leaflet to minimize stress related to direct contact between the frame and the leaflet. A composite fiber of ePTFE and silicone was created by first imbibing an ePTFE membrane with silicone MED-6215 (NuSil, Carpinteria, Calif., USA), slitting it to a width of about 5 mm, and rolling into a substantially round fiber. The ePTFE used in this fiber was tested in accordance with the methods described in the Appendix. The ePTFE membrane had a bubble point of about 217 KPa, a thickness of about 10 µm, a mass per area of about 5.2 g/m$^2$, a porosity of about 78%, a matrix tensile strength in one direction of about 96 MPa, and a matrix tensile strength of about 55 MPa in an orthogonal direction. The composite fiber 966 was wrapped around each of the posts 964 of the frame 960 as shown in FIG. 20.

A mandrel 970 was formed using stereolithography in a shape shown in FIG. 21. The mandrel 970 has a first end 972 and an opposite second end 974, and extends longitudinally therebetween. The mandrel 970 has an outer surface 980 having three (two shown) generally arcuate, convex lobes 982, each generally for forming leaflets (not shown) of a finished valve assembly (not shown). The outer surface 980 also includes a frame seating area 984 for positioning the frame (960 in FIG. 19) relative to the convex lobes 982 prior to formation of the valve leaflets onto the valve frame.

The mandrel 970 was then spray coated with a PTFE mold release agent. Four layers of the ePTFE membrane previously described in this example were wrapped around the mandrel. MED-6215 was wiped onto the ePTFE and allowed to wet into and substantially fill the pores of the ePTFE. Excess MED-6215 was blotted off and the frame 960 with the composite fiber 966 wrapped posts 964 was positioned on the mandrel 970 along the frame seating area 984, as shown in FIG. 22. Silicone MED-4720, NuSil, Carpinteria, Calif., USA was placed along the top edges 968 of the frame 960 and along the posts 964 of the frame 960 to create a strain relief within the leaflet (not shown). Eight additional layers of ePTFE were wrapped around the frame 960 and mandrel 970. Additional MED-6215 was wiped onto the ePTFE and allowed to wet into and substantially fill the pores of the ePTFE. Another 8 layers of ePTFE were wrapped around the frame 960 and mandrel 970. These layers form a blotter to absorb any excess silicone during the molding process and were removed after the silicone had cured.

Silicone rubber forms (not shown) molded with one surface exactly matching the inverse shape of the mandrel surface were previously fabricated for each of the 3 leaflet-forming features. These forms were spray coated with PTFE mold release and then mated to the matching feature of the mandrel. Approximately 50 wraps of an ePTFE fiber (not shown) were wound around the silicone forms to apply generally radial pressure to the valve against the mandrel.

Figure 23:
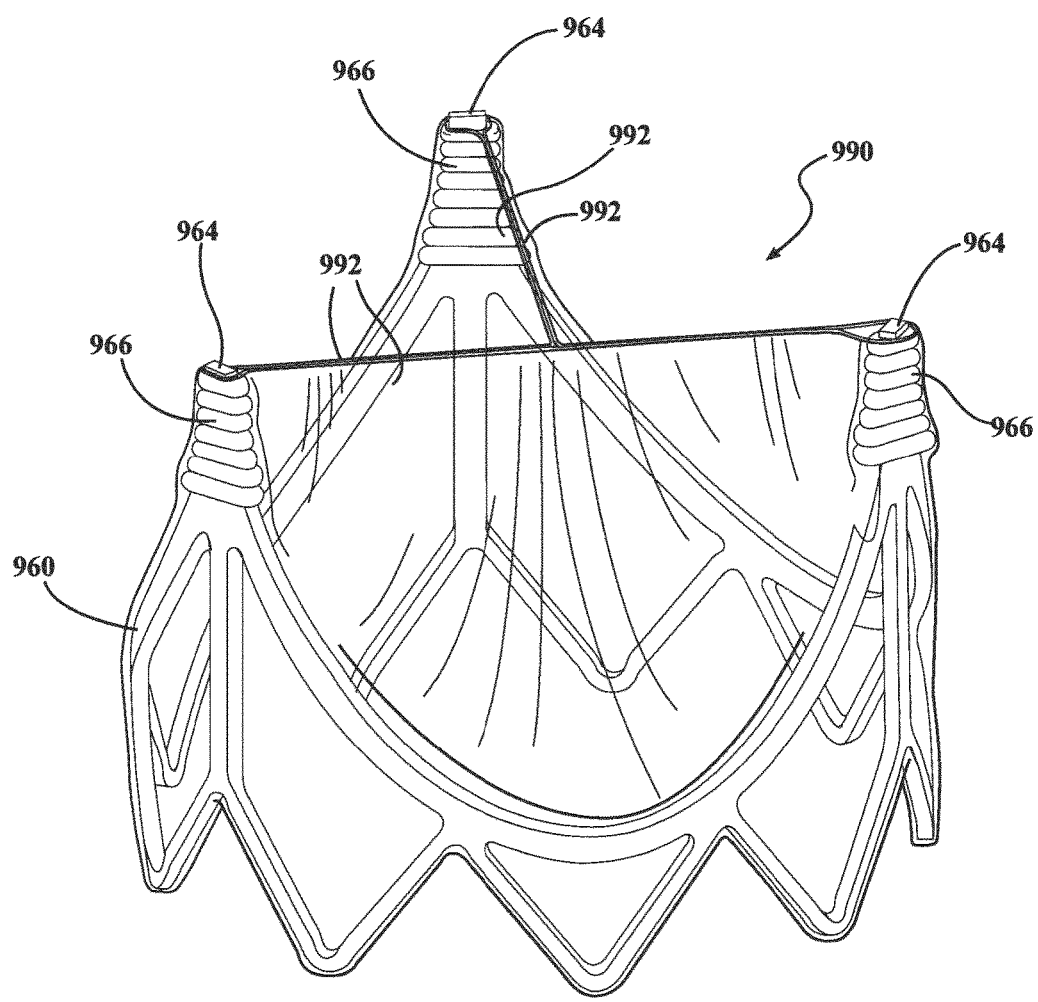
FIG. 23 is a perspective view of a valve having valve leaflets coupled to and supported on the cushion-wrapped valve frame of FIG. 20, in accordance with an embodiment.

This assembly was then placed in an oven at about 100° C. for about 1 hour to cure the silicone. After cooling, the fiber and silicone forms were removed, the 8 layers of blotter ePTFE were peeled away and discarded, and the resulting valve (not shown) was slid off of the mandrel. The posts were trimmed using wire cutters and the excess length of leaflet material and excess length of material at the base of the frame was carefully trimmed using scissors to form a completed valve assembly, which is shown and generally indicated at 990 in FIG. 23. Thus, in one embodiment, the valve assembly 990 was formed having the frame or support structure 960; a plurality of leaflets 992 supported on the support structure 960 and movable between open and closed positions to regulate blood flow through the valve assembly 990; and a composite fiber 966 wrapped post 964 located between at least a portion of the support structure 960 and at least a portion of each leaflet 992 to minimize stress in the leaflets due to the coupling and/or proximity of the leaflets to the support structure. In another embodiment, the cushion member is formed from a composite material with at least one fluoropolymer layer having a plurality of pores and an elastomer present in substantially all of the pores, as described above.

It should be appreciated that support structures other than as specifically shown in the figures may be utilized. Further, cushion members may be utilized anywhere along the support structure as necessary to minimize stress in the leaflets due to the coupling and/or proximity of the leaflets to the support structure. For example, cushion member(s) may be coupled to the support structure along the parabolically shaped top edge.

It should also be appreciated that the cushion members may be formed as sheets and wrapped around desired locations along the support structure, or be formed from fibers of various cross sectional shapes and sizes.

It should also be appreciated that the cushion members may be formed as tubes and slid over the ends of the support structure, or be slit longitudinally and positioned around the desired location along the support structure.

The leaflets of the complete valve assembly were measured and determined to have an average thickness at the center of each leaflet of about 120 µm.

The valve assembly was then characterized for flow performance and subjected to accelerated testing as in Example 1. After each block of about 50 million cycles, the valve assembly was removed from the high rate fatigue tester and the hydrodynamic performance again characterized as in Example 1. The valve assembly was removed finally at about 150 million cycles and demonstrated acceptable performance and no hole formation.

Comparative Example A

Six valves were constructed in the manner of Example 1 with the exception that the elastomer was not incorporated. The ePTFE material was the same as that described in Example 1, but it was not imbibed with the fluoroelastomer copolymer and was instead coated with a discontinuous layer of FEP copolymer that served as a thermoplastic adhesive. Valves were constructed as in Example 1 with each leaflet comprising 3 layers of membrane resulting in a final leaflet thickness averaging about 20 µm. After hydrodynamic characterization, the valves were mounted in the Dynatek accelerated tester described in Example 1. By about 40 million cycles, edge delamination and hole formation in the leaflets was observed and the test was stopped.

Comparative Example B

Two valves were constructed in the manner of Example 1 but did not incorporate the elastomer portion of the embodiments. The material employed was thin ePTFE membrane possessing properties similar to the following: a mass per area of about 2.43 g/m$^2$, a porosity of about 88%, an IBP of about 4.8 KPa, a thickness of about 13.8 µm, a matrix tensile strength in one direction of about 662 MPa, and a matrix tensile strength of about 1.2 MPa in the orthogonal direction. The ePTFE membrane was tested in accordance with the methods described in the Appendix. Ten layers of the membrane were placed in alternating directions onto a stack and then placed on the tooling as described in Example 1. The tooling was then exposed to about 350° C. in a convection air oven for about 25 minutes, removed and quenched in a water bath. The three pieces of tooling were then inserted into the stent frame and the leaflets bonded to the valve assembly with FEP as in Example 1.

Each valve was subjected to high-rate fatigue testing using the real-time heart flow pulse duplicator system, as described above. After about 30 million cycles on one valve and about 40 million cycles on another valve, visual degradation, including stiffening and deformation, was observed and measurable decrease in performance was noted. In addition to the visual and measurable degradation in performance, Table 3 below summarizes the pressure drop, effective orifice area (EOA), and regurgitant fraction measured after about 40 million cycles.

TABLE 3

| Number of Cycles (Millions) | Pressure Drop (mm Hg) | EOA (cm$^2$) | Regurgitant Fraction (%) |
|---|---|---|---|
| 0 | 3.9 | 3.11 | 8.1 |
| 40 × 10$^6$ | 6.5 | 2.85 | 14.1 |

The material properties of the following non-limiting examples are provided in FIG. 42, Table 4, for reference to the individual descriptions, wherein like parts from the previous exemplary embodiments are enumerated with like prime numerals.

Example 4a

Figure 24:
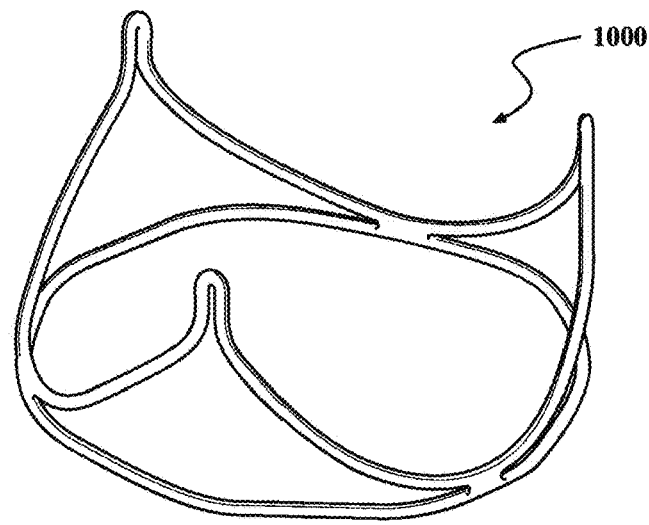
FIG. 24 is a perspective view of a non-collapsible stent frame or support structure, in accordance with an embodiment.

In exemplary embodiments, a heart valve having polymeric leaflets formed from a composite material having an expanded fluoropolymer membrane and an elastomeric material and joined to a semi-rigid, non-collapsible metallic frame, and further a having strain relief and sewing ring was constructed according to the following process:

A valve frame was laser machined from a length of MP35N cobalt chromium tube hard tempered with an outside diameter of 26.0 mm and a wall thickness of 0.6 mm in the shape shown illustratively and generally indicated at 1000 in FIG. 24. The frame 1000 was electro-polished resulting in 0.0127 mm material removal from each surface and leaving the edges rounded. The frame 1000 was exposed to a surface roughening step to improve adherence of leaflets to the frame 1000, without degrading fatigue durability performance. The frame 1000 was cleaned by submersion in an ultrasonic bath of acetone for approximately five minutes. The entire metal frame surface was then subjected to a plasma treatment using methods commonly known to those having ordinary skill in the art. This treatment also served to improve the wetting of the fluorinated ethylene propylene (FEP) adhesive.

FEP powder (Daikin America, Orangeburg N.Y.) was then applied to the frame. More specifically, the FEP powder was stirred to form an airborne "cloud" in an enclosed blending apparatus, such as a standard kitchen type blender, while the frame is suspended in the cloud. The frame was exposed to the FEP powder cloud until a uniform layer of powder was adhered to the entire surface of the frame. The frame was then subjected to a thermal treatment by placing it in a forced air oven set to 320° C. for approximately three minutes. This caused the powder to melt and adhere as a thin coating over the entire frame. The frame was removed from the oven and left to cool to room temperature.

Figure 25:
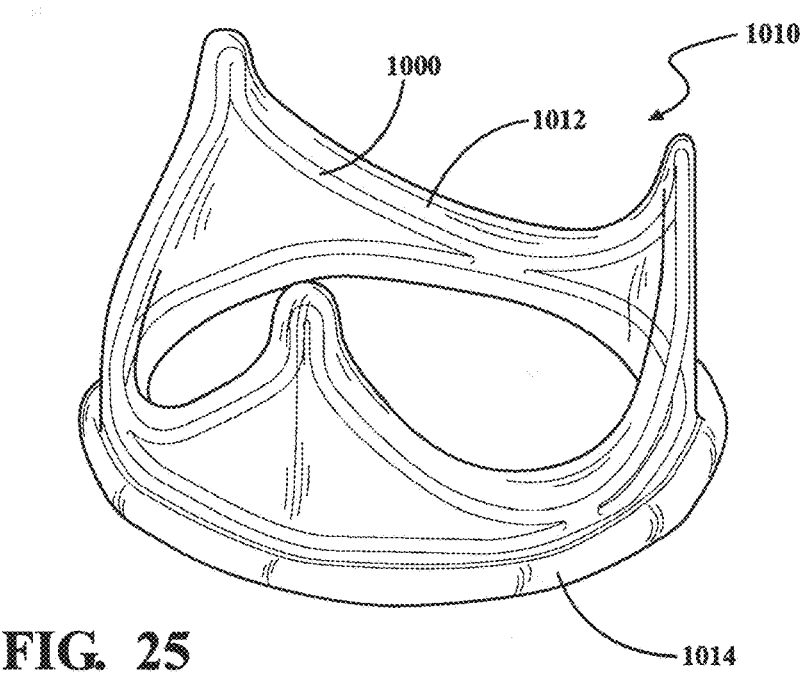
FIG. 25 is a perspective view of a laminated stent frame, in accordance with an embodiment.

The strain relief and sewing ring were attached to the frame in the following manner. A 23 mm diameter cylindrical mandrel was wrapped with a single layer of Kapton® (El DuPont de Nemours, Inc., Wilmigton, Del.) polyimide film and held in place by an adhesive strip of Kapton® tape over the length of the overlapping seam. One wrap of a two layer laminate consisting of an ePTFE membrane laminated to a 25.4 µm thick layer of fluoroelastomer, as described in Example 1, was wrapped with the high strength of the membrane aligned along a direction generally parallel with the axis of the Kapton®-covered mandrel with no substantially overlap at the seam. The frame was aligned coaxially over the wrapped mandrel. An additional wrap of the two layer laminate was wrapped onto the mandrel encapsulating the entire frame with the seam oriented 180° from the seam of the single inner wrap. The four layer laminate was end cut about 135 mm from the base of the frame encapsulated within. The four layer laminate was hand rolled axially in the toward the base of the frame until the 135 mm length of material formed an approximate 3 mm outer diameter ring adjacent to the base of the frame. The four layer laminate was end cut approximately 20 mm from the top of the frame and the assembly was compression wrapped helically with two sacrificial layers of ePTFE membrane imbibed with a polyimide, four layers of unsintered ePTFE membrane, and approximately one hundred wraps of an ePTFE fiber. The entire assembly was subjected to a thermal treatment by placing it in a forced air oven set to 280° C. for five minutes and returned to room temperature by immediate water quench upon removal from the oven. The sacrificial layers were removed and the four layer laminate at the top end of the frame trimmed to allow about a 2 mm length to extend beyond the perimeter of the top of the frame. The mandrel and Kapton were then removed from the interior of the frame resulting in the frame assembly, generally indicated at 1010 in FIG. 25, having the strain relief 1012 and sewing ring 1014 with the frame 1000 laminated within.

A single female mold or base tool, shown illustratively and indicated at 50 in FIG. 5*a*, is provided with concave cavities (502, 504, 506) generally defining the shape of the tri-leaflet. Three male molds or leaflet tools (100) are provided with end surfaces (103) corresponding in shape and contour with the concave cavities in the base tool. The leaflet tools are pivotally coupled to each other, which helps to maintain relative axial and rotational spacing as depicted in the tri-leaflet assembly (400) in FIG. 5*a*. The base and leaflet tools are wrapped with a single layer of un-sintered ePTFE membrane to form a cushioning layer and then a single layer of substantially nonporous ePTFE membrane with FEP on one side is used to adhere the membranes together and onto the mandrels with a soldering iron. The sacrificial layers ensure that all the mating surfaces between the base and leaflet tools have a cushioning layer when compressed together; an additional function is as a release layer to prevent the leaflet material from adhering to the tools. The base and leaflet tools are initially combined to create a single cylindrical structure or combined tool assembly, as depicted in FIG. 5b, to facilitate leaflet construction and attachment to the frame with the strain relief and sewing ring component via a tape wrapping process, as discussed in detail below.

A leaflet material was then prepared. A membrane of ePTFE was manufactured according to the general teachings described in U.S. Pat. No. 7,306,729. The ePTFE membrane had a mass per area of 1.15 g/m$^2$, a bubble point of 79.7 MPa, a thickness of about 1016 nm, a matrix tensile strength of 410.9 MPa in the longitudinal direction and 315.4 MPa in the transverse direction. This membrane was imbibed with a fluoroelastomer, as described above in Example 1. The fluoroelastomer was dissolved in Novec HFE7500 (3M, St Paul, Minn.) in a 2.5% concentration. The solution was coated using a mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 4.08 g/m$^2$, 28.22% fluoropolymer by weight, a dome burst strength of 15.9 KPa, and thickness of 1.93 μm.

Three layers of the leaflet or composite material was wrapped around the combined tool assembly with an elastomer rich side of the composite facing away from the tools. In exemplary embodiments, the composite material is oriented to have a predetermined matrix tensile strength along a direction generally parallel with the longitudinal axis of the combined tool assembly. More specifically, the predetermined matrix tensile strength is about 410 MPa.

Figure 26A:
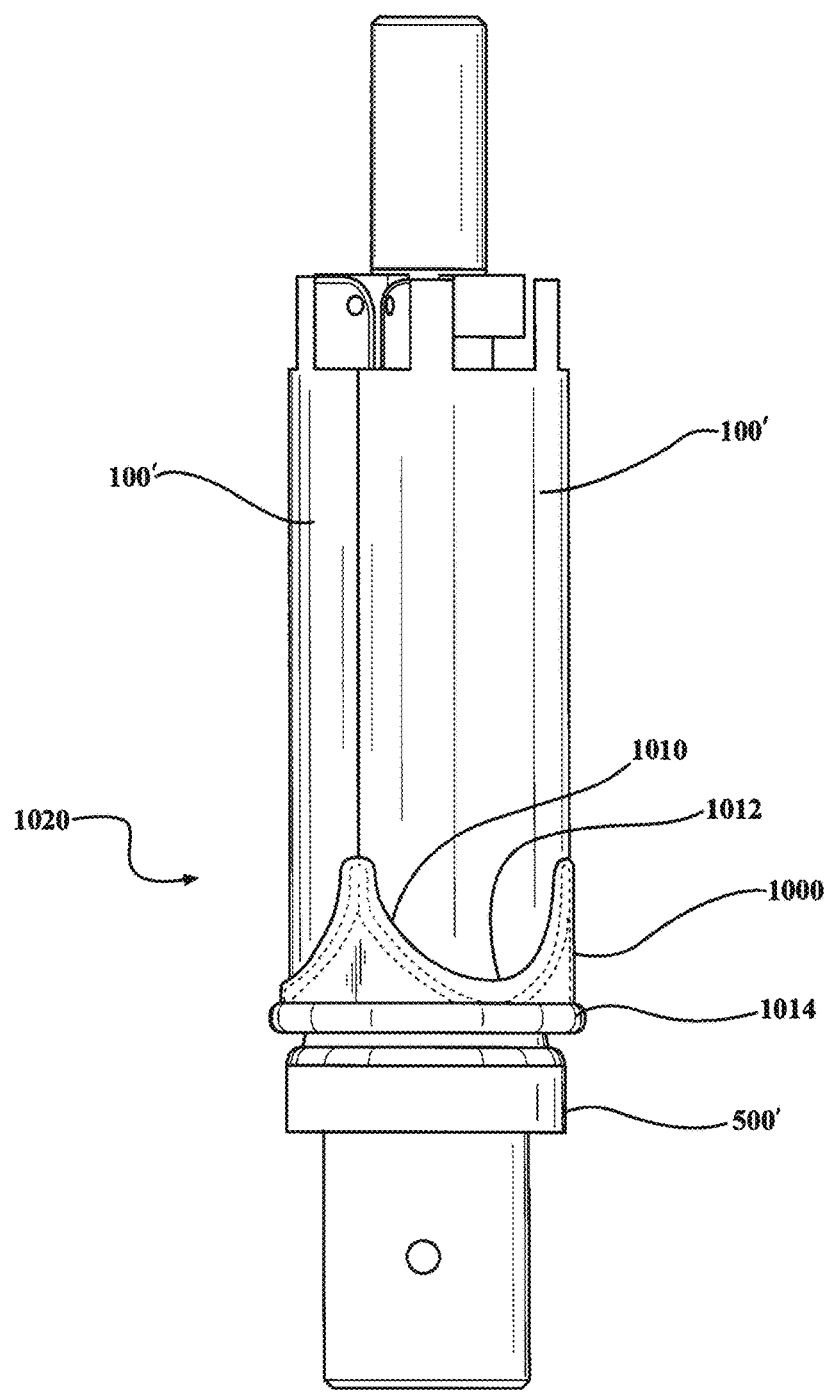
FIG. 26A is a perspective view of the tri-leaflet assembly, base tool, stent frame encapsulated within a composite strain relief and sewing ring, in accordance with an embodiment.
Figure 26B:
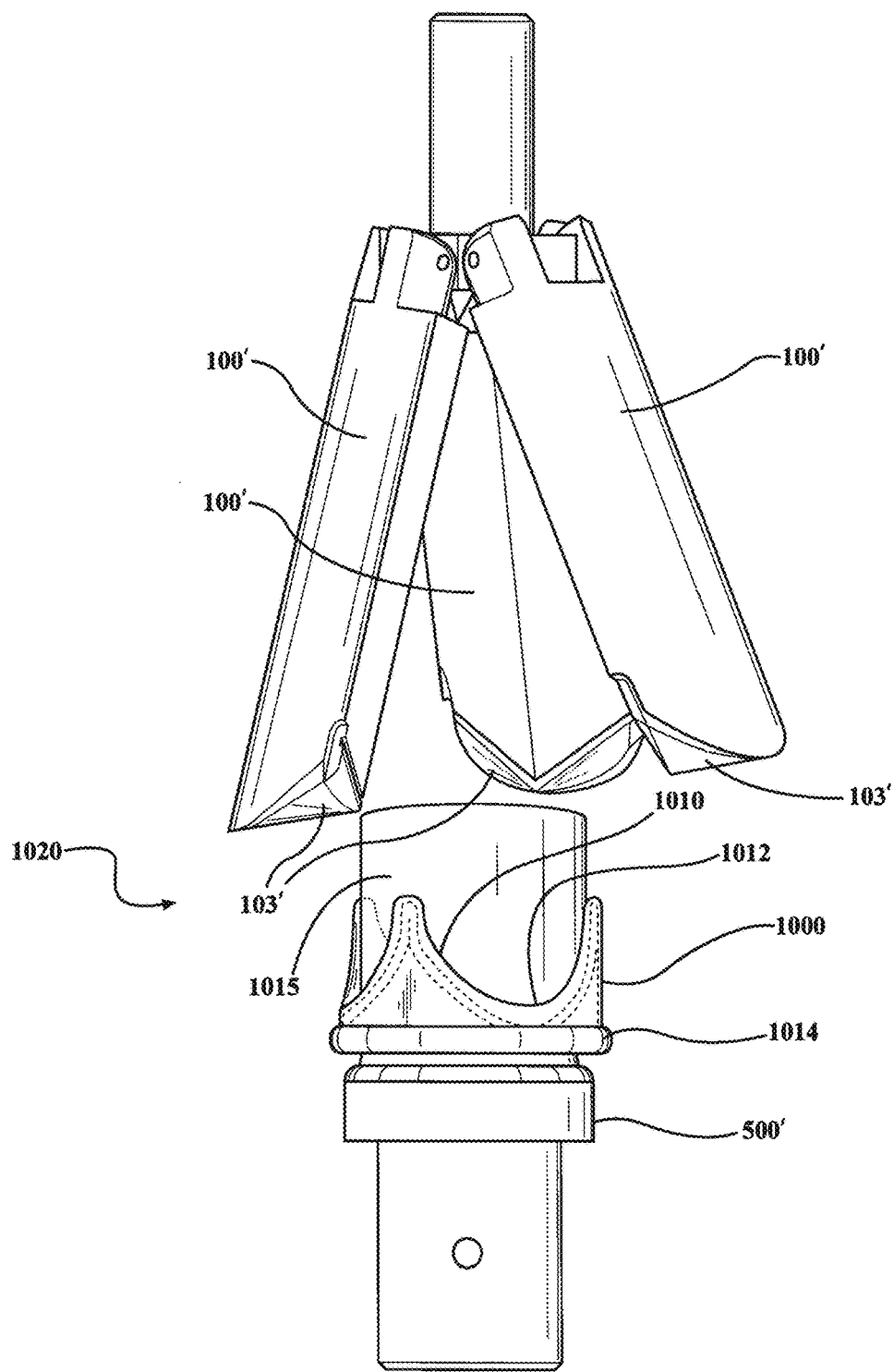
FIG. 26B is a perspective view of a tri-leaflet assembly, in accordance with an embodiment.

Referring to FIGS. 26a and 26b, the frame assembly 1010 was positioned co-axially onto the combined tool assembly, generally indicated at 1020, over the three inner wraps of the composite material. The frame assembly 1010 was also aligned rotationally to match the features of the base tool 500', as depicted in FIG. 26a. Twenty-three additional layers of the composite material were wrapped around the combined tool assembly 1020 with the elastomer rich side of each layer facing toward the tools previously wrapped by the three aforementioned layers of composite material. In exemplary embodiments, the additional layers of the composite material were each oriented to have a predetermined matrix tensile strength along a direction generally parallel with the longitudinal axis of the combined tool assembly. In one embodiment, the predetermined matrix tensile strength was about 410 MPa. The leaflet tools 100' were then removed from underneath the twenty-six layer composite laminate tube.

Each of the leaflet tools 100' was then moved rotatably about its respective end pivot, as depicted in FIG. 26b, to allow the composite laminate tube 1015 from the previous step to be positioned between the leaflet tools 100'. The leaflet tool assembly was coaxially aligned to the base tool 500' and the leaflet tools 100' rotated inwardly toward each other to compress the twenty-six layer composite laminate tube onto the female tri-leaflet mold surface configuration of the base tool 500'. The combined tool assembly comprising the leaflet and base tools, composite laminate, strain relief, frame, and sewing ring was then mounted between fixed and translational portions of a fixture. Both radial and axial compression were applied by radially clamping the leaflet tools 100' while simultaneously applying an axial load with the translational end of the fixture.

The combined tool assembly was then compression wrapped helically with two sacrificial layers of compliant ePTFE membrane imbibed with a polyimide, four layers of un-sintered ePTFE membrane, and approximately one hundred wraps of an ePTFE fiber. The entire assembly was removed from the lathe and placed in a clamping fixture to maintain axial compression while subjected to a thermal treatment by placing it in a forced air oven set to about 280° C. for about 30 minutes. The assembly was removed from the oven and brought back to room temperature via immediate water quench. The sacrificial layers, leaflet and base tools were removed leaving a fully adhered valve in a closed three dimensional form.

Figure 27:
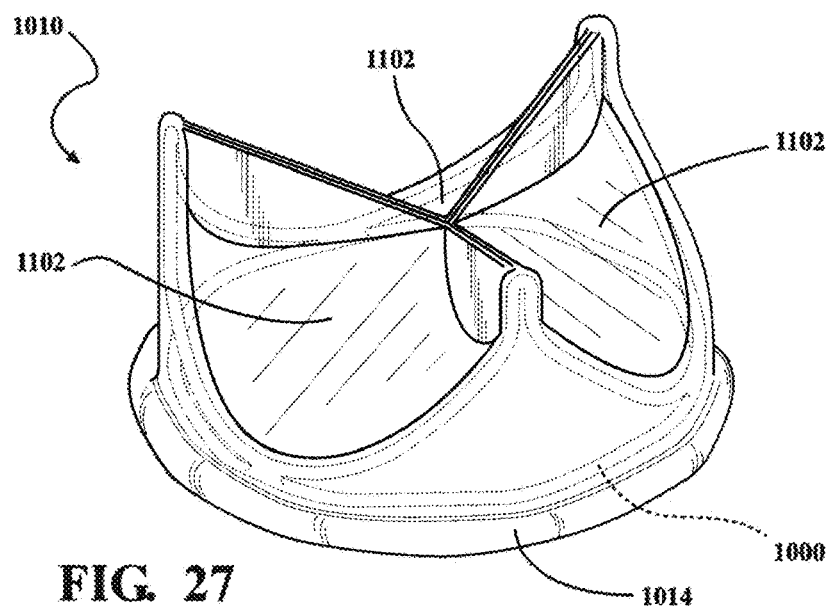
FIG. 27 is a perspective view of a valve, in accordance with an embodiment.
Figure 28:
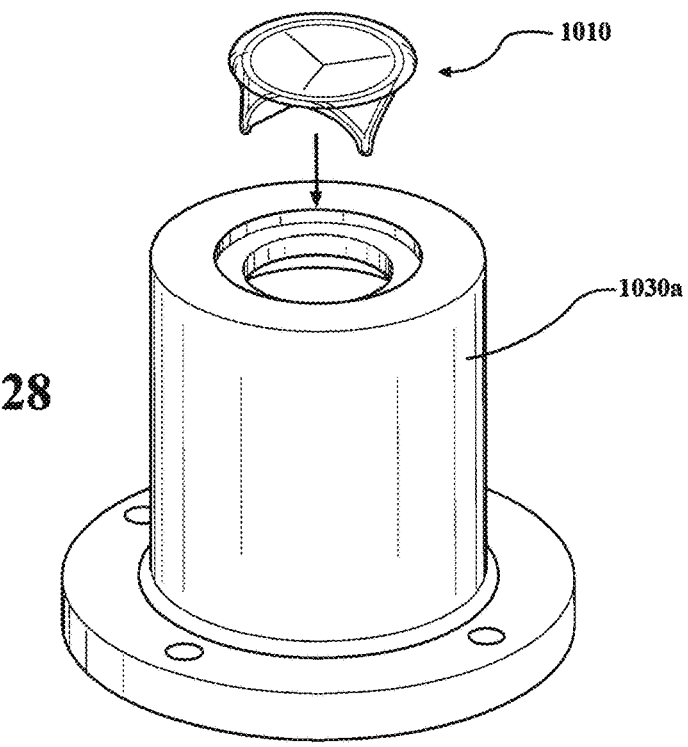
FIG. 28 is a perspective view of a valve and fixture, in accordance with an embodiment.
Figure 29:
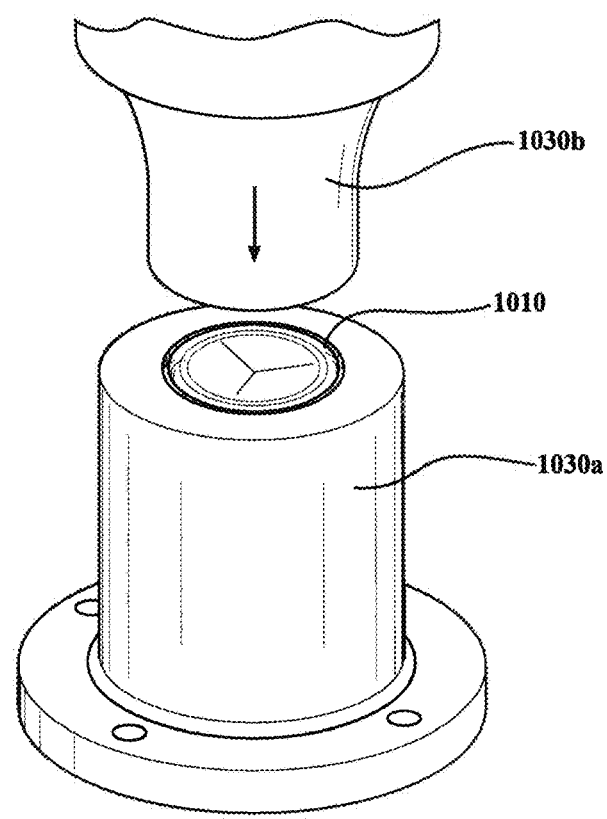
FIG. 29 is a perspective view of a valve, fixture, and press, in accordance with an embodiment.
Figure 30:
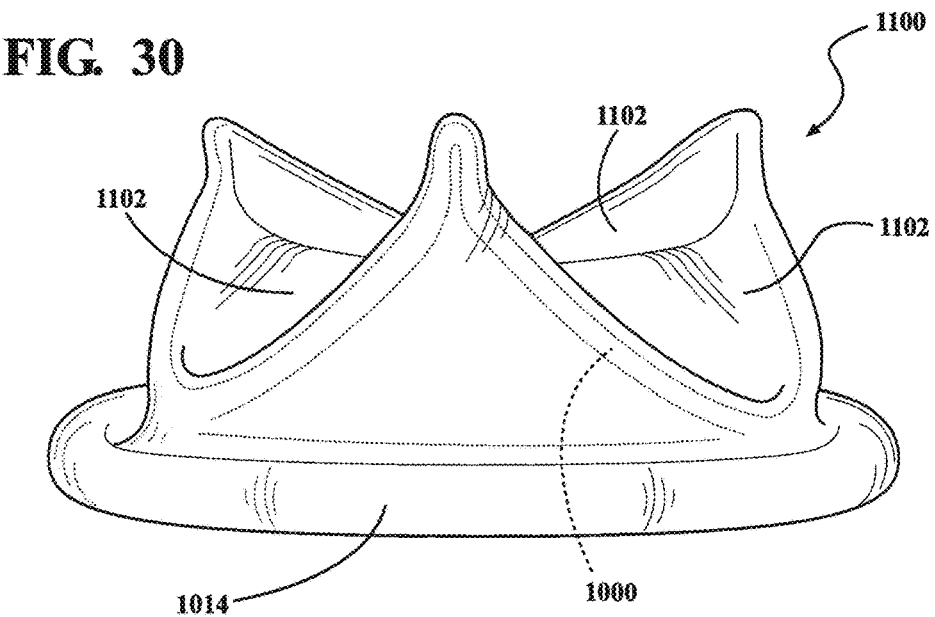
FIG. 30 is a perspective view of a completed valve, in accordance with an embodiment.

The excess leaflet material was trimmed with scissors from the top of the frame posts to the common triple point of each leaflet to create three commissures or coapting surface regions as depicted in FIG. 27. The leaflets were opened with an ePTFE mandrel tapered from 10 mm to 25 mm. The annular sewing ring 1014 at the base of the frame 1000 was molded into a flange by placing the frame assembly 1010 between corresponding halves 1030a, 1030b of a fixture, as illustrated in FIGS. 28 and 29 and placing the assembly in an ultrasonic compression welder (not shown), such as a model #8400 ultrasonic compression welder made by Branson ultrasonics, Danbury Conn. A weld time of about 0.8 seconds, hold time of about 3.0 seconds, and pneumatic pressure of about 0.35 MPa was applied to the assembly. The ultrasonic welding process was performed twice to create a sewing ring flange thickness of approximately 2 mm with an outer diameter of 33 mm. The final valve assembly is shown illustratively and generally indicated at 1100 in FIG. 30.

The final leaflet was comprised of 28.22% fluoropolymer by weight with a thickness of 50.3 μm. Each leaflet had 26 layers of the composite and a ratio of thickness/number of layers of 1.93 μm.

The resulting valve assembly 1100 includes leaflets 1102 formed from a composite material with more than one fluoropolymer layer having a plurality of pores and an elastomer present in substantially all of the pores of the more than one fluoropolymer layer. Each leaflet 1102 is movable between a closed position, shown illustratively in FIG. 30A, in which blood is substantially prevented from flowing through the valve assembly, and an open position, shown illustratively in FIG. 30B, in which blood is allowed to flow through the valve assembly. Thus, the leaflets 1102 of the valve assembly 1100 cycle between the closed and open positions generally to regulate blood flow direction in a human patient.

The hydrodynamic performance was measured prior to accelerated wear testing. The performance values were; EOA=1.88 cm$^2$ and regurgitant fraction=10.86%. No observable damage has been recorded during durability testing with the number of cycles nearing 100 million.

Example 4b

In exemplary embodiments, a heart valve was constructed with a valve frame, strain relief, sewing ring, and first three layers of composite material, as described above in Example 4a, and utilizing a leaflet material comprising a final composite having a mass per area of 11.80 g/m$^2$, 9.74% fluoropolymer by weight, a dome burst strength of 17.3 KPa, and thickness of 5.78 μm after the coating steps.

Six additional layers of the composite material were wrapped around the combined molds of FIG. 26a with the membrane orientation as described in Example 4a.

The assembly was molded, thermally processed, and trimmed as described in Example 4a.

The final leaflet was comprised of 9.74% fluoropolymer by weight with a thickness of 52.0 μm. Each leaflet had 9 layers of the composite material and a ratio of thickness/number of layers of 5.78 μm.

The hydrodynamic performance was measured prior to accelerated wear testing. The performance values were; EOA=2.05 cm$^2$ and regurgitant fraction=11.71%. Observable damage was recorded as frame detachment during durability testing at about 6 million cycles.

Example 4c

In exemplary embodiments, a heart valve was constructed with a valve frame that was laser machined and coated with FEP, as described above in Example 4a, and further provided with a cushion member attached to the perimeter of the frame adjacent to leaflets regions to minimize stress related to direct contact between the frame and the leaflet.

Figure 31:
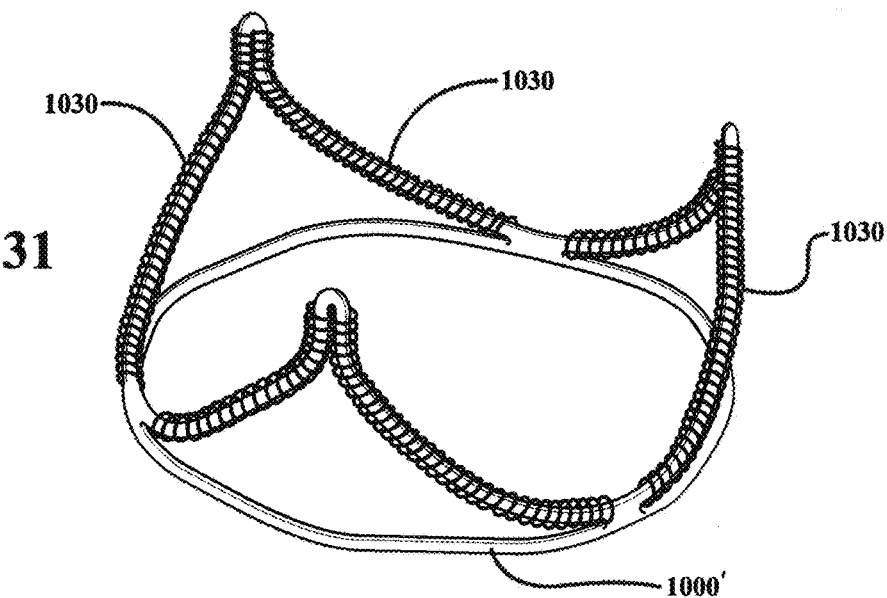
FIG. 31 is a perspective view of a non-collapsible stent frame or support structure of FIG. 24 with a cushion member covering a perimeter of the structure, in accordance with an embodiment.

A 0.5 mm thick ePTFE fiber was helically wrapped onto a 1.143 mm mandrel with a pitch that eliminated space between wraps. Two layers of 2.54 μm FEP film was wrapped over ePTFE fiber coils and was then subjected to a thermal treatment by placing it in a forced air oven set to 320° C. for approximately three minutes. The material was brought back to room temperature via air cooling at room temperature. The ePTFE fiber formed a contiguous coil tube once removed from the mandrel. The coiled tube was cut into three 125 mm lengths and slit axially leaving only 5 mm intact as a coiled tube. Each of the three lengths was slid onto FEP-coated frame to form the frame 1000' having the cushion member 1030 attached thereto for minimizing stress related to direct contact between the frame 1000' and the leaflet (not shown), as depicted in FIG. 31.

A valve frame, strain relief, sewing ring, leaflet material, and first layer of composite material were prepared, as described in Example 4a, encapsulating the cushion members and frame. The leaflet material was prepared such that after the coating steps, the final composite had a mass per area of 25.48 g/m$^2$, 8.91% fluoropolymer by weight, a dome burst strength of 31.7 KPa, and thickness of 13.08 μm.

Three additional layers of the composite material were wrapped around the combined molds with the membrane orientation, as described in Example 4a.

Figure 32:
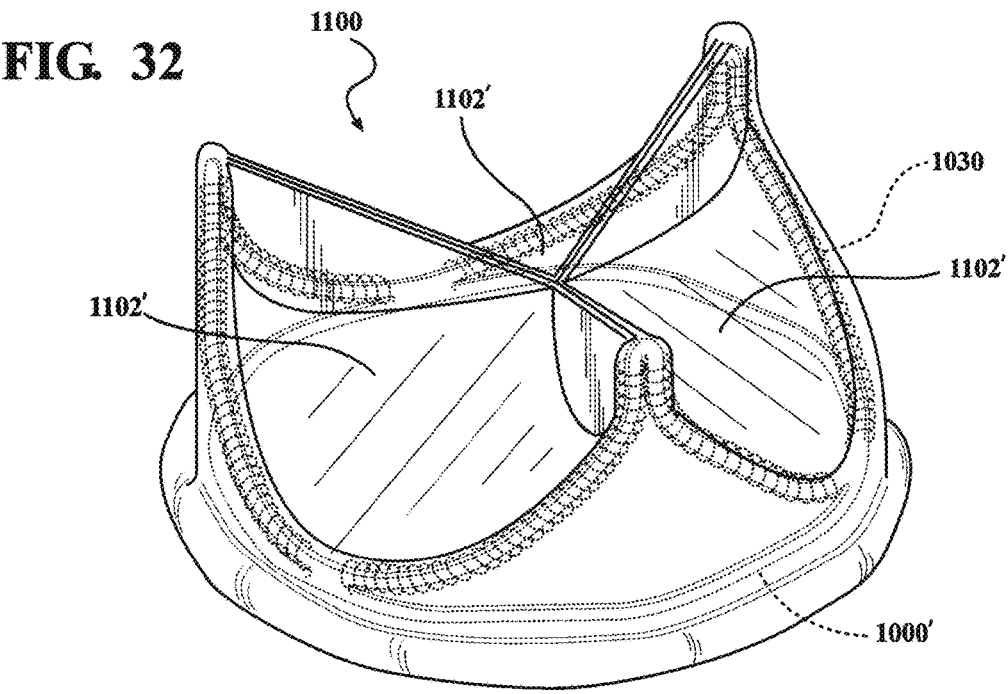
FIG. 32 is a perspective view of a completed valve having leaflets coupled to and supported on a frame or support structure with a cushion member covering a perimeter of the support structure, a strain relief, and a sewing flange, in accordance with an embodiment.

The assembly was molded with cushion members, thermally processed, and trimmed as described in Example 4a to form the final valve assembly 1100' having the frame 1000' and the cushion member 1030 attached thereto for minimizing stress related to direct contact between the frame 1000' and the leaflets 1102', as depicted in FIG. 32.

The final leaflet was comprised of 8.91% fluoropolymer by weight with a thickness of 52.3 μm. Each leaflet had 4 layers of the composite and a ratio of thickness/number of layers of 13.08 μm.

The hydrodynamic performance was not measured prior to accelerated wear testing. Observable damage was recorded as a hole formation in leaflet during durability testing at about 12.4 million cycles.

Example 5

In exemplary embodiments, a heart valve was constructed having a valve frame, strain relief, sewing ring, leaflet material, and first three layers of composite material were prepared, as described in Example 4a, and further having the final leaflet described immediately below.

Fifteen additional layers of the composite material were wrapped around the combined molds and with the membrane orientation as described in Example 4a.

The assembly was molded, thermally processed, and trimmed as described in Example 4a.

The final leaflet was comprised of 9.74% fluoropolymer by weight with a thickness of 98.3 μm. Each leaflet had 18 layers of the composite and a ratio of thickness/number of layers of 5.46 μm.

The hydrodynamic performance was measured prior to accelerated wear testing. The performance values were; EOA=1.73 cm$^2$ and regurgitant fraction=11.71%. Observable damage was recorded as frame detachment and leaflet delamination during durability testing at about 100 million cycles.

Example 6

In exemplary embodiments, a heart valve was constructed having a valve frame, cushion layer, strain relief, and sewing ring were prepared, as described in Example 4c, and further having the final leaflet as described immediately below.

A leaflet material was then prepared. The ePTFE membrane had a mass per area of 0.31 g/m$^2$, a bubble point of 0.11 MPa, a thickness of about 127 nm, a matrix tensile strength of 442.0 MPa in the longitudinal direction and 560.0 MPa in the transverse direction. This membrane was imbibed with a fluoroelastomer as described in Example 4a. After the coating steps, the final ePTFE/fluoroelastomer or composite had a mass per area of 1.04 g/m$^2$, 29.9% fluoropolymer by weight, a dome burst strength of 9.9 KPa, and thickness of 0.52 μm.

Ninety-five layers of the composite was wrapped around the combined molds with the membrane oriented such that the matrix tensile strength of 442 MPa is oriented axially and the elastomer rich side of the membrane facing toward the molds as described in Example 4a.

The assembly was molded, thermally processed, and trimmed as described in Example 4a.

The final leaflet was comprised of 29.00% fluoropolymer by weight with a thickness of 49.7 μm. Each leaflet had 95 layers of the composite and a ratio of thickness/number of layers of 0.52 μm.

The hydrodynamic performance was measured prior to accelerated wear testing. The performance values were; EOA=2.19 cm$^2$ and regurgitant fraction=9.7%. No observable damage has been recorded during durability testing.

Example 7

In other exemplary embodiments, a heart valve having polymeric leaflets was formed from a composite material having an expanded fluoropolymer membrane and an elastomeric material; joined to a metallic balloon expandable stent frame; and was constructed according to the following process:

A metallic balloon expandable stent frame was laser machined from a length of MP35N alloy annealed tube with an outside diameter of 26.00 mm and a wall thickness of 0.60 mm. A pattern was cut into the tube to form a cylindrically-shaped cut stent frame, also referred herein as a support structure, as illustrated and generally indicated at 600 in the flat plane view of FIG. 6a. The support structure 600, includes a plurality of small closed cells 602, a plurality of large closed cells 604, and a plurality of leaflet closed cells 606. Note that one of the plurality of leaflet closed cells 606 appears as an open cell in FIG. 6A due to the flat plane view. The cells 602, 604, 606 are generally arranged along rows forming the annular shape of the support structure 600.

The surface of the metallic frame was prepared as described in Example 4a.

Figure 33A:
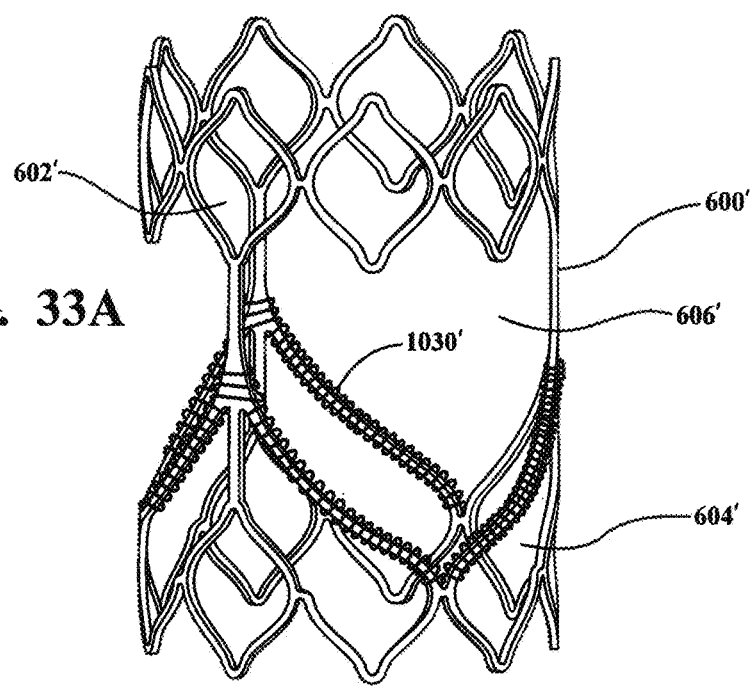
FIG. 33A is a perspective view of a collapsible stent frame or support structure of FIG. 6A with a cushion member covering the regions of the structure to which leaflets are attached, in accordance with an embodiment.
Figure 33B:
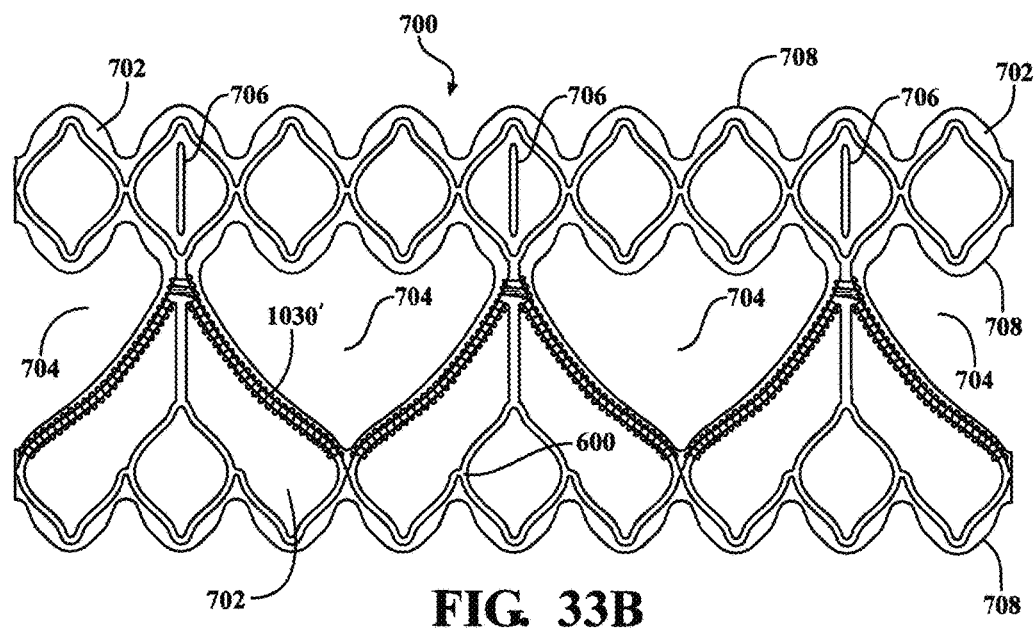
FIG. 33B is a flattened plane view of the support structure of FIG. 6A with a polymer coating encapsulating the cushion members, in accordance with an embodiment.
Figure 34:
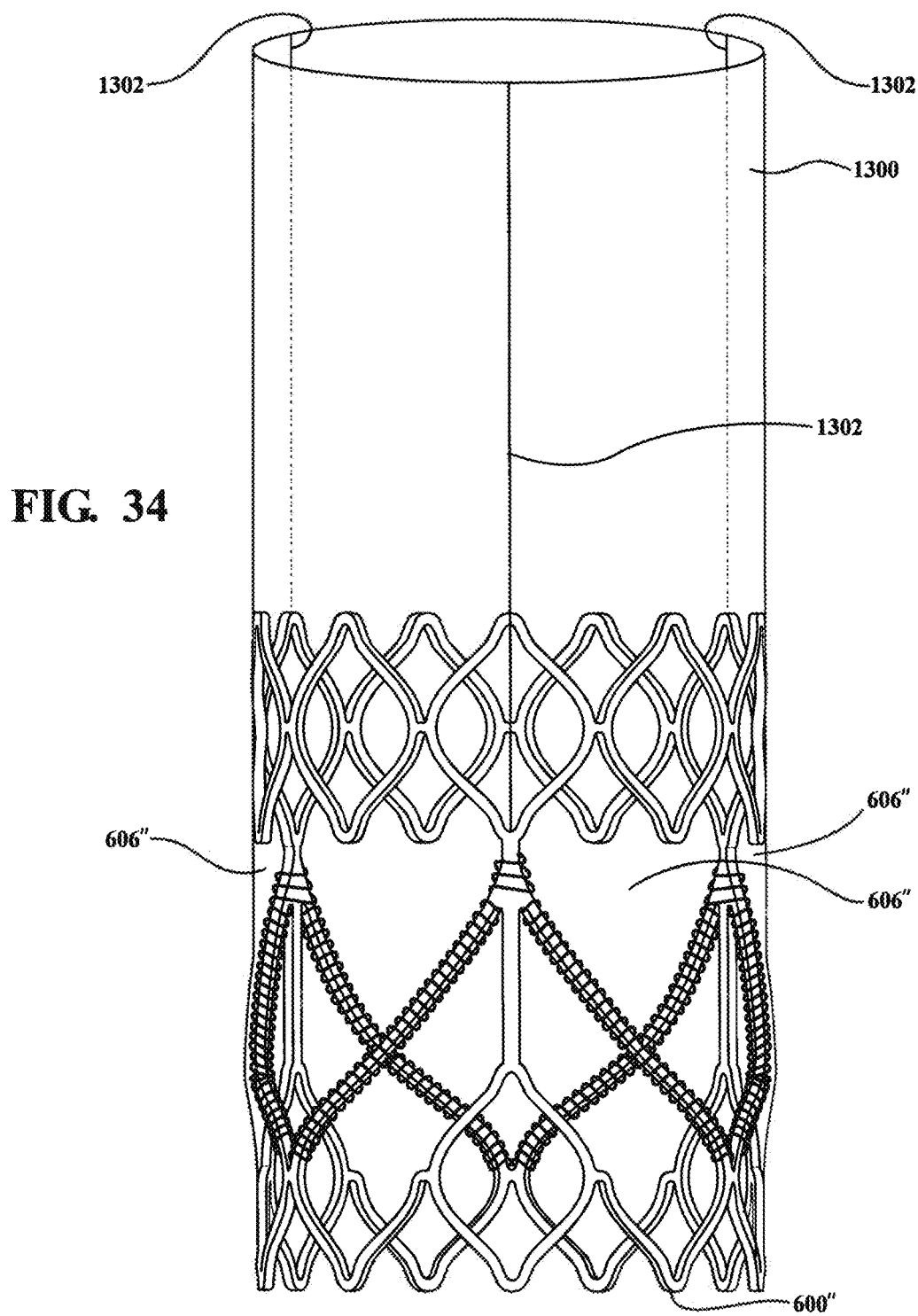
FIG. 34 is a perspective view of the collapsible stent frame and cushion members of FIGS. 33A and 33B with leaflet material wrapped as cylinder over the exterior of the frame with three axial slits, in accordance with an embodiment.

An ePTFE laminate was attached to the frame with a strain relief, in a manner similar to Example 4c. A 24 mm diameter cylindrical mandrel was wrapped with a single layer of Kapton® polyimide film (DuPont) and held in place by an adhesive strip of Kapton® tape over the length of the overlapping seam. Two layers of a substantially nonporous ePTFE having a layer of FEP disposed along an outer surface or side thereof was wrapped with the FEP facing away from the mandrel surface; two layers of FEP, 3.6 µm thick, were then wrapped over this. The metallic balloon expandable stent frame was aligned coaxially over the wrapped mandrel. An additional two layers of FEP were wrapped over the stent on the mandrel encapsulating the stent and strain relief. Two layers of a substantially porous ePTFE were wrapped over the FEP followed by an additional three layers of FEP wrapped over ePTFE. The entire assembly was subjected to a thermal treatment by placing it in a forced air oven set to 375° C. for twenty minutes and returned to room temperature by immediate water quench upon removal from the oven. The laminate was trimmed from regions of the frame to expose three windows for leaflet attachment as depicted in FIG. 33b.

A leaflet material was then prepared as described in Example 6. The ePTFE membrane had a mass per area of 0.29 g/m$^2$, a bubble point of 0.11 MPa, a thickness of about 158 nm, a matrix tensile strength of 434.0 MPa in the longitudinal direction and 646.0 MPa in the transverse direction. This membrane was imbibed with a fluoroelastomer as described in Example 4a. After the coating process, the final ePTFE/fluoroelastomer composite had a mass per area of 0.94 g/m$^2$, 30.3 fluoropolymer by weight, a dome burst strength of 4.14 KPa, and thickness of 0.44 µm.

Seventeen layers of the composite was wrapped around a 26 mm mandrel. The composite was oriented so that the matrix tensile strength of 434 MPa was placed axially and the elastomer rich side of the membrane was facing toward the mandrel as described in Example 4a.

The subassembly containing the frame and strain relief was positioned on the mandral over the 17 layers. An additional 40 layers of composite were wrapped, sandwiching the frame between both layers of composite creating a total of 57 layers of composite. The mandrel, leaflet layers, and frame were covered by an impermeable layer and sealed at both ends. Using a pressure vessel, the assembly was heated to about 285° C. at 75 psi for about 23 minutes and then allowed to cool to room temperature while under pressure. The valve assembly was removed from the mandrel. The free edge of the leaflet was created by slicing the laminate in an arc at each of the three leaflet closed cells 606 on the frame freeing the leaflet to open and close under fluid pressure. The leaflets were molded into final shape using leaflet molding tools described in FIGS. 5A-5B. Each of the leaflet molding tools was coaxially aligned to the base tool to allow for a cover to be applied to the exterior of the frame.

A frame cover material was then prepared as described in Example 6. The ePTFE membrane had a mass per area of 0.86 g/m$^2$, a bubble point of 0.11 MPa, a thickness of about 900 nm, a matrix tensile strength of 376.0 MPa in the longitudinal direction and 501.0 MPa in the transverse direction. This membrane was imbibed with a fluoroelastomer as described in Example 4a. After the coating process, the final ePTFE/fluoroelastomer composite had a mass per area of 7.05 g/m$^2$, 14.1% fluoropolymer by weight, a dome burst strength of 13.1 KPa, and thickness of 3.28 µm.

Fifteen layers of the composite was wrapped around the valve frame while being held in the shape set tooling. The composite was oriented so that the matrix tensile strength of 501 MPa was placed axially and the elastomer rich side of the membrane was facing toward the mandrel as described in Example 4a. The final cover was comprised of 14.1% fluoropolymer by weight with a thickness of 49.2 µm.

The assembly was molded, thermally processed in an open atmosphere convection oven at 250° C. for 1 hour. The valve was then removed from the molding tooling.

The final leaflet was comprised of 30.3% fluoropolymer by weight with a thickness of 25.0 µm. Each leaflet had 57 layers of the composite and a ratio of thickness/number of layers of 0.44 µm.

A plurality of longitudinally extending slits 1302 were formed in the tube 1300 resulting in the formation of a plurality of tabs 1304. The slits can be formed by any suitable method known to those having ordinary skill in the art, such as by cutting with a blade.

The leaflet tools (not shown) were then slid out from underneath the tube 1300.

Figure 35:
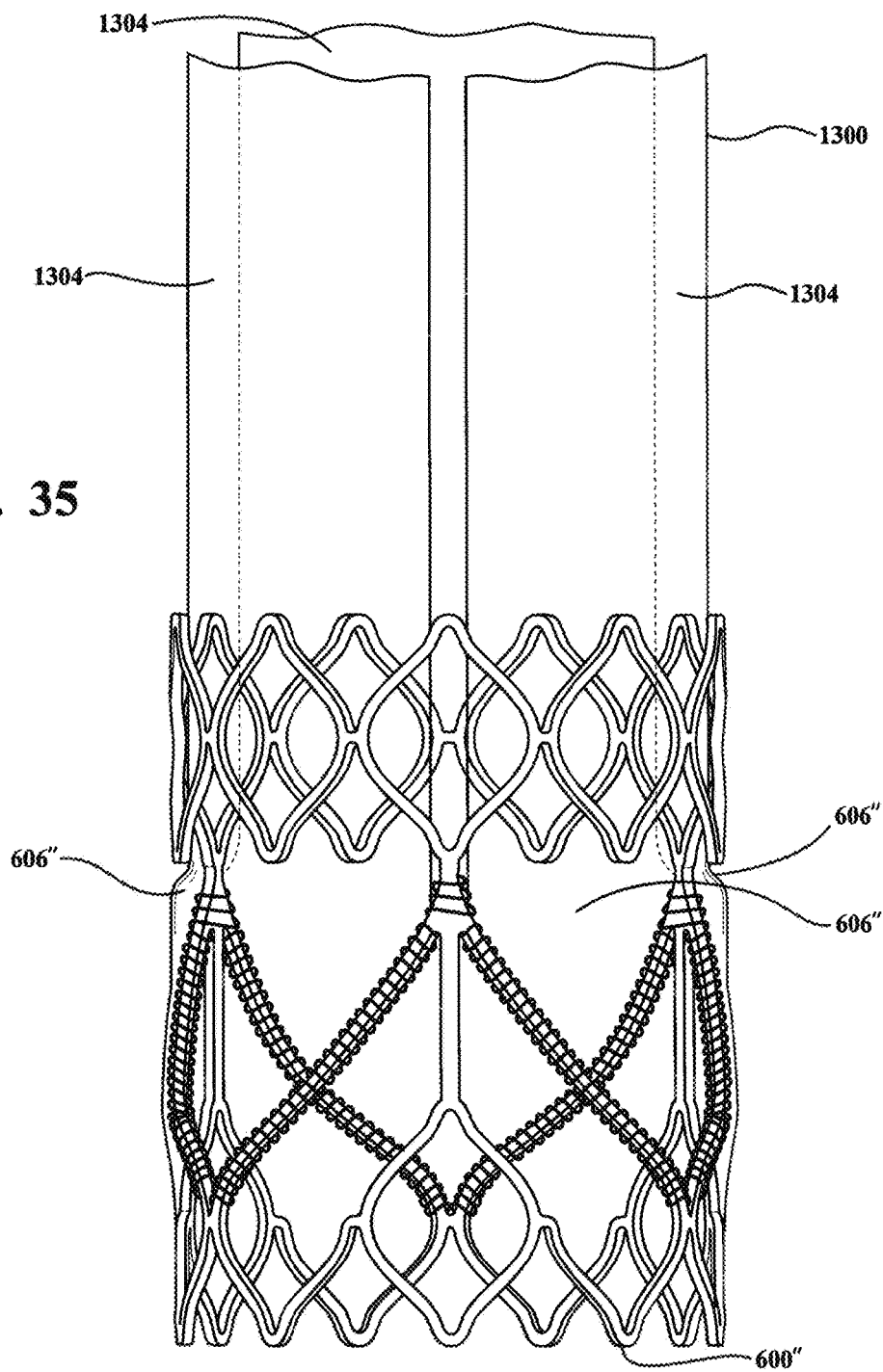
FIG. 35 is a perspective view of FIG. 34 with three tabs of leaflet material internalized to stent frame through individual openings, in accordance with an embodiment.

The three tabs 1304 created by forming the slits 1302 in the tube 1300 were then fed inwardly through respective windows or cells formed in the frame, as depicted in FIG. 35. Each of the leaflet tools was coaxially aligned to the base tool to allow the inwardly fed tabs 1304 of the tube 1300 from the previous step to be positioned and compressed between the leaflet tools and the female tri-leaflet mold surface configuration of the base tool. The combined tool assembly comprising the leaflet and base tools, composite or leaflet material, and frame was then mounted between fixed and translational portions of a fixture. Both radial and axial compression were applied by radially clamping the leaflet tools while simultaneously applying an axial load with the translational end of the fixture.

Figure 36:
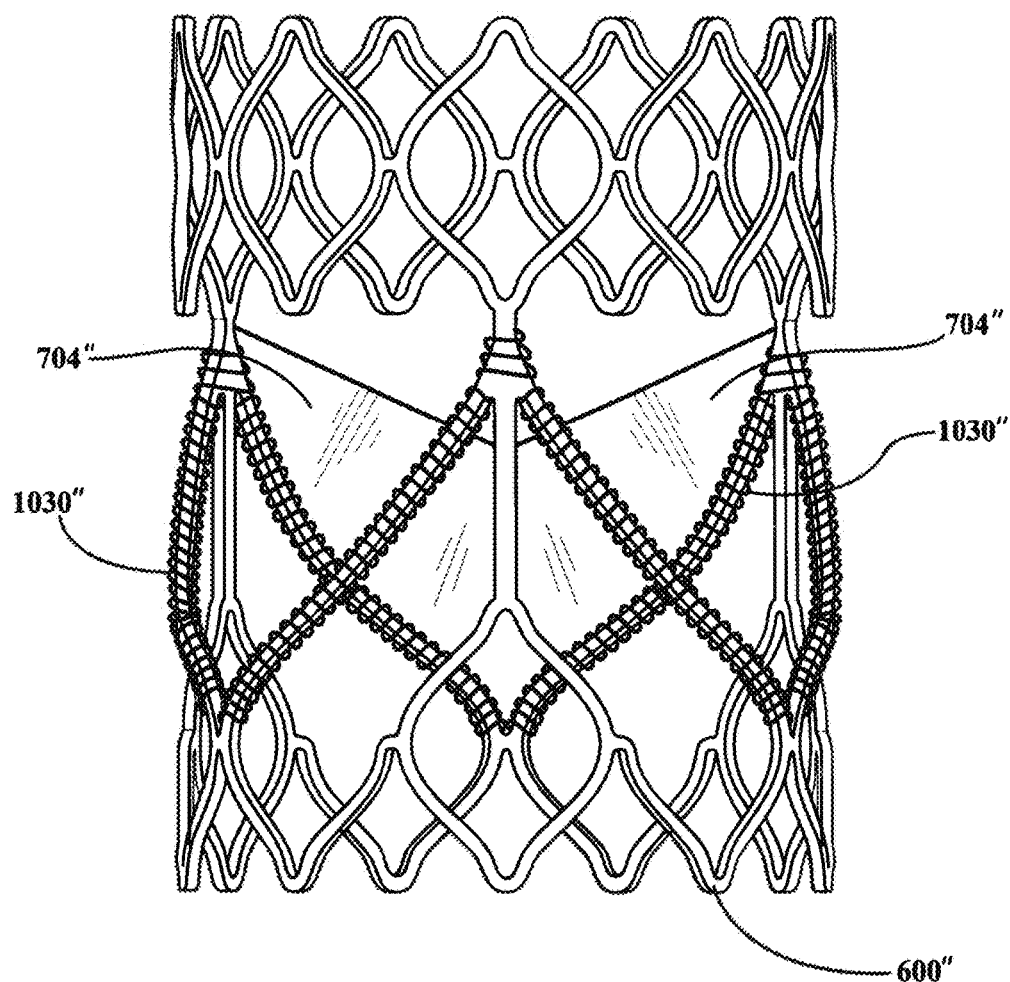
FIG. 36 is a perspective view of a completed valve having leaflets coupled to and supported on a collapsible frame with a cushion member at leaflet attachment sites of structure and a strain relief, in accordance with an embodiment.

The assembly was molded, thermally processed, and trimmed as described in Example 4a. The final valve assembly having the metallic balloon expandable stent frame 600", cushion members 1030", and leaflets 704" is shown in FIG. 36.

The final leaflet was comprised of 33.70% fluoropolymer by weight with a thickness of 16.0 µm. Each leaflet had fifty layers of the composite and a ratio of thickness/number of layers of 0.32 µm.

The hydrodynamic performance was measured prior to use. The performance values were; EOA=2.0 cm$^2$ and regurgitant fraction=15.7%. No observable damage has been recorded during durability testing.

Following construction and testing, the valve was sent to Carmeda Corporation (Carmeda AB, Stockholm Sweden) for heparin coating. After coating, the completed valve was mounted on a balloon catheter and crushed to a reduced diameter of 20 French using a mechanical iris crushing apparatus. The catheter-mounted valve was forwarded to Sterigenics corp. (Salt lake city UT) for ethylene oxide sterilization. Using sterile technique the valve was inserted through a 20F sheath into the surgically exposed iliac artery of an anesthetized 4 month old, 25 Kg Ramboulet sheep. The catheter was advanced though the inferior vena cava, through the right atrium and into the pulmonary artery trunk. It was deployed over the native pulmonary valve and actuated by pressurizing the balloon catheter to 4 atmospheres. Following angiogram and pressure measurements, the catheter was withdrawn and the animal recovered. The valve, referred below as the explanted valve, remained in place for one month, replacing the function of the native pulmonary valve.

The hydrodynamic performance of the explanted valve was measured after explant and compared with a control valve. The explanted valve was explanted, fixed in formalin solution, digested in sodium hydroxide, rinsed in ethanol, acetone and distilled water prior to testing. The control valve was a duplicate of the explanted valve that was compressed to the delivery diameter, redeployed on a balloon catheter and tested. Each valve was tested under both aortic and pulmonary flow conditions in a ViVitro real time tester. No degradation in hemodynamic performance was observed.

The performance values for the explanted and control valves are listed in Table 5.

TABLE 5

|  | Pressure Drop (mm Hg) | EOA (cm$^2$) | Closing volume (ml) |
| --- | --- | --- | --- |
| Aortic conditions, 70 bpm, 5 liter/min, 125/89 peak bp |  |  |  |
| Control | 8.9 | 1.99 | 4.12 |
| Explanted valve | 6.8 | 2.12 | 2.69 |
| Pulmonary conditions, 70 bpm, 5 liter/min, 26/15 peak bp |  |  |  |
| Control | 9.5 | 1.82 | 2.25 |
| Explanted | 8.9 | 1.76 | 2.25 |

Example 8

In exemplary embodiments, a heart valve having polymeric leaflets joined to a rigid metallic frame was constructed according to the following process:

A valve support structure or frame 960 was laser cut from a length of 316 stainless steel tube with an outside diameter of 25.4 mm and a wall thickness of 0.5 mm in the shape shown in FIG. 19. In the embodiment shown, the frame 960 extends axially between a bottom end 962 and an opposite top end defined generally by a plurality of axially extending, generally spire shaped posts 964 corresponding to the number of leaflets in the intended finished valve assembly (not shown). A parabolically shaped top edge 968 extends between adjacent posts 964. In the specific embodiment shown, three posts 964 and three top edges 968 form the top end of the frame 960. The corners of the frame that would be in contact with the leaflet material were rounded using a rotary sander and hand polished. The frame was rinsed with water and then plasma cleaned using a PT2000P plasma treatment system, Tri-Star Technologies, El Segundo, Calif., USA.

A cushion member is provided between at least a portion of the frame and at least a portion of the leaflet to minimize stress related to direct contact between the frame and the leaflet. A composite fiber of ePTFE and silicone was created by first imbibing an ePTFE membrane with silicone MED-6215 (NuSil, Carpinteria, Calif., USA), slitting it to a width of 25 mm, and rolling into a substantially round fiber. The ePTFE used in this fiber was tested in accordance with the methods described in the Appendix. The ePTFE membrane had a bubble point of 217 KPa, a thickness of 10 µm, a mass per area of 5.2 g/m$^2$, a porosity of 78%, a matrix tensile strength in one direction of 96 MPa, and a matrix tensile strength of 55 MPa in an orthogonal direction. The composite fiber 966 was wrapped around each of the posts 964 of the valve frame 960 as shown in FIG. 20.

A mandrel 970 was formed using stereolithography in a shape shown in FIG. 21. The mandrel 970 has a first end 972 and an opposite second end 974, and extends longitudinally therebetween. The mandrel 970 has an outer surface 980 having three (two shown) generally arcuate, convex lobes 982, each generally for forming leaflets (not shown) of a finished valve assembly (not shown). The outer surface 980 also includes a frame seating area 984 for positioning the valve frame (960 in FIG. 19) relative to the lobes 982 prior to formation of the valve leaflets onto the valve frame.

The mandrel 970 was then spray coated with a PTFE mold release agent. Four layers of ePTFE membrane were wrapped around the mandrel. The ePTFE membrane was tested in accordance with the methods described in the Appendix. The ePTFE membrane had a mass per area of 0.57 g/m$^2$, a porosity of 90.4%, a thickness of about 2.5 µm, a bubble point of 458 KPa, a matrix tensile strength of 339 MPa in the longitudinal direction and 257 MPa in the transverse direction. MED-6215 was wiped onto the ePTFE and allowed to wet into and substantially fill the pores of the ePTFE. Excess MED-6215 was blotted off and the valve frame 960 with the composite fiber 966 wrapped posts 964 was positioned on the mandrel 970 along the frame seating area 984, as shown in FIG. 22. Silicone MED-4720, NuSil, Carpinteria, Calif., USA was placed along the top edges 968 of the frame 960 and along the posts 964 of the frame 960 to create a strain relief within the leaflet (not shown). Thirty additional layers of the same ePTFE were wrapped around the frame 960 and mandrel 970. Additional MED-6215 was wiped onto the ePTFE and allowed to wet into and substantially fill the pores of the ePTFE. 8 layers of ePTFE membrane were wrapped around the frame 960 and mandrel 970. The ePTFE used was tested in accordance with the methods described in the Appendix. The ePTFE membrane had a bubble point of 217 KPa, a thickness of 10 µm, a mass per area of 5.2 g/m$^2$, a porosity of 78%, a matrix tensile strength in one direction of 96 MPa, and a matrix tensile strength of 55 MPa in an orthogonal direction. These layers absorbed any excess silicone during the molding process and were removed after the silicone had cured.

Silicone rubber forms (not shown) molded with one surface exactly matching the inverse shape of the mandrel surface were previously fabricated for each of the 3 leaflet-forming features. These forms were spray coated with PTFE mold release and then mated to the matching feature of the mandrel. Approximately 50 wraps of an ePTFE fiber (not shown) were wound around the silicone forms to apply generally radial pressure to the valve against the mandrel.

This assembly was then placed in an oven at 100° C. for 1 hour to cure the silicone. After cooling, the fiber and silicone forms were removed, the 8 layers of blotter ePTFE were peeled away and discarded, and the resulting valve (not shown) was slid off of the mandrel. The posts were trimmed using wire cutters and the excess length of leaflet material and excess length of material at the base of the frame was carefully trimmed using scissors to form a completed valve assembly, which is shown and generally indicated at 990 in FIG. 23. Thus, in one embodiment, the valve assembly 990 was formed having the frame or support structure 960; a plurality of leaflets 992 supported on the support structure 960 and movable between open and closed positions to regulate blood flow through the valve assembly 990; and a cushion member 1030 located between at least a portion of the support structure 960 and at least a portion of each leaflet 992 to minimize stress in the leaflets due to the coupling and/or proximity of the leaflets to the support structure. In another embodiment, the cushion member is formed from a composite material with at least one fluoropolymer layer having a plurality of pores and an elastomer present in substantially all of the pores, as described above.

It should be appreciated that support structures other than as specifically shown in the figures may be utilized. Further, cushion members may be utilized anywhere along the support structure as necessary to minimize stress in the leaflets due to the coupling and/or proximity of the leaflets to the support structure. For example, cushion member(s) may be coupled to the support structure along the parabolically shaped top edge.

It should also be appreciated that the cushion members may be formed as sheets and wrapped around desired locations along the support structure, or be formed from fibers of various cross sectional shapes and sizes.

It should also be appreciated that the cushion members may be formed as tubes and slid over the ends of the support structure, or be slit longitudinally and positioned around the desired location along the support structure.

The leaflets of the complete valve assembly were measured and determined to have an average thickness at the center of each leaflet of about 48 μm.

The final leaflet was comprised of 24.00% fluoropolymer by weight with a thickness of 48.0 μm. Each leaflet had 48 layers of the composite and a ratio of thickness/number of layers of 1.07 μm.

The hydrodynamic performance was measured prior to accelerated wear testing. The performance values were; EOA=2.4 cm$^2$ and regurgitant fraction=12.5%. No observable damage has been recorded during durability testing with the number of cycles of about 150 million.

The hydrodynamic performance of the valves described in Examples 4a, 4b, 5, 6, 7, and 8 was characterized on a real-time pulse duplicator that measured typical anatomical pressures and flows across the valve, generating an initial or "zero fatigue" set of data for that particular valve assembly.

Following flow performance characterization, the valve assemblies were then removed from the flow pulse duplicator system and placed into a high-rate fatigue or durability tester. The valves were continuously monitored to ensure they held pressure when closed and to assess when any damage in the form of frame detachment, tears, holes, or delamination occurred. Where appropriate, the hydrodynamic performance of valves were again measured post durability testing at about 100 million cycles and recorded.

The results of the performance characterizations are listed in FIG. 43, Table 6.

The data presented in Examples 4a, 4b, 4c, 5, 6, 7 & 8 and summarized in Tables 4, 5 and 6 support the observation of general durability and hydrodynamic performance trends associated with different leaflet configurations when thickness, percent fluoropolymer by weight, and number of layers are varied. The number of Examples presented support these observations by allowing comparisons to be made when differences due to frame type and cushion members are used in the individual valve construction.

Examples 4b and 4c are configurations where leaflet thickness and percent fluoropolymer by weight are equal and illustrate that low layer numbers lead to reduced durability. The failure mode of Example 4b of frame detachment was mitigated by using a cushion member which in turn doubled the time to failure, however the failure mode switched from frame detachment to hole formation within the leaflet. Both Examples 4a and 4b had durability failures well below what is acceptable.

Examples 4b and 5 provide a comparison where percent fluoropolymer by weight is held constant and a difference in layer number and therefore leaflet thickness are measured. Both Examples have the same valve construction without the cushion members which have been shown above to mitigate frame detachment. The effect of doubling the number of layers from 9 to 18 and therefore increasing the leaflet thickness from about 52 μm to about 98 μm improved the number of cycles to frame detachment by nearly an order of magnitude from 12 million to 100 million.

Example 4a, which again is of similar construction to Examples 4b, where leaflet thickness of about 50 μm is held constant and varying the percent fluoropolymer by weight from about 10% for Example 4b to about 30% for Example 4a enabled the creation of a thinner composite and therefore many more layers (26) for the same leaflet thickness. Although some free edge delamination has been observed for Example 4a near the high strain region of the triple point, the valve is still viable as determined by hydrodynamic characterization with 100 million cycles accrued as shown in Table 5.

In examples 6 and 7, the improved bending behavior of these thin and high layer configurations generally indicate that improved durability follows when compared to lower layer number constructions due to the reduction in creases and wrinkles thought the duty cycle as illustrated in FIGS. 41A and 41B.

Additionally, Example 8 illustrates that similar durability can be achieved with different elastomers of high layer configurations as demonstrated by Examples 6 and 7.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

APPENDIX

As used in this application, matrix tensile strength refers to the tensile strength of a porous fluoropolymer specimen under specified conditions. The porosity of the specimen is accounted for by multiplying the tensile strength by the ratio of density of the polymer to the density of the specimen.

As used herein the term "membrane" refers to a porous fluoropolymer article, "composite" refers to imbibed porous fluoropolymers, and a "leaflet" is a component of an implantable article for regulating blood flow direction. Leaflets of the present embodiments are one or more layers of a composite.

The term "imbibe" used herein refers to any process used to at least partially fill pores with a secondary material.

For porous fluoropolymer leaflets having pores substantially filled with elastomer, the elastomer can be dissolved or degraded and rinsed away using an appropriate solvent in order to measure desired properties.

As the term "elastomer" is used herein it defines a polymer, mixture of polymers, or mixture of one or more polymers with one or more non-polymeric components that has the ability to be stretched to at least 1.3 times its original length and to retract rapidly to approximately its original length when released. The term "elastomeric" is intended to describe a property whereby a polymer displays stretch and recovery properties similar to an elastomer, although not necessarily to the same degree of stretch and/or recovery.

As the term "thermoplastic" is used herein it defines a polymer that softens when exposed to heat and returns to its original condition when cooled to room temperature. Such a polymer can be made to soften, flow or take on new shapes, without significant degradation or alteration of the polymer's original condition, by the application of heat or heat and pressure. In contrast to a thermoplastic polymer, a "thermoset" polymer is hereby defined as a polymer that solidifies or "sets" irreversibly when cured. A determination of whether a polymer is a "thermoplastic" polymer within the meaning of the present embodiments can be made by slowly elevating the temperature of a stressed specimen and watching for deformation. If the polymer can be made to soften, flow, or take on a new shape, without significant degradation or alteration of the polymers original chemical condition, then the polymer is considered to be a thermoplastic. If only small amounts of material are available it may be necessary to use a hot stage microscope for this determination.

One measure of the quality of a valve is the effective orifice area (EOA), which can be calculated as follows: $EOA(cm^2) = Q_{rms}/(51.6*(\Delta P)^{1/2})$ where $Q_{rms}$ is the root mean square systolic/diastolic flow rate ($cm^3/s$) and $\Delta P$ is the mean systolic/diastolic pressure drop (mmHg).

Another measure of the hydrodynamic performance of a valve is the regurgitant fraction, which is the amount of fluid or blood regurgitated through the valve divided by the stroke volume.

As used in this application, the surface area per unit mass, expressed in units of $m^2/g$, was measured using the Brunauer-Emmett-Teller (BET) method on a Coulter SA3100Gas Adsorption Analyzer, Beckman Coulter Inc. Fullerton Calif., USA. To perform the measurement, a sample was cut from the center of the expanded fluoropolymer membrane and placed into a small sample tube. The mass of the sample was approximately 0.1 to 0.2 g. The tube was placed into the Coulter SA-Prep Surface Area Outgasser (Model SA-Prep, P/n 5102014) from Beckman Coulter, Fullerton Calif., USA and purged at about 110° C. for about two hours with helium. The sample tube was then removed from the SA-Prep Outgasser and weighed. The sample tube was then placed into the SA3100 Gas adsorption Analyzer and the BET surface area analysis was run in accordance with the instrument instructions using helium to calculate the free space and nitrogen as the adsorbate gas.

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. Using the Capwin software version 7.73.012 the following parameters were set as specified in the table below.

| Parameter | Set Point |
| --- | --- |
| Maxflow ($cm^3/m$) | 200000 |
| Bublflow($cm^3/m$) | 100 |
| F/PT (old bubltime) | 50 |
| Minbpress (PSI) | 0 |
| Zerotime (sec) | 1 |

-continued

| Parameter | Set Point |
| --- | --- |
| V2incr(cts) | 10 |
| Preginc (cts) | 1 |
| Pulse delay(sec) | 2 |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp(PSI) | 1 |
| Sartf ($cm^3/m$) | 500 |

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

The presence of elastomer within the pores can be determined by several methods known to those having ordinary skill in the art, such as surface and/or cross section visual, or other analyses. These analyses can be performed prior to and after the removal of elastomer from the leaflet.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho = m/w*l*t$, in which: $\rho$=density ($g/cm^3$): m=mass (g), w=width (cm), l=length (cm), and t=thickness (cm. The average of three measurements was reported.

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For longitudinal measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness measured using the Käfer FZ1000/30 snap gauge. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), wherein the bulk density of the PTFE was taken to be about 2.2 $g/cm^3$. Flexural stiffness was measured by following the general procedures set forth in ASTM D790. Unless large test specimens are available, the test specimen must be scaled down. The test conditions were as follows. The leaflet specimens were measured on a three-point bending test apparatus employing sharp posts placed horizontally about 5.08 mm from one another. An about 1.34 mm diameter steel bar weighing about 80 mg was used to cause deflection in the y (downward) direction, and the specimens were not restrained in the x direction. The steel bar was slowly placed on the center point of the membrane specimen. After waiting about 5 minutes, the y deflection was measured. Deflection of elastic beams supported as above can be represented by: $d=F*L^3/48*El$, where F (in Newtons) is the load applied at the center of the beam length, L (meters), so $L=\frac{1}{2}$ distance between suspending posts, and El is the bending stiffness (Nm). From this relationship the value of El can be calculated. For a rectangular cross-section: $I=t^3*w/12$, where l=cross-sectional moment of inertia, t=specimen thickness (meters), w=specimen width (meters). With this relationship, the average modulus of elasticity over the measured range of bending deflection can be calculated.

What is claimed is:

1. A prosthetic valve, comprising:
a leaflet comprising more than one layer of a composite material having at least one fluoropolymer layer having a plurality of pores and an elastomer substantially filling the pores of the at least one fluoropolymer layer, the composite material comprising less than about 80% fluoropolymer by weight, the more than one layer of composite material being coupled together via the elastomer.

2. The prosthetic valve as set forth in claim 1, the leaflet having a ratio of leaflet thickness (μm) to number of fluoropolymer layers of less than about 5.

3. The prosthetic valve as set forth in claim 2, wherein the ratio of leaflet thickness (μm) to number of fluoropolymer layers of less than about 3.

4. The prosthetic valve as set forth in claim 2, wherein the ratio of leaflet thickness (μm) to number of fluoropolymer layers of less than about 1.

5. The prosthetic valve as set forth in claim 2, wherein the ratio of leaflet thickness (μm) to number of fluoropolymer layers of less than about 0.5.

6. The prosthetic valve as set forth in claim 1, wherein the leaflet encompasses a radiopaque element.

7. The prosthetic valve as set forth in claim 1, wherein the leaflet has a bending modulus of less than about 100 MPa.

8. The prosthetic valve as set forth in claim 1, wherein the leaflet is operatively coupled to a support frame and movable between closed and open configurations relative to the support frame.

9. The prosthetic valve as set forth in claim 8, wherein the support frame is selectively diametrically adjustable for endovascular delivery and deployment at a treatment site.

10. The prosthetic valve as set forth in claim 1, wherein the composite material comprises less than about 70% fluoropolymer by weight.

11. The prosthetic valve as set forth in claim 1, wherein the composite material comprises less than about 60% fluoropolymer by weight.

12. The prosthetic valve as set forth in claim 1, wherein the composite material comprises less than about 50% fluoropolymer by weight.

13. The prosthetic valve as set forth in claim 1, wherein the elastomer is a TFE/PMVE copolymer.

14. The prosthetic valve as set forth in claim 13, wherein the TFE/PMVE copolymer comprises essentially of between about 40 and 80 weight percent perfluoromethyl vinyl ether and complementally 60 and 20 weight percent tetrafluoroethylene.

15. The prosthetic valve as set forth in claim 1, wherein the leaflet has a thickness of less than about 350 μm.

16. The prosthetic valve as set forth in claim 1, wherein the leaflet has a thickness of less than about 300 μm.

17. The prosthetic valve as set forth in claim 1, wherein the leaflet has a thickness of less than about 200 μm.

18. The prosthetic valve as set forth in claim 1, wherein the leaflet has a thickness of less than about 100 μm.

19. The prosthetic valve as set forth in claim 1, wherein the leaflet has a thickness of less than about 50 μm.

20. The prosthetic valve as set forth in claim 1, wherein the leaflet has a thickness of less than about 25 μm.

21. The prosthetic valve as set forth in claim 1, wherein the elastomer is a fluoroelastomer.

22. The prosthetic valve as set forth in claim 21, wherein the fluoropolymer layer is PTFE.

23. The prosthetic valve as set forth in claim 22, wherein the PTFE is ePTFE.

24. The prosthetic valve as set forth in claim 23, wherein the at least one fluoropolymer layer has a matrix tensile strength in at least one direction greater than about 96 MPa.

25. A prosthetic valve, comprising:
a leaflet comprising more than one layer of a composite material having at least one fluoropolymer layer having a plurality of pores and TFE/PMVE copolymer substantially filling the pores of the at least one fluoropolymer layer, the composite material comprising less than about 80% fluoropolymer by weight, the more than one layer of composite material being coupled together via the TFE/PMVE copolymer.

26. The prosthetic valve as set forth in claim 25, the leaflet having a ratio of leaflet thickness (μm) to number of fluoropolymer layers of less than about 5.

27. The prosthetic valve as set forth in claim 26, wherein the ratio of leaflet thickness (μm) to number of fluoropolymer layers of less than about 3.

28. The prosthetic valve as set forth in claim 26, wherein the ratio of leaflet thickness (μm) to number of fluoropolymer layers of less than about 1.

29. The prosthetic valve as set forth in claim 26, wherein the ratio of leaflet thickness (μm) to number of fluoropolymer layers of less than about 0.5.

30. The prosthetic valve as set forth in claim 25, wherein the leaflet encompasses a radiopaque element.

31. The prosthetic valve as set forth in claim 25, wherein the leaflet has a bending modulus of less than about 100 MPa.

32. The prosthetic valve as set forth in claim 25, wherein the leaflet is operatively coupled to a support frame and movable between closed and open configurations relative to the support frame.

33. The prosthetic valve as set forth in claim 32, wherein the support frame is selectively diametrically adjustable for endovascular delivery and deployment at a treatment site.

34. The prosthetic valve as set forth in claim 25, wherein the composite material comprises less than about 70% fluoropolymer by weight.

35. The prosthetic valve as set forth in claim 25, wherein the composite material comprises less than about 60% fluoropolymer by weight.

36. The prosthetic valve as set forth in claim 25, wherein the composite material comprises less than about 50% fluoropolymer by weight.

37. The prosthetic valve as set forth in claim 25, wherein the TFE/PMVE copolymer comprises essentially of between about 40 and 80 weight percent perfluoromethyl vinyl ether and complementally 60 and 20 weight percent tetrafluoroethylene.

38. The prosthetic valve as set forth in claim 25, wherein the leaflet has a thickness of less than about 350 μm.

39. The prosthetic valve as set forth in claim 25, wherein the leaflet has a thickness of less than about 300 μm.

40. The prosthetic valve as set forth in claim 25, wherein the leaflet has a thickness of less than about 200 μm.

41. The prosthetic valve as set forth in claim 25, wherein the leaflet has a thickness of less than about 100 μm.

42. The prosthetic valve as set forth in claim 25, wherein the leaflet has a thickness of less than about 50 μm.

43. The prosthetic valve as set forth in claim 25, wherein the leaflet has a thickness of less than about 25 μm.

44. The prosthetic valve as set forth in claim 25, wherein the fluoropolymer layer is PTFE.

45. The prosthetic valve as set forth in claim 44, wherein the PTFE is ePTFE.

46. The prosthetic valve as set forth in claim 45, wherein the at least one fluoropolymer layer has a matrix tensile strength in at least one direction greater than about 96 MPa.

47. A prosthetic valve, comprising:
a leaflet comprising more than one layer of a composite material having at least one fluoropolymer layer having a plurality of pores and an elastomeric material substantially filling the pores of the at least one fluoropolymer layer, the composite material comprising less than about 80% fluoropolymer by weight, the more than one layer of composite material being coupled together via the elastomeric material.

48. The prosthetic valve as set forth in claim 47, the leaflet having a ratio of leaflet thickness (μm) to number of fluoropolymer layers of less than about 5.

49. The prosthetic valve as set forth in claim 48, wherein the ratio of leaflet thickness (μm) to number of fluoropolymer layers of less than about 3.

50. The prosthetic valve as set forth in claim 48, wherein the ratio of leaflet thickness (μm) to number of fluoropolymer layers of less than about 1.

51. The prosthetic valve as set forth in claim 48, wherein the ratio of leaflet thickness (μm) to number of fluoropolymer layers of less than about 0.5.

52. The prosthetic valve as set forth in claim 47, wherein the leaflet encompasses a radiopaque element.

53. The prosthetic valve as set forth in claim 47, wherein the leaflet has a bending modulus of less than about 100 MPa.

54. The prosthetic valve as set forth in claim 47, wherein the leaflet is operatively coupled to a support frame and movable between closed and open configurations relative to the support frame.

55. The prosthetic valve as set forth in claim 54, wherein the support frame is selectively diametrically adjustable for endovascular delivery and deployment at a treatment site.

56. The prosthetic valve as set forth in claim 47, wherein the composite material comprises less than about 70% fluoropolymer by weight.

57. The prosthetic valve as set forth in claim 47, wherein the composite material comprises less than about 60% fluoropolymer by weight.

58. The prosthetic valve as set forth in claim 47, wherein the composite material comprises less than about 50% fluoropolymer by weight.

59. The prosthetic valve as set forth in claim 47, wherein the leaflet has a thickness of less than about 350 μm.

60. The prosthetic valve as set forth in claim 47, wherein the leaflet has a thickness of less than about 300 μm.

61. The prosthetic valve as set forth in claim 47, wherein the leaflet has a thickness of less than about 200 μm.

62. The prosthetic valve as set forth in claim 47, wherein the leaflet has a thickness of less than about 100 μm.

63. The prosthetic valve as set forth in claim 47, wherein the leaflet has a thickness of less than about 50 μm.

64. The prosthetic valve as set forth in claim 47, wherein the leaflet has a thickness of less than about 25 μm.

65. The prosthetic valve as set forth in claim 47, wherein the fluoropolymer layer is PTFE.

66. The prosthetic valve as set forth in claim 65, wherein the PTFE is ePTFE.

67. The prosthetic valve as set forth in claim 66, wherein the at least one fluoropolymer layer has a matrix tensile strength in at least one direction greater than about 96 MPa.

68. The prosthetic valve as set forth in claim 47, wherein the elastomeric material is a TFE/PMVE copolymer.

\* \* \* \* \*